US006190861B1

(12) United States Patent
Fishman

(10) Patent No.: US 6,190,861 B1
(45) Date of Patent: Feb. 20, 2001

(54) MOLECULAR SEQUENCES OF SWINE RETROVIRUSES METHOD OF USING

(75) Inventor: Jay A. Fishman, Wellesley, MA (US)

(73) Assignee: The General Hospital Corporation, Boston, MA (US)

(*) Notice: Under 35 U.S.C. 154(b), the term of this patent shall be extended for 0 days.

(21) Appl. No.: 08/766,528

(22) Filed: Dec. 13, 1996

Related U.S. Application Data

(63) Continuation-in-part of application No. 08/572,645, filed on Dec. 14, 1995, now abandoned.
(51) Int. Cl.$^7$ .............................. C12Q 1/70; C12Q 1/68; C07H 19/00; C07H 21/04
(52) U.S. Cl. .............................. 435/5; 435/6; 536/22.1; 536/23.1; 536/23.5; 536/24.3; 536/24.31
(58) Field of Search .......................... 435/5, 6; 536/22.1, 536/23.1, 23.5, 24.3, 24.31

(56) References Cited

U.S. PATENT DOCUMENTS

| 5,089,386 | 2/1992 | Stackebrandt et al. ................... 435/6 |
| 5,614,187 | * 3/1997 | Sachs ................................ 424/93.21 |

FOREIGN PATENT DOCUMENTS

WO 93/04169   3/1993   (WO).

OTHER PUBLICATIONS

Phan–Thanh et al., "Porcine retrovirus reverse transcriptase: optimal conditions for its determination" Dev. Biol. Stand. 72:111–117 (1990).
Aaronson et al., "Endogenous Type–C RNA Viruses of Mammalian Cells" Bio. et Biophys. Acta 458:323–354 (1976).
Armstrong et al., "C–type virus particles in pig kidney cell lines" J. Gen. Virol. 10:195–198 (1971).
Benveniste et al., "Evolution of type C viral genes: preservation of ancestral murine type C viral sequences in pig cellular DNA" PNAS 72:4090–4094 (1975).
Benveniste et al., "Homology between Type–C viruses of various species as determined by molecular hybridization" PNAS 70(12):3316–3320 (1973).
Benveniste et al., "Multiple divergent copies of endogenous C–type virogenes in mammalian cells", Nature 252:170–173 (1974).
Bouillant et al., "Multisequential transformation of a pig cell line (PFT): correlations between tumorigenicity and chromosome and ultrastructural markers", JNCI 64(4):783–788 (1980).
Bouillant et al., "Nontumoral, benign and malignant stages of transformation of a diploid pig cell line. A Review" Can. J. Comp. Med. 45:279–290 (1981).
Bouillant et al., "Type C virus production by a continuous line of pig oviduct cells (PFT)", J. Gen. Virol. 27:173 (1975).

Bouillant et al., "Ultrastructural comparison of Oncovirinae (type C), Spumavirinae, and Lentivirinae: three subfamilies of Retroviridae found in form animals", J. Nat. Cancer Institute 72:1075 (1984).
Busse et al., "Further investigations on the porcine lymphoma C–type particle (PLCP) and the possible biological significance of the virus in pigs", Ann. Rech. Vet. 5(4):651–658 (1978).
Busse et al., "Partial analysis of the polypeptide composition of a porcine lymphoma C–type particle (PLCP)" Zbl. Vet. Med. B. 28:118–125 (1981).
D'Aquila, R.T. "HIV–1 chemotherapy and drug resistance" Clinical and Diagnostic Virology 3:299–316 (1995).
D'Aquila, R.T. et al. "Zidovudine Resistance and HIV–1 Disease Progression during Antiretroviral Therapy" Annals of Internal Medicine 122(6):401–408 (1995).
Eron, J.J. et al. "Susceptibility testing by polymerase chain reaction DNA quantitation: A method to measure durg resistance of human immunodeficiency virus type 1 isolates" PNAS USA 89:3241–3245 (1992).
Fishman, J.A. "Miniature swine as organ donors for man: Strategies for prevention of xenotransplant–associated infections" Xenotransplantation 1:47–57 (1994).
Fishman, J.A. "Preventing infections in xenotransplantation: xenosis from miniature swine" Xeno 3(4):72–77 (1995).
Frazier, "Evidence for retrovirus in miniature swine with radiation–induced leukemia or metaplasia" Arch. of Virology 83:83–97 (1985).
Frazier et al., "Virus association with $^{90}$Sr Induced leukemia of miniature swine" Comparative Leukemia Res. 36:440–445 (1969).
Jarrett, "Evidence for the viral etiology of leukemia in the domestic mammals" Cancer Res. 13:39–62 (1970).
Kadota et al., "Ultrastructure and C–type particles in myeloid leukemia of a pig" Vet. Pathol. 21:263–265 (1984).
Kaeffer et al., "Histocompatible miniature pig (d/d haplotype): generation of hybridomas secreting A or M monoclonal antibody", Hybridoma 10:731 (1991).
Kaeffer et al., "Immortal porcine lymphoblastoid cell lines: interest for veterinary and medical research", Vet. Res. 25:425 (1994).
Kaeffer et al., "Histocompatible miniature boar model: selection of transformed cell lines of B and T lineages producing retrovirus" Int. J. Cancer 46:481–488 (1990).
Kaeffer et al., "Epithelioid and fibroblastic cell lines derived from the ileum of an adult histocompatible miniature board (dd/d haplotype) and immortalized by SV40 plasmid" Euro. J. of Cell Biology 62:152–162 (1993).
Lieber et al., "Biologic and immunologic properties of porcine Type C viruses" Virology 66:616 (1975).
Lieber et al., "Mammalian cells in culture frequently release type C viruses" Science 182:56–59 (1973).

(List continued on next page.)

Primary Examiner—Jezia Riley
(74) Attorney, Agent, or Firm—Hale and Dorr LLP

(57) ABSTRACT

Purified nucleic acid which can specifically hybridize with the sequence of swine retroviruses.

93 Claims, 76 Drawing Sheets

OTHER PUBLICATIONS

Moennig et al., "C–type particles produced by a permanent cell line from a leukemic pig. II. Physical chemical, and serological characterization of the particles", Virology 57:179 (1974).

Petters et al., "Gene transfer in swine embryos by injection of cells infected with retrovirus vectors" J. Exp. Zoology 242:85–88 (1987).

Phan–Thanh, L. et al. "Porcine retrovirus: optimal conditions for its biochemical detection" Arch. Virol. 123(3–4):255–265 (1992).

Rhim et al., "Characterization of murine sarcoma virus transformation of guinea pig cells and activation of an RNA tumor–like virus from nonproducer guinea pig cells" Bibl. Haematol. 153–164 (1975).

Schafer et al., "Polypeptides of mammalian oncornaviruses. II Characterization of murine leukemia virus polypeptide (p15) bearing interspecies reactivity" Virol. 63:48–59 (1975).

Schafer et al., "Morphological, chemical, and antigenic organization of mammalian C–type viruses", Bibl. Haematol. 497–515 (1975).

Schafer et al., "Evidence for the existence of different antigenic determinants of the interspecies type in mammalian RNA–C–type tumor viruses" (author's transl) Z Naturforsch [C] 28:214–222 (1973).

Sherr et al., "Interspecies antigenic determinants of the reverse transcriptases and p30 proteins of mammalian Type C viruses", J. Virol. 15:1440 (1975).

Smith, "Endogenous retroviruses in xenografts" NE J of Medicine 328 142–143 (1993).

Stoye, J.P. and J.M. Coffin "The dangers of xenotransplantation" Nature Medicine 1(11):1100 (1995).

Strandstrom et al., "C–type particles produced by a permanent cell line from a leukemic pig", Virology 57:175–178 (1974).

Suzuka, I. et al. "Molecular cloning of unintegrated closed circular DNA of porcine retrovirus" FEBS 198(2):339–343 (1986).

Suzuka, I. et al. "Some characteristics of a porcine retrovirus from a cell line derived from swine malignant lymphomas" FEBS 183(1):124–128 (1985).

Suzuki et al., "Production and characterization of monoclonal antibodies which affect RNA–dependent DNA polymerase activity of porcine retrovirus reverse transcriptase" Jpn J Vet Sci 50:295–297 (1988).

Takeyama et al., "Enhancement of fibroblast growth factor–induced diacylglycerol formationand protein kinase C activation by colon tumor–promoting bile acid in Swiss 3T3 cells" FEBS 3461 197:339–343 (1986).

Te Riele, H. et al. "Highly efficient gene targeting in embryonic stem cells through homologous recombination with isogenic DNA constructs" PNAS USA 89:5128–5132 (1992).

Todaro et al., "Characterization of a Type C virus released from the porcine cell line PK(15)", Virology 58:65 (1974).

Tumilowicz et al., "Concurrent replication of a papovavirus and a C–type virus in the CCL 33 porcine cell line" In Vitro 15:922–928 (1979).

Woods et al., "Antigenic and biochemical characterization of the C–type particle of the stable porcine kidney cell line PK–15", J. Virol. 12:1184 (1973).

Bowes, "Localization of a retroviral element within the rd gene coding the Beta Subunit of cGMP phosphodiesterase", PNAS USA 90:2955–2959 (1993).

Delassus et al., "Genetic Organization of Gibbon Ape Leukemia Virus", Virology 173:205–213 (1989).

Devare et al., "Nucleotide Sequence of the Simian Sarcoma Virus Genome: Demonstration that its Acquired Cellular Sequences Encode the Transforming Gene Product p28", PNAS USA 80:731–735 (1983).

* cited by examiner

```
CTCGAGACTC GGTGGAAGGG CCCTTATCTC GTACTTTTGA CCCACACCAAC    50    (SEQ. ID NO: 1)
GGCTGTGAAA GTCGAAGGAA TCTCCACCTG GATCCATGCA TCCCAGTTA     100
AGCCGCGCC  ACCTCCCGAT TCGGGGTGA  AGCCGAAAA  GACTGAAAAT    150
CCCCTTAAGC TTTGCCTCCA TCGCGTGGTT CCTTACTCTG TCAATAACCT    200
CTCAGACTAA TGTATGCGC  ATAGGAGACA GCCTGAACTC CCATAAACCC    250
TTATCTCTCA CCTGGTTAAT TACTGACTCC GGCACAGGTA TTAATATCAA    300
CAACACTCAA GGGGAGGCTC CTTTAGGAAC CTGGTGGCCT GATCTATACG    350
TTTGCCTCAG ATCAGTTATT CCTAGTCTGA CCCTCACCCC AGATATCCTC    400
CATGCTCACG GATTTTATGT TTGCCCAGGA CCACCAAATA ATGGAAAACA    450
TTGCCGAAAT CCCAGAGATT TCTTTTGTAA ACAATGGAAC TGTGTAACCT    500
CTAATGATGG ATATTGGAAA TGCCCAACCT CTCAGCAGGA TAGGGTAAGT    550
TTTTCTTATG TCAACACCTA TACCAGCTCT GGACAATTTA ATTACTGAC    600
CTGGATTAGA ACTGGAAGCC CCAAGTGCTC TCCTTCAGAC CTAGATTACC    650
TAAAAATAAG TTTCACTGAG AAAGGAAAAC AAGAAAATAT CCTAAAATGG    700
```

FIG. 1A (SEQ. ID NO: 1) cont'd

```
GTAAATGGTA TGTCTTGGGG AATGTATATAT TATGGAGGCT CGGGTAAACA  750
ACCAGGCTCC ATTCTAACTA TTCGCCTCAA AATAAACCAG CTGGAGCCTC  800
CAATGGCTAT AGGACCAAAT ACGGTCTTGA CGGGTCAAAG AACCCCAACC  850
CAAGGACCAG GACCATCCTC TAACATAACT TCTGGATCAG ACCCACTGA   900
GTCTAGCAGC ACGACTAAAA TGGGGGCAAA ACTTTTTTAGC CTCATCCAGG  950
GAGCTTTTCA AGCTCTTAAC TCCACGACTC CAGAGGCTAC CTCTCTTCTGT 1000
TGGCTATGCT TAGCTTTTGG CCCCACCTTAC TATGAAGGAA TGGCTAGAAG 1050
AGGGAAATTC AATGTGACAA AGAACATAG AGACCAATGC ACATGGGGAT 1100
CCCAAAATAA GCTTACCCTT ACTGAGGTTT CTGGAAAAGG CACCTGCATA 1150
GGAAAGGTTC CCCATCCCA CCAACACCTT TGTAACCACA CTGAAGCCTT 1200
TAATCAAACC TCTGAAAGTC AATATCTGGT ACCTGGTTAT GACAGGTGGT 1250
GGGCATGTAA TACTGGATTA ACCCCTTGTG TTTCCACCTT GGTTTTTAAC 1300
CAAACTAAAG ATTTTTGCAT TATGGTCCAA ATTGTTCCCC GAGTGTATTA 1350
CTATCCCGAA AAAGCAATCC TTGATGAATA TGACTACAGA AATCATGAC   1400
```

FIG. 1B (SEQ. ID NO: 1) cont'd

```
AAAAGAGAGA ACCCATATCT CTGACACTTG CTGTGATGCT CGGACTTGGA  1450
GTGGCAGCAG GTGTAGGAAC AGGAACAGCT GCCCTGGTCA CGGGACCACA  1500
GCAGCTAGAA ACAGGACTTA GTAACCTACA TCGAATTGTA ACAGAAGATC  1550
TCCAAGCCCT AGAAAAATCT GTCAGTAACC TGGAGGAATC CCTAACCTCC  1600
TTATCTGAAG TAGTCCTACA GAATAGAAGA GGGTTAGATT TATTATTTCT  1650
AAAAGAAGGA GGATTATGTG TAGCCTTGAA GGAGGAATGC TGTTTTTATG  1700
TGGATCATTC AGGGGCCATC AGAGACTCCA TGAACAAACT ACTCAAGGGT  1750
TTGGAGAAGC GTCGAAGGGA AAAGGAAACT ACTTCAAGGGT GGTTTGAGGG  1800
ATGGTTCAAC AGTCTCTCCT CGTTGGCTAC CCTACTTTCT GCTTTAACAG  1850
GACCCTTAAT AGTCCTCCTC CTGTTACTCA CAGTGGGCC ATGTATTATT  1900
AACAAGTTAA TTGCCTTCAT TAGAGAACGA ATAAGTGCAG TCCAGATCAT  1950
GGTACTTAGA CAACAGTACC AAAGCCCGTC TAGCAGGGAA GCTGGCCGCT  2000
AGCTCTACCA GTTCTAAGAT TAGAACTATT AACAAGAGAA GAAGTGGGGA  2050
ATGAAAGGAT GAAAATACAA CCTAAGCTAA TGAGAAGCTT AAAATTGTTC  2100
```

FIG. 1C (SEQ. ID NO: 1) cont'd

```
TGAATTCCAG AGTTGTTCC  TTATAGGTAA  AAGATTAGTT  TTTTTGCTGT   2150
TTTAAAATAT GCGGAAGTAA AATAGCCCT   GAGTACATGT  CTCTAGGCAT   2200
GAAACTTCTT GAAACTATTT GAGATAACAA  GAAAAGGGAG  TTTCTAACTG   2250
CTTGTTTAGC TTCTGTAAAA CTGTTGTGGC  CATAAAGATG  TTGAAATGTT   2300
GATACACATA TCTTGGTGAC AACATGTCTC  CCCACCCCG   AAACATGCGC   2350
AAATGTGTAA CTCTAAAACA ATTTAAATTA  ATTGGTCCAC  GAAGGCGGG    2400
CTCTCGAAGT TTTAAATTGA CTGGTTTGTG  ATATTTTGAA  ATGATTGGTT   2450
TGTAAAGCGC GGGCTTTGCT GTGAACCCCA  TAAAAGCTGT  CCCGACTCCA   2500
CACTGGGGC  CGCAGTCCTC TACCCCTCGG  TGGTGTAGGA  CTGTGGGCC    2550
CAGGCGGCCT GGAATAAAAA TCCTCTTGCT  GTTTGCATCA  AGACGCTTC    2600
TCGTGAGTGA TTAAGGGGAG TGCCTTTTC   CGAGCCTGGA  GGTTCTTTTT   2650
GCTGGTCTTA CATTGGGGG  CTTGTCCGGG  ATCTGTGCCG  CCACCCCTA    2700
ACACCCGAGA ACCGACTGG  AGTAAAAAG   GATCCTCTTT  TTAACGTGTA   2750
TGCATGTACC GCCGGGGTC  TCTGTTCTGA  GTGTCTGTTT  TCAGTGGTGC   2800
```

FIG. 1D (SEQ. ID NO: 1) cont'd

| | | | | |
|---|---|---|---|---|
| GGGCTTTCGG | TTTGCAGCTG | TCCTCTCAGG | CCGTAAGGGC | TGGGGGACTG | 2850 |
| TGATCAGCAG | AGTGCTAGG | AGGATCACAG | GCTGCTGCCC | TGGGGGACGC | 2900 |
| CCCGGGAGGT | GAGGAGAGCC | AGGGACGCCT | GGTGGTCTCC | TACTGTCGGT | 2950 |
| CAGAGGACCG | AATTCTGTTG | CTGAAGCCAA | AGCTTCCCCC | TCCGGGACCG | 3000 |
| TCCGACTCTT | TTGCCCTGCTT | GTGGAATACG | TGGACGGGTC | AGTGTGTCT | 3050 |
| GGATCTGTTG | GTTTCTGTTT | TGTGTGTCTT | TGTCTTGTGT | GTCCTTGTCT | 3100 |
| ACAGTTTTAA | TATGGACAGA | ACGGTGACGA | CCCCCTCTAG | TTTGACTCTC | 3150 |
| GACCATTGAA | CTGAAGTTAA | ATCCAGGGCT | CTTTCTGTGT | CTCTGAATGG | 3200 |
| TAAGAAGGGA | CCTTGGCAGA | GGGACCTTTA | ATTCTGAGAT | TATCCTGGCT | 3250 |
| ATGTTGGATG | GCCATCAGAG | GCTCTTCATC | CCGATCAGGA | 3300 |
| GTTAAAGCAA | TTATTTTCA | GACTGGACCC | AAGATTTGGC | AGAGGATCCT | 3350 |
| GCCCTATATC | CTTACGTGGC | AAGATTTGGC | CCGGCATTGGG | 3400 |
| TTAAACCATG | GCTGAATAAG | CCAAGAAAGC | CAGTCCCG | AATTCTGGCT | 3450 |
| CTTGGAGAGA | AAAACAAACA | CTGGCTGAA | AAAGTCAAGC | CCTCTCCTCA | 3500 |

FIG. 1E (SEQ. ID NO: 1) cont'd

```
TATCTACCCC GAGATTGAGG AACCACGGGC TTGGCCGGAA CCCCAATCTG    3550
TTCCCCCACC CCCTTATCTG GCACAGGGTG CCGGGAGGGG ACCCTTTGCC    3600
CCTCCTGGAG CTCGGGGGGT GGAGGGACCT TCTGCAGGGA CTCGGAGCCG    3650
GAGGGGCGCC ACCCCGGAGC GGACAGAGGA GATCGGGACA TTACCGCTGC    3700
GCACGTACGG CCCTCCCACA CCGGGGGGCC AATTGCAGCC CCTCCAGTAT    3750
TGGCCCTTTT CTTCTGCAGA TCTCTATAAT CCGGGGGGCC ACCATCCCCC    3800
TTTCTCGGAG GATCCCCAAC GCCTCACGGG GTTGGTGGAG TCCCTTATGT    3850
TCTCTCACCA GCCTACTTGG GATGATTGTC AACAGCTGCT GCAGACACTC    3900
TTCACAACCG AGGAGCGAGA GAGAATTCTA TTAGAGGCTA GAAAAAAATGT   3950
TCCTGGGGCC GACGGGCGAG CCAGCGCGGT GCAAAATGAG ATTGACATGG    4000
GATTCCCTT AACTCGCCCC GGTTGGGACT ACAACACGGC TGAAGGTAGG     4050
GAGAGCTTGA AAATCTATCG CCAGGCTCTG GTGGGGGGTC TCCGGGGGGC    4100
CTCAAGACGG CCCACTAATT TGGCTAAGGT AAGAGAAGTG ATGCAGGGAC    4150
CGAATGAACC CCCCTCTGTT TTTCTTGAGA GGCTCTTGGA AGCCTTCAGG    4200
```

FIG. 1F (SEQ. ID NO: 1) cont'd

```
CGGTACACCC CTTTTGATCC CACCTCAGAG GCCCAAAAAG CCTCAGTGGC   4250
TTTGGCCTTT ATAGGACAGT CAGCCTTTGA TATTAGAAAG AAGCTTCAGA   4300
GACTGGAAGG GTTACAGAGAG GCTGAGTTAC GTGATCTAGT GAAGGAGGCA   4350
GAGAAAGTAT ATTACAAAAG GGAGACAGAA GAAGAAAGGG AACAAAGAAA   4400
AGAGAGAGAA AGAGAGGAAA GGGAGGAAAG ACGTAATAAA CGGCAAGAGA   4450
AGAATTTGAC TAAGATCTTG GCTGCAGTGG TTGAAGGGAA AAGCAATACG   4500
GAAAGAGAGA GAGATTTTAG GAAAATTAGG TCAGGCCCTA GACAGTCAGG   4550
GAACCTGGGC AATAGGACCC CACTCGACAA GGACCAATGT GCATATTGTA   4600
AAGAAAGAGG ACACTGGGCA AGAACTGCC CCAAGAAGG AAACAAAGGA   4650
CCAAGGATCC TAGCTCTAGA AGAAGATAAA GATTAGGGGA GACGGGGTTC   4700
GGACCCCCTC CCCGAGCCCA GGGTAACTTT GAAGGTGGAG GGGCAACCAG   4750
TTGAGTTCCT GGTTGATACC GGAGCGAAAC ATTCAGTGCT ACTACAGCCA   4800
TTAGGAAAAC TAAAAGATAA AAAATCCTGG GTGATGGGTG CACAGGGCAA   4850
CAACAGTATC CATTGGACTAC CCGAAGACAG TTGACTTGGG AGTGGGACGG   4900
```

FIG. 1G (SEQ. ID NO: 1) cont'd

| | | | |
|---|---|---|---|
| GTAACCCACT | CGTTTCTGGT | CATACCTGAG | TGCCCAGCAC CCCTCTTAGG | 4950 |
| TAGAGACTTA | TTGACCAAGA | TGGGAGCACA | AATTTCTTTT GAACAAGGGA | 5000 |
| AACCAGAAGT | GTCTGCAAAT | AACAAACCTA | TCACTGTGTT GACCCTCCAA | 5050 |
| TTAGATGACG | AATATCGACT | ATACTCTCCC | CTAGTAAAGC CTGATCAAAA | 5100 |
| TATACAATTC | TGGTTGGAAC | AGTTTCCCCA | AGTTATTCA ACTGAAGGCC | 5150 |
| GGATGGGTTT | GGCAAAGCAA | GTTCCCCCAC | AAGTTATTCA ACTGAAGGCC | 5200 |
| AGTGCCACAC | CAGTGTCAGT | CAGACAGTAC | CCCTTGAGTA AAGAAGCTCA | 5250 |
| AGAAGGAATT | CGGCCGCATG | TCCAAAGATT | AATACTCCCC GGCATCCTAG | 5300 |
| TTCCTGTCCA | ATCTCCCTGG | AATACTCCCC | TGCTACCGGT TAGAAAGCCT | 5350 |
| GGGACTAATG | ACTATCGACC | AGTACAGGAC | TTGAGAGAGG TCAATAAACG | 5400 |
| GGTGCAGGAT | ATACACCCAA | CAGTCCGAA | CCCTTATAAC CTCTGTGTG | 5450 |
| CTCTCCCACC | CCAACGGAGC | TGTATATACAG | TATTGGACTT AAAGGATGCC | 5500 |
| TTCTTCTGCC | TGAGATTACA | CCCCACTAGC | CAACCACTTT TTGCCTTGA | 5550 |
| ATGGAGAGAT | CCAGGTACGG | GAAGAACCGG | GCAGCTCACC TGGACCCGAC | 5600 |
| TGCCCCAAGG | GTTCAAGAAC | TCCCCGACCA | TCTTTGACGA AGCCCTACAC | 5650 |

FIG. 1H (SEQ. ID NO: 1) cont'd

| | | | | |
|---|---|---|---|---|
| AGAGACCTGG | CCAACTTCAG | GATCCAACAC | CCTCAGGTGA | CCCTCCTCCA | 5700 |
| GTAGGTGGAT | GACCTGCTTC | TGGCGGGAGC | CACCAAACAG | GACTGCTTAG | 5750 |
| AAGGCACGAA | GGCACTACTG | CTGGAATTGT | CTGACCTAGG | CTACAGAGCC | 5800 |
| TCTGCTAAGA | AGCCCAGAT  | TTGCAGGAGA | GAGTAACAT  | ACTTGGGGTA | 5850 |
| CAGTTTACGG | GACGGGCAGC | GATGGCTGAC | GGAGGCACGG | AAGAAAACTG | 5900 |
| TAGTCCAGAT | ACCGGGCCCA | ACCACAGCCA | AACAAATGAG | AGAGTTTTTG | 5950 |
| GGGACAGCTG | GATTTTGCAG | ACTGTGGATC | CCGGGTTTG  | CGACCTTAGC | 6000 |
| AGCCCCACTC | TACCCGCTAA | CCAAAGAAAA | AGGGAATTC  | TCCTGGGCTC | 6050 |
| CTGAGCACCA | GAAGGCATTT | GATGCTATCA | AAAAGCCCT  | GCTGAGGGCA | 6100 |
| CCTGCTCTGG | CCCTCCCTGA | CGTAACTAAA | CCCTTTACCC | TTTATGTGAA | 6150 |
| TGAGCGTAAG | GGAGTAGCCC | GGGGAGTTTT | AACCCAAACC | CTAGGACCAT | 6200 |
| GGAGAAGACC | TGTCGCCTAC | CTGTCAAAGA | AGCTCGATCC | TGTAGCCAGT | 6250 |
| GGTTGGCCCA | TATGCCTGAA | GGCTATGCCA | GCTGTGGCCA | TACTGGTCAA | 6300 |
| GGACGCTGAC | AAATTGACTT | TGGACAAGA  | ATATAACTGT | AATAGCCCCC | 6350 |

FIG. 1I (SEQ. ID NO: 1) cont'd

| | | | | |
|---|---|---|---|---|
| CATGCATTGG | AGAACATCGT | TGGGCAGCCC | CCAGACCGAT | GGATGACCAA | 6400 |
| CGCCCGCATG | ACCCACTATC | AAAGCCTGCT | TCTCACAGAG | AGGGTCACGT | 6450 |
| TCGCTCCACC | AACCGCTCTC | AACCCTGCCA | CTCTTCTGCC | TGAAGAGACT | 6500 |
| GATGAACCAG | TGACTCATGA | TTGCCATCAA | CTATTGATTG | AGGAGACTGG | 6550 |
| GGTCCGCAAG | GACCTTACAG | GACTGGAGAA | GACATACCGCT | GTGCTAACCT | 6600 |
| GGTTCACTGA | CGGAAGCAGC | TATGTGGTGG | AAGGTAAGAG | GATGGCTGGG | 6650 |
| GCGGCGGTGG | TGGACGGGAC | CCGCACGATC | TGGGCCAGCA | GCCTGCCGGG | 6700 |
| AGGAACTTCA | GCACAAAAGG | CTGAGCTCAT | GGCCCTTCACG | CAAGCTTTGC | 6750 |
| GGCTGGCCGA | AGGGAAATCC | ATAAACATTT | ATACGGACAG | CAGGTATGCC | 6800 |
| TTTGCCGACTG | CACACAGTACA | TGGGCCATC | TATAAACAAA | GGGGGTTGCT | 6850 |
| TACCTCAGCA | GGGAGGGAAA | TAAAGAACAA | AGAGGAAATT | CTAAGCCTAT | 6900 |
| TAGAAGCCGT | ACATTTACCA | AAAAGGCTAG | CTATTATACA | CTGTCCTGA | 6950 |
| CATCAGAAAG | CTAAAGATCT | CATATCCAGA | GGAAACCAGA | TGGCTGACCG | 7000 |
| GGTTGCCAAG | CAGGCAGCCC | AGGGTGTTAA | CCTTCTGCCT | ATAATAGAAA | 7050 |

FIG. 1J (SEQ. ID NO: 1) cont'd

| | | | | | |
|---|---|---|---|---|---|
| TGCCCAAAGC | CCCAGAACCC | AGAGGACAGT | ACACCCTAGA | AGACTGGCAA | 7100 |
| GAGATAAAAA | AGATAGACCA | TTCTCTGAGA | CTCCGGAAGG | GACCTGCTAT | 7150 |
| ACCTCAGATG | GGAAGGAAAT | CCTGCCCCAC | AAAGAAGGGT | TAGAATATGT | 7200 |
| CCAACAAGAT | ACATCGTCTA | ACCCACCTAG | GAACTAAACA | CCTGCAGCAG | 7250 |
| TTGGTCAGAA | CATCCCCTTA | TCATGTTCTG | AGGCTACCAG | GAGTGGCTGA | 7300 |
| CTCGGTGGTC | AAACATTGTG | TGCCCTGCCA | GCTGGTTAAT | GCTAATCCTT | 7350 |
| CCAGAATGCC | TCCAGGGAAG | AGACTAAGGG | GAAGCCACCC | AGGGCGCTCAC | 7400 |
| TGGAAGTGG | ACTTCACTGA | GGTAAAGCCG | GCTAAATATG | GAAACAAATA | 7450 |
| CCTATTGGTT | TTTGTAGACA | CCTTTTTCAG | ATGGGTAGAG | GCTTATCCTA | 7500 |
| CTAAGAAAGA | GACTTCAACC | GTGGTAGCTA | AAAAAATACT | TGGAAGAAATT | 7550 |
| TTTCCAAGAT | TGGAATACC | CAGGTAAGTC | AGGGACTGCC | ATGGTCAGC | 7600 |
| TTTTGTTGCC | CAGGTAAGTC | AGGGACTGCC | CAAGATATTG | GGGATTGATT | 7650 |
| GGAAACTGCA | TGTGCATAC | AGACCCCAAA | GCTCAGGACA | GGTAGAGAGG | 7700 |
| ATGAATAGAA | CCATTAAAGA | GACCCTTACT | AAATTGACCG | CGGAGACTGG | 7750 |

FIG. 1K (SEQ. ID NO: 1) cont'd

```
CGTTAATGAT TGGATAGCTC TCCTGCCCTT TGTGCTTTTT AGGGTTAGGA    7800
ACACCCCTGG ACAGTTTGGG CTGACCCCCT ATGAATTACT CTACGGGGGA    7850
CCCCCCCCAT TGGTAGAAAT TGCTTCTGTA CATAGTGCTG ATGTGCTGCT    7900
TTCCAGCCCT TTGTTCTCTA GGCTCAAGGC ACTTGAGTGG GTGAGACAAC    7950
GAGGGTGGAG GCAACTCCGG GAGGCCTACT CAGGAGGAGG AGACTTGCAG    8000
ATCCCACATC GTTTCCAAGT GGGAGATTCA GTCTACGTTA GAGCCCACCG    8050
TGCAGGAAAC                                                8060
```

FIG. 1L (SEQ. ID NO: 2)

```
         10         20         30         40         50         60
          *          *          *          *          *          *
CTACCCCTGC GTGGTGTACG ACTGTGGGCC CCAGCGCGCT TGGAATAAAA ATCCTCTTGC 70         80         90        100        110        120
          *          *          *          *          *          *
TGTTTGCATC AAGACCCGCT CTTGTGAGTG ATTTGGGGTG TCGCCTCTTC CGAGCCCGGA 130        140        150        160        170        180
          *          *          *          *          *          *
CGAGGGGGAT TGTTCTTTTA CTGGCCTTTC ATTTGGTGCG TTGGCCGGGA AATCCTGGA 190        200        210        220        230        240
          *          *          *          *          *          *
CCACCCCTTA CACCCGAGAA GGGTCTCTG CCGACTTGGA GGTAAAGGGA TCCCCTTTGG AACATATGTG 250        260        270        280        290        300
          *          *          *          *          *          *
TGTGTCGGCC GGGTCTCTG TTCTGAGTGT CTGTTTTCGG TGATGCGCGC TTTCGGTTTG 310        320        330        340        350        360
          *          *          *          *          *          *
CAGCTGTCCT CTCAGACCGT AAGGACTGGA GGACTGTGAT CAGCAGACGT GCTAGGAGGA
```

FIG. 2A (SEQ. ID NO: 2) cont'd

```
          370        380        390        400        410        420
            *          *          *          *          *          *
TCACAGGCTG CCACCCTGGG GTGGGTCAGA GGAGGTGGGG AGAGCCAGGG ACGCCTGGTG 430        440        450        460        470        480
            *          *          *          *          *          *
GTCTCCTACT GTGGGTCAGA GGACCGAGTT CTGTTGTTGA AGGGAAAGCT TCCCCCTCCG 490        500        510        520        530        540
            *          *          *          *          *          *
CGGCGGTCCG ACTCTTTTGC CTGCTTGTGG AAGACGCGGA CGGGTGCGGT GTGTCTGGAT 550        560        570        580        590        600
            *          *          *          *          *          *
CTGTTGGTTT CTGTTTCGTG TGTCTTTGTC TTGTGCGTCC TTGTCTACAG TTTTAAT ATG
                                                              Met>

610        620        630        640
            *          *          *          *
GGA CAG ACA GTG ACT ACC CCC CTT AGT TTG ACT CTC GAC CAT TGG ACT
Gly Gln Thr Val Thr Thr Pro Leu Ser Leu Thr Leu Asp His Trp Thr>
```

FIG. 2B (SEQ. ID NO: 2) cont'd

```
       650            660            670            680            690
        *              *              *              *              *
              GAA GTT AGA TCC AGG GCT CAT AAT TTG TCA GTT CAG GTT AAG AAG GGA
              Glu Val Arg Ser Arg Ala His Asn Leu Ser Val Gln Val Lys Lys Gly>

700            710            720            730            740
        *              *              *              *              *
              CCT TGG CAG ACT TTC TGT GCC TCT GAA TGG CCA ACA TTC GAT GTT GGA
              Pro Trp Gln Thr Phe Cys Ala Ser Glu Trp Pro Thr Phe Asp Val Gly>

750            760            770            780            790
        *              *              *              *              *
              TGG CCA TCA GAG GGG ACC TTT AAT TCT GAA ATT ATC CTG GCT GTT AAG
              Trp Pro Ser Glu Gly Thr Phe Asn Ser Glu Ile Ile Leu Ala Val Lys>

800            810            820            830            840
        *              *              *              *              *
              GCA ATC ATT TTT CAG ACT GGA CCC GGC TCT CAT CCT GAT CAG GAG CCC
              Ala Ile Ile Phe Gln Thr Gly Pro Gly Ser His Pro Asp Gln Glu Pro>

850            860            870            880
        *              *              *              *
              TAT ATC CTT ACG TGG CAA GAT TTG GCA GAA GAT CCT CCG CCA TGG GTT
              Tyr Ile Leu Thr Trp Gln Asp Leu Ala Glu Asp Pro Pro Pro Trp Val>
```

FIG. 2C (SEQ. ID NO: 2) cont'd

```
        890         900         910         920         930
         *           *           *           *           *
                   AAA CCA TGG CTA AAT AAA CCA AGA AAG CCA GGT CCC CGA ATC CTG GCT
                   Lys Pro Trp Leu Asn Lys Pro Arg Lys Pro Gly Pro Arg Ile Leu Ala>

940         950         960         970         980
         *           *           *           *           *
CTT GGA GAG AAA AAC AAA CAC TCG GCC GAA AAA GTC GAG CCC TCT CCT
Leu Gly Glu Lys Asn Lys His Ser Ala Glu Lys Val Glu Pro Ser Pro>

990        1000        1010        1020        1030
         *           *           *           *           *
CGT ATC TAC CCC GAG ATC GAG GAG CCG CCG ACT TGG CCG GAA CCC CAA
Arg Ile Tyr Pro Glu Ile Glu Glu Pro Pro Thr Trp Pro Glu Pro Gln>

1040        1050        1060        1070        1080
         *           *           *           *           *
CCT GTT CCC CCA CCC CCT TAT CCA GCA CAG GGT GCT GTG AGG GGA CCC
Pro Val Pro Pro Pro Pro Tyr Pro Ala Gln Gly Ala Val Arg Gly Pro>

1090        1100        1110        1120
         *           *           *           *
TCT GCC CCT CCT GGA GCT CCG GTG GTG GAG GGA CCT GCT GCC GGG ACT
Ser Ala Pro Pro Gly Ala Pro Val Val Glu Gly Pro Ala Ala Gly Thr>
```

FIG. 2D (SEQ. ID NO: 2) cont'd

```
        1130            1140            1150            1160            1170
          *               *               *               *               *
        CGG AGC CGG AGA GGC GCC ACC CCG GAG CGG ACA GAC GAG ATC GCG ATA
        Arg Ser Arg Arg Gly Ala Thr Pro Glu Arg Thr Asp Glu Ile Ala Ile>

1180            1190            1200            1210            1220
          *               *               *               *               *
        TTA CCG CTG CGC ACC TAT GGC CCT CCC ATG CCA GGG GGC CAA TTG CAG
        Leu Pro Leu Arg Thr Tyr Gly Pro Pro Met Pro Gly Gly Gln Leu Gln>

1230            1240            1250            1260            1270
          *               *               *               *               *
        CCC CTC CAG TAT TGG CCC CCT TTC TCT GCA GAT CTC TAT AAT TGG AAA
        Pro Leu Gln Tyr Trp Pro Pro Phe Ser Ala Asp Leu Tyr Asn Trp Lys>

1280            1290            1300            1310            1320
          *               *               *               *               *
        ACT AAC CAT CCC CCT TTC TCG GAG GAT CCC CAA CGC CTC ACG GGG TTG
        Thr Asn His Pro Pro Phe Ser Glu Asp Pro Gln Arg Leu Thr Gly Leu>

1330            1340            1350            1360
          *               *               *               *
        GTG GAG TCC CTT ATG TTC TCT CAC CAG CCT ACT TGG GAT GAT TGT CAA
        Val Glu Ser Leu Met Phe Ser His Gln Pro Thr Trp Asp Asp Cys Gln>
```

FIG. 2E (SEQ. ID NO: 2) cont'd

```
      1370        1380        1390        1400        1410
        *           *           *           *           *
                CAG CTG CTG CAG ACA CTC TTC ACA ACC GAG GAG CGA GAG AGA ATT CTG
                Gln Leu Leu Gln Thr Leu Phe Thr Thr Glu Glu Arg Glu Arg Ile Leu>

1420        1430        1440        1450        1460
        *           *           *           *           *
        TTA GAG GCT AAA AAA AAT GTT CCT GGG GCC GAC GGG CGA CCC ACG CAG
        Leu Glu Ala Lys Lys Asn Val Pro Gly Ala Asp Gly Arg Pro Thr Gln>

1470        1480        1490        1500        1510
        *           *           *           *           *
        TTG CAA AAT GAG ATT GAC ATG GGA TTT CCC TTG ACT CGC CCC GGT TGG
        Leu Gln Asn Glu Ile Asp Met Gly Phe Pro Leu Thr Arg Pro Gly Trp>

1520        1530        1540        1550        1560
        *           *           *           *           *
        GAC TAC AAC ACG GCT GAA GGT AGG GAG AGC TTG AAA ATC TAT CGC CAG
        Asp Tyr Asn Thr Ala Glu Gly Arg Glu Ser Leu Lys Ile Tyr Arg Gln>

1570        1580        1590        1600
        *           *           *           *
        GCT CTG GTG GCG GGT CTC CGG GGC GCC TCA AGA CGG CCC ACT AAT TTG
        Ala Leu Val Ala Gly Leu Arg Gly Ala Ser Arg Arg Pro Thr Asn Leu>
```

FIG. 2F (SEQ. ID NO: 2) cont'd

```
        1610      1620      1630      1640      1650
          *         *         *         *         *
        GCT AAG GTA AGA GAG GTG ATG CAG GGA AAC GAA CCT CCC TCG GTA
        Ala Lys Val Arg Glu Val Met Gln Gly Asn Glu Pro Pro Ser Val>

1660      1670      1680      1690      1700
          *         *         *         *         *
        TTT CTT GAG AGG CTC ATG GAA GCC TTC AGG CGG TTC ACC CCT TTT GAT
        Phe Leu Glu Arg Leu Met Glu Ala Phe Arg Arg Phe Thr Pro Phe Asp>

1710      1720      1730      1740      1750
          *         *         *         *         *
        CCT ACC TCA GAG GCC CAG AAA GCC TCA GTG GCC CTG GCC TTC ATT GGG
        Pro Thr Ser Glu Ala Gln Lys Ala Ser Val Ala Leu Ala Phe Ile Gly>

1760      1770      1780      1790      1800
          *         *         *         *         *
        TCG GCT CTG GAT ATC AGG AAG AAA CTT CAG AGA CTG GAA GGG TTA
        Ser Ala Leu Asp Ile Arg Lys Lys Leu Gln Arg Leu Glu Gly Leu>

1810      1820      1830      1840
          *         *         *         *
        CAG GAG GCT GAG TTA CGT GAT CTA GTG AGA GAG GCA GAG AAG GTG TAT
        Gln Glu Ala Glu Leu Arg Asp Leu Val Arg Glu Ala Glu Lys Val Tyr>
```

FIG. 2G (SEQ. ID NO: 2) cont'd

```
     1850        1860        1870        1880        1890
       *           *           *           *           *
                 TAC AGA AGG GAG ACA GAA GAG AAG GAA CAG AGA AAA GAA AAG GAG
                 Tyr Arg Arg Glu Thr Glu Glu Lys Glu Gln Arg Lys Glu Lys Glu>

1900        1910        1920        1930        1940
       *           *           *           *           *
AGA GAA AGG GAG GAA AGA CGT GAT AGA CGG CAA GAG AAG AAT TTG
Arg Glu Glu Arg Glu Arg Arg Asp Arg Arg Gln Glu Lys Asn Leu>

1950        1960        1970        1980        1990
       *           *           *           *           *
ACT AAG ATC TTG GCC GCA GTG GTT GAA GGG AAG AGC AGC AGG AGA
Thr Lys Ile Leu Ala Ala Val Val Glu Gly Lys Ser Ser Arg Arg>

2000        2010        2020        2030        2040
       *           *           *           *           *
GAG AGA GAT TTT AGG AAA ATT AGG TCA GGC CCT AGA CAG TCA GGG AAC
Glu Arg Asp Phe Arg Lys Ile Arg Ser Gly Pro Arg Gln Ser Gly Asn>

2050        2060        2070        2080
       *           *           *           *
CTG GGC AAT AGG ACC CCA CTC GAC AAG GAC CAG TGT GCG TAT TGT AAA
Leu Gly Asn Arg Thr Pro Leu Asp Lys Asp Gln Cys Ala Tyr Cys Lys>
```

FIG. 2H (SEQ. ID NO: 2) cont'd

```
      2090          2100          2110          2120          2130
        *             *             *             *             *
              GAA AAA GGA CAC TGG GCA AGG AAC TGC CCC AAG AAG GGA AAC AAA GGA
              Glu Lys Gly His Trp Ala Arg Asn Cys Pro Lys Lys Gly Asn Lys Gly>

2140          2150          2160          2170          2180
        *             *             *             *             *
              CCG AAG GTC CTA GCT CTA GAA GAT AAA GAT T AGGGGAGACG
              Pro Lys Val Leu Ala Leu Glu Asp Lys Asp>

2190          2200          2210          2220          2230          2240
        *             *             *             *             *             *
GGGTTCGGAC CCCTCCCCG AGCCCAGGGT AACTTTGAAG GTGAGGGGC AACCAGTTGA 2250          2260          2270          2280          2290          2300
        *             *             *             *             *             *
GTTCCTGGTT GATACCGGAG CGGAGCATTC AGTGCTGCTA CAACCATTAG GAAAACTAAA 2310          2320          2330          2340          2350
        *             *             *             *             *
AGAAAAAAAA TCCTGGGTG ATG GGT GCC ACA GGG CAA CGG CAG TAT CCA TGG
                        Met Gly Ala Thr Gly Gln Arg Gln Tyr Pro Trp>
```

FIG. 21

(SEQ. ID NO: 2) cont'd

```
       2360        2370        2380        2390        2400
         *           *           *           *           *
ACT ACC CGA AGA ACC GTT GAC TTG GGA GTG GGA CGG GTA ACC CAC TCG
Thr Thr Arg Arg Thr Val Asp Leu Gly Val Gly Arg Val Thr His Ser>

2410        2420        2430        2440
         *           *           *           *
TTT CTG GTC ATC CCT GAG TGC CCA GTA CCC CTT CTA GGT AGA GAC TTA
Phe Leu Val Ile Pro Glu Cys Pro Val Pro Leu Leu Gly Arg Asp Leu>

2450        2460        2470        2480        2490
  *           *           *           *           *
CTG ACC AAG ATG GGA GCT CAA ATT TCT TTT GAA CAA AGA CCA GAA
Leu Thr Lys Met Gly Ala Gln Ile Ser Phe Glu Gln Gly Arg Pro Glu>

2500        2510        2520        2530        2540
         *           *           *           *           *
GTG TCT GTG AAT AAC AAA CCC ATC ACT GTG TTG ACC CTC CAA TTA GAT
Val Ser Val Asn Asn Lys Pro Ile Thr Val Leu Thr Leu Gln Leu Asp>

2550        2560        2570        2580        2590
         *           *           *           *           *
GAT GAA TAT CGA CTA TAT TCT CCC CAA GTA AAG CCT GAT CAA GAT ATA
Asp Glu Tyr Arg Leu Tyr Ser Pro Gln Val Lys Pro Asp Gln Asp Ile>
```

FIG. 2J (SEQ. ID NO: 2) cont'd

```
       2600        2610        2620        2630        2640
         *           *           *           *           *
CAG TCC TGG TTG GAG CAG TTT CCC CAA GCC TGG GCA GAA ACC GCA GGG
Gln Ser Trp Leu Glu Gln Phe Pro Gln Ala Trp Ala Glu Thr Ala Gly>

2650        2660        2670        2680
         *           *           *           *
ATG GGT TTG GCA AAG CAA GTT CCC CCA CAG GTT ATT CAA CTG AAG GCC
Met Gly Leu Ala Lys Gln Val Pro Pro Gln Val Ile Gln Leu Lys Ala>

2690        2700        2710        2720        2730
   *           *           *           *           *
AGT GCT ACA CCA GTA TCA GTC AGA CAG TAC CCC TTG AGT AGA GAG GCT
Ser Ala Thr Pro Val Ser Val Arg Gln Tyr Pro Leu Ser Arg Glu Ala>

2740        2750        2760        2770        2780
         *           *           *           *           *
CGA GAA GGA ATT TGG CCG CAT GTT CAA AGA TTA ATC CAA CAG GGC ATC
Arg Glu Gly Ile Trp Pro His Val Gln Arg Leu Ile Gln Gln Gly Ile>

2790        2800        2810        2820        2830
         *           *           *           *           *
CTA GTT CCT GTC CAA TCC CCT TGG AAT ACT CCC CTG CTA CCG GTT AGG
Leu Val Pro Val Gln Ser Pro Trp Asn Thr Pro Leu Leu Pro Val Arg>
```

FIG. 2K

FIG. 2L (SEQ. ID NO: 2) cont'd

```
      2840            2850            2860            2870            2880
       *               *               *               *               *
AAG CCT GGG ACC AAT GAT TAT CGA CCA GTA CAG GAC TTG AGA GAG GTC
Lys Pro Gly Thr Asn Asp Tyr Arg Pro Val Gln Asp Leu Arg Glu Val>

2890            2900            2910            2920
       *               *               *               *
AAT AAA AGG GTG CAG GAC ATA CAC CCA ACG GTC CCG AAC CCT TAT AAC
Asn Lys Arg Val Gln Asp Ile His Pro Thr Val Pro Asn Pro Tyr Asn>

2930            2940            2950            2960            2970
  *               *               *               *               *
CTC TTG AGC GCC CTC CCG CCT GAA CGG AAC TGG TAC ACA GTA TTG GAC
Leu Leu Ser Ala Leu Pro Pro Glu Arg Asn Trp Tyr Thr Val Leu Asp>

2980            2990            3000            3010            3020
       *               *               *               *               *
TTA AAA GAT GCC TTC TGC CTG AGA TTA CAC CCC ACT AGC CAA CCA
Leu Lys Asp Ala Phe Cys Leu Arg Leu His Pro Thr Ser Gln Pro>

3030            3040            3050            3060            3070
       *               *               *               *               *
CTT TTT ACC TTC GAA TGG AGA GAT CCA GGT ACG GGA AGA ACC GGG CAG
Leu Phe Thr Phe Glu Trp Arg Asp Pro Gly Thr Gly Arg Thr Gly Gln>
```

(SEQ. ID NO: 2) cont'd

```
         3080           3090           3100           3110           3120
           *              *              *              *              *
CTC ACC TGG ACC CGA CTG CCC CAA GGG TTC AAG AAC TCC CCG ACC ATC
Leu Thr Trp Thr Arg Leu Pro Gln Gly Phe Lys Asn Ser Pro Thr Ile>

3130           3140           3150           3160
           *              *              *              *
TTT GAC GAA GCC CTA CAC AGG GAC CTG GCC AAC TTC AGG ATC CAA CAC
Phe Asp Glu Ala Leu His Arg Asp Leu Ala Asn Phe Arg Ile Gln His>

3170           3180           3190           3200           3210
  *              *              *              *              *
CCT CAG GTG ACC CTC CAG TAC GTG GAT GAC CTG CTT CTG GCG GGA
Pro Gln Val Thr Leu Gln Tyr Val Asp Asp Leu Leu Leu Ala Gly>

3220           3230           3240           3250           3260
           *              *              *              *              *
GCC ACC AAA CAG GAC TGC TTA GAA GGT ACG AAG GCA CTA CTG CTG GAA
Ala Thr Lys Gln Asp Cys Leu Glu Gly Thr Lys Ala Leu Leu Leu Glu>

3270           3280           3290           3300           3310
           *              *              *              *              *
TTG TCT GAC CTA GGC TAC AGA GCC TCT GCT AAG AAG GCC CAG ATT TGC
Leu Ser Asp Leu Gly Tyr Arg Ala Ser Ala Lys Lys Ala Gln Ile Cys>
```

FIG. 2M (SEQ. ID NO: 2) cont'd

```
         3320           3330           3340           3350           3360
          *              *              *              *              *
AGG AGA GAG GTA ACA TAC TTG GGG TAC AGT TTG CGG GGC GGG CAG CGA
Arg Arg Glu Val Thr Tyr Leu Gly Tyr Ser Leu Arg Gly Gly Gln Arg>

3370           3380           3390           3400
          *              *              *              *
TGG CTG ACG GAG GCA CGG AAG AAA ACT GTA GTC CAG ATA CCG GCC CCA
Trp Leu Thr Glu Ala Arg Lys Lys Thr Val Val Gln Ile Pro Ala Pro>

3410           3420           3430           3440           3450
  *              *              *              *              *
ACC ACA GCC AAA CAA GTG AGA GAG TTT TTG GGG ACA GCT GGA TTT TGC
Thr Thr Ala Lys Gln Val Arg Glu Phe Leu Gly Thr Ala Gly Phe Cys>

3460           3470           3480           3490           3500
          *              *              *              *              *
AGA CTG TGG ATC CCG GGG TTT GCG ACC TTA GCA GCC CCA CTC TAC CCG
Arg Leu Trp Ile Pro Gly Phe Ala Thr Leu Ala Ala Pro Leu Tyr Pro>

3510           3520           3530           3540           3550
          *              *              *              *              *
CTA ACC AAA GAA AAA GGG GGT TGC TTA CCT CAG CAG GGA AAA TA AAG
Leu Thr Lys Glu Lys Gly Gly Cys Leu Pro Gln Gln Gly Lys  *  Lys
                         Lys Arg Gly Leu Leu Thr Ser Ala Gly Arg Glu Ile Lys>
```

FIG. 2N (SEQ. ID NO: 2) cont'd

```
         3560            3570           3580           3590           3600
            *               *              *              *              *
AAC AAA GAG GAA ATT CTA AGC CTA TTA GAA GCC TTA CAT TTG CCA AAA
Asn Lys Glu Glu Ile Leu Ser Leu Leu Glu Ala Leu His Leu Pro Lys>

3610            3620           3630           3640           3650
            *               *              *              *              *
AGG CTA GCT ATT ATA CAC TGT CCT GGA CAT CAG AAA GCC AAA GAT CTC
Arg Leu Ala Ile Ile His Cys Pro Gly His Gln Lys Ala Lys Asp Leu>

3660            3670           3680           3690
            *               *              *              *
ATA TCT AGA GGG AAC CAG ATG GCT GAC CGG GTT GCC AAG CAG GCA GCC
Ile Ser Arg Gly Asn Gln Met Ala Asp Arg Val Ala Lys Gln Ala Ala>

3700            3710           3720           3730           3740
            *               *              *              *              *
CAG GCT GTT AAC CTT CTG CCT ATA GAA ACC CCC AAA ACC CCA GAA
Gln Ala Val Asn Leu Leu Pro Ile Ile Glu Thr Pro Lys Ala Pro Glu>

3750            3760           3770           3780           3790
            *               *              *              *              *
CCC AGA CGA CAG TAC ACC CTA GAA GAC TGG CAA GAG ATA AAA AAG ATA
Pro Arg Arg Gln Tyr Thr Leu Glu Asp Trp Gln Glu Ile Lys Lys Ile>
```

FIG. 2O

FIG. 2P (SEQ. ID NO: 2) cont'd

```
      3800            3810            3820            3830            3840
       *       *       *       *       *       *       *       *       *
GAC CAG TTC TCT GAG ACT CCG GAG GGG ACC TGC TAT ACC TCA TAT GGG
Asp Gln Phe Ser Glu Thr Pro Glu Gly Thr Cys Tyr Thr Ser Tyr Gly>

3850            3860            3870            3880            3890
       *       *       *       *       *       *       *       *       *
AAG GAA ATC CTG CCC CAC AAA GAA GGG TTA GAA TAT GTC CAA CAG ATA
Lys Glu Ile Leu Pro His Lys Glu Gly Leu Glu Tyr Val Gln Gln Ile>

3900            3910            3920            3930
       *       *       *       *       *       +       *       *
CAT CGT CTA ACC CAC CTA GGA ACT AAA CAC CTG CAG CAG TTG GTC AGA
His Arg Leu Thr His Leu Gly Thr Lys His Leu Gln Gln Leu Val Arg>

3950            3960            3970            3980
       *       *       *       *       *       *       *       *       *
ACA TCC CCT TAT CAT GTT CTG AGG CTA CCA GGA GTG GCT GAC TCG GTG
Thr Ser Pro Tyr His Val Leu Arg Leu Pro Gly Val Ala Asp Ser Val>

3990          4000            4010            4020            4030
 *     *       *       *       *       *       *       *       *
GTC AAA CAT TGT GTG CCC TGC CAG GTT AAT GCT AAT CCT TCC AGA
Val Lys His Cys Val Pro Cys Gln Leu Val Asn Ala Asn Pro Ser Arg>
```

(SEQ. ID NO: 2) cont'd

```
        4040              4050              4060              4070              4080
          *                 *                 *                 *                 *
ATA CCT CCA AGA AAG AGA CTA AGG GGA AGC CAC CCA GGC GCT CAC TGG
Ile Pro Pro Arg Lys Arg Leu Arg Gly Ser His Pro Gly Ala His Trp>

4090              4100              4110              4120              4130
          *                 *                 *                 *                 *
GAA GTG GAC TTC ACT GAG GTA AAG CCG GCT AAA TAC GGA AAC AAA TAT
Glu Val Asp Phe Thr Glu Val Lys Pro Ala Lys Tyr Gly Asn Lys Tyr>

4140              4150              4160              4170
          *                 *                 *                 *
CTA TTG GTT TTT GTA GAC ACC TTT TCA GGA TGG GTA GAG GCT TAT CCT
Leu Leu Val Phe Val Asp Thr Phe Ser Gly Trp Val Glu Ala Tyr Pro>

4180              4190              4200              4210              4220
          *                 *                 *                 *                 *
ACT AAA AAA GAG ACT TCA ACC GTG GTG GCT AAG AAA ATA CTG GAG GAA
Thr Lys Lys Glu Thr Ser Thr Val Val Ala Lys Lys Ile Leu Glu Glu>

4230              4240              4250              4260              4270
          *                 *                 *                 *                 *
ATT TTT CCA AGA TTT GGA ATA CCT AAG GTA ATA GGG TCA GAC AAT GGT
Ile Phe Pro Arg Phe Gly Ile Pro Lys Val Ile Gly Ser Asp Asn Gly>
```

FIG. 2Q (SEQ. ID NO: 2) cont'd

```
          4280              4290              4300              4310              4320
            *                 *                 *                 *                 *
         CCA GCT TTC GTT GCC CAG GTA AGT CAG GGA CTG GCC AAG ATA TTG GGG
         Pro Ala Phe Val Ala Gln Val Ser Gln Gly Leu Ala Lys Ile Leu Gly>

4330              4340              4350              4360              4370        4380
            *                 *                 *                 *                 *           *
         ATT GAT TG A AAA CTG CAT TGT GCA TAC AGA CCC CAA AGC TCA GGA CAG
         Ile Asp      Lys Leu His Cys Ala Tyr Arg Pro Gln Ser Ser Gly Gln>

4380              4390              4400              4410
                     *                 *                 *                 *
         GTA GAG AGG ATG AAT AGA ACC ATT AAA GAG ACC CTT ACC AAA TTG ACC
         Val Glu Arg Met Asn Arg Thr Ile Lys Glu Thr Leu Thr Lys Leu Thr>

4420              4430              4440              4450              4460
            *                 *                 *                 *                 *
         ACA GAG ACT GGC ATT AAT GAT TGG ATG GCT CTC CTG CCC TTT GTG CTT
         Thr Glu Thr Gly Ile Asn Asp Trp Met Ala Leu Leu Pro Phe Val Leu>

4470              4480              4490              4500              4510
            *                 *                 *                 *                 *
         TTT AGG GTG AGG AAC ACC CCT GGA CAG TTT GGG CTG ACC CCC TAT AAA
         Phe Arg Val Arg Asn Thr Pro Gly Gln Phe Gly Leu Thr Pro Tyr Lys>
```

FIG. 2R (SEQ. ID NO: 2) cont'd

```
        4520        4530        4540        4550        4560
          *           *           *           *           *
TTG CTC TAC GGG GGA CCC CCG TTG GCA GAA ATT GCC TTT GCA CAT
Leu Leu Tyr Gly Gly Pro Pro Leu Ala Glu Ile Ala Phe Ala His>

4570        4580        4590        4600        4610
          *           *           *           *           *
AGT GCT GAT GTG CTG CTT TCC CAG CCT TTG TTC TCT AGG CTC AAG GCG
Ser Ala Asp Val Leu Leu Ser Gln Pro Leu Phe Ser Arg Leu Lys Ala>

4620        4630        4640        4650
          *           *           *           *
CTC GAG TGG GTG AGG CAG CGA GCG TGG AAG CAG CTC CGG GAG GCC TAC
Leu Glu Trp Val Arg Gln Arg Ala Trp Lys Gln Leu Arg Glu Ala Tyr>

4660        4670        4680        4690        4700
    *           *           *           *           *
TCA GGA GGA GAC TTG CAA GTT CCA CAT CGC TTC CAA GTT GGA GAT TCA
Ser Gly Gly Asp Leu Gln Val Pro His Arg Phe Gln Val Gly Asp Ser>

4710        4720        4730        4740        4750
    *           *           *           *           *
GTC TAT GTT AGA CGC CAC CGT GCA GGA AAC CTC GAG ACT CGG TAG AAG
Val Tyr Val Arg Arg His Arg Ala Gly Asn Leu Glu Thr Arg *** Lys>
```

FIG. 2S (SEQ. ID NO: 2) cont'd

```
     4760          4770          4780          4790          4800
       *             *             *             *             *
GGA CCT TAT CTC GTA CTT TTG ACC ACA CCA ACG GCT GTG AAA GTC GAA
Gly Pro Tyr Leu Val Leu Leu Thr Thr Pro Thr Ala Val Lys Val Glu>

4810          4820          4830          4840          4850
       *             *             *             *             *
GGA ATC CCC TTA AGC TTC GCC TCC ATC GCG TGG TTC CTT ACT CTG TCA
Gly Ile Pro Leu Ser Phe Ala Ser Ile Ala Trp Phe Leu Thr Leu Ser>

4860          4870          4880          4890          4900
       *             *             *             *             *
ATA ACT CCT CAA GTT AAT GGT AAA CGC CTT GTG GAC AGC CCG AAC TCC
Ile Thr Pro Gln Val Asn Gly Lys Arg Leu Val Asp Ser Pro Asn Ser>

4910          4920          4930          4940
       *             *             *             *
CAT AAA CCC TTA TCT CTC ACC TGG TTA CTT ACT GAC TCC GGT ACA GGT
His Lys Pro Leu Ser Leu Thr Trp Leu Leu Thr Asp Ser Gly Thr Gly>

4950          4960          4970          4980          4990
       *             *             *             *             *
ATT AAT ATT AAC AGC ACT CAA GGG GAG GCT CCC TTG GGG ACC TGG TGG
Ile Asn Ile Asn Ser Thr Gln Gly Glu Ala Pro Leu Gly Thr Trp Trp>
```

FIG. 2T (SEQ. ID NO: 2) cont'd

```
        5000            5010            5020            5030            5040
         *               *               *               *               *
CCT GAA TTA TAT GTC TGC CTT CGA ATC CCT GGT CTC AAT GAC
Pro Glu Leu Tyr Val Cys Leu Arg Ser Val Ile Pro Gly Leu Asn Asp>

5050            5060            5070            5080            5090
         *               *               *               *               *
CAG GCC ACA CCC CCC GAT GTA CTC CGT GCT TAC GGG TTT TAC GTT TGC
Gln Ala Thr Pro Pro Asp Val Leu Arg Ala Tyr Gly Phe Tyr Val Cys>

5100            5110            5120            5130
         *               *               *               *
CCA GGA CCC CCA AAT GAA GAA TAT TGT GGA AAT CCT CAG GAT TTC
Pro Gly Pro Pro Asn Glu Glu Tyr Cys Gly Asn Pro Gln Asp Phe>

5140            5150            5160            5170            5180
 *               *               *               *               *
TTT TGC AAG CAA TGG AGC TGC ATA ACT TCT AAT GAT GGG AAT TGG AAA
Phe Cys Lys Gln Trp Ser Cys Ile Thr Ser Asn Asp Gly Asn Trp Lys>

5190            5200            5210            5220            5230
 *               *               *               *               *
TGG CCA GTC TCT CAG CAA GAC AGA GTA AGT TAC TCT TTT GTT AAC AAT
Trp Pro Val Ser Gln Gln Asp Arg Val Ser Tyr Ser Phe Val Asn Asn>
```

FIG. 2U (SEQ. ID NO: 2) cont'd

```
       5240                5250                5260                5270                5280
        *                   *                   *                   *                   *
CCT ACC AGT TAT AAT CAA TTT AAT TAT GGC CAT GGG AGA TGG AAA GAT
Pro Thr Ser Tyr Asn Gln Phe Asn Tyr Gly His Gly Arg Trp Lys Asp>

5290                5300                5310                5320                5330
        *                   *                   *                   *                   *
TGG CAA CAG CGG GTA CAA AAA GAT GTA CGA AAT AAG CAA ATA AGC TGT
Trp Gln Gln Arg Val Gln Lys Asp Val Arg Asn Lys Gln Ile Ser Cys>

5340                5350                5360                5370
        *                   *                   *                   *
CAT TCG TTA GAC CTA GAT TAC TTA AAA ATA AGT TTC ACT GAA AAA GGA
His Ser Leu Asp Leu Asp Tyr Leu Lys Ile Ser Phe Thr Glu Lys Gly>

5380                5390                5400                5410                5420
        *                   *                   *                   *                   *
AAA CAA GAA AAT ATT CAA AAG TGG GTA AAT GGT ATA TCT TGG GGA ATA
Lys Gln Glu Asn Ile Gln Lys Trp Val Asn Gly Ile Ser Trp Gly Ile>

5430                5440                5450                5460                5470
        *                   *                   *                   *                   *
GTG TAC TAT GGA GGC TCT GGG AGA AAG AAA GGA AGA TCT GTT CTG ACT ATT
Val Tyr Tyr Gly Gly Ser Gly Arg Lys Lys Gly Arg Ser Val Leu Thr Ile>
```

FIG. 2V (SEQ. ID NO: 2) cont'd

```
      5480        5490        5500        5510        5520
       *           *           *           *           *
CGC CTC AGA ATA GAA ACT CAG ATG GAA CCT CCG GTT GCT ATA GGA CCA
Arg Leu Arg Ile Glu Thr Gln Met Glu Pro Pro Val Ala Ile Gly Pro>

5530        5540        5550        5560
       *           *           *           *
AAT AAG GGT TTG GCC GAA CAA GGA CCT CCA ATC CAA GAA CAG
Asn Lys Gly Leu Ala Glu Gln Gly Pro Pro Ile Gln Glu Gln>

5570        5580        5590        5600        5610
       *           *           *           *           *
AGG CCA TCT CCT AAC CCC TCT GAT TAC AAT ACA ACC TCT GGA TCA GTC
Arg Pro Ser Pro Asn Pro Ser Asp Tyr Asn Thr Thr Ser Gly Ser Val>

5620        5630        5640        5650        5660
       *           *           *           *           *
CCC ACT GAG CCT AAC ATC ACT ATT AAA ACA GGG GCG AAA CTT TTT AGC
Pro Thr Glu Pro Asn Ile Thr Ile Lys Thr Gly Ala Lys Leu Phe Ser>

5670        5680        5690        5700
       *           *           *           *
CTC ATC CAG GGA GCT TTT CAA GCT CTT AAC TCC ACG ACT CCA GAG GCT
Leu Ile Gln Gly Ala Phe Gln Ala Leu Asn Ser Thr Thr Pro Glu Ala>
```

FIG. 2W (SEQ. ID NO: 2) cont'd

```
5710        5720        5730        5740        5750
 *     *     *     *     *     *     *     *     *
ACC TCT TCT TGT TGG CTT TGC TTA GCT TCG GGC CCA CCT TAC TAT GAG
Thr Ser Ser Cys Trp Leu Cys Leu Ala Ser Gly Pro Pro Tyr Tyr Glu>

5760        5770        5780        5790        5800
 *     *     *     *     *     *     *     *     *
GGA ATG GCT AGA GGA GGG AAA TTC AAT GTG ACA AAG GAA CAT AGA GAC
Gly Met Ala Arg Gly Gly Lys Phe Asn Val Thr Lys Glu His Arg Asp>

5810        5820        5830        5840        5850
 *     *     *     *     *     *     *     *     *
CAA TGT ACA TGG GGA TCC CAA AAT AAG CTT ACC CTT ACT GAG GTT TCT
Gln Cys Thr Trp Gly Ser Gln Asn Lys Leu Thr Leu Thr Glu Val Ser>

5860        5870        5880        5890        5900
 *     *     *     *     *     *     *     *     *
GGA AAA GGC ACC TGC ATA GGG ATG GTT CCC CCA TCC CAC CAA CAC CTT
Gly Lys Gly Thr Cys Ile Gly Met Val Pro Pro Ser His Gln His Leu>

5910        5920        5930        5940
 *     *     *     *     *     *     *     *
TGT AAC CAC ACT GAA GCC TTT AAT CGA ACC TCT GAG AGT CAA TAT CTG
Cys Asn His Thr Glu Ala Phe Asn Arg Thr Ser Glu Ser Gln Tyr Leu>
```

FIG. 2X (SEQ. ID NO: 2) cont'd

```
      5950        5960        5970        5980        5990        6040
        *           *           *           *           *           *
                 GTA CCT GGT TAT GAC AGG TGG GCA TGT AAT ACT GGA TTA ACC CCT
                 Val Pro Gly Tyr Asp Arg Trp Ala Cys Asn Thr Gly Leu Thr Pro>

6000        6010        6020        6030        6040        6090
        *           *           *           *           *           *
    TGT GTT TCC ACC TTG GTT TTC AAC CAA ACT AAA GAC TTT TGC GTT ATG
    Cys Val Ser Thr Leu Val Phe Asn Gln Thr Lys Asp Phe Cys Val Met>

6050        6060        6070        6080        6130        6140
        *           *           *           *           *           *
    GTC CAA ATT GTC CCC CGG TAC TAC TAT CCC GAA AAA GCA GTC CTT
    Val Gln Ile Val Pro Arg Tyr Tyr Tyr Pro Glu Lys Ala Val Leu>

6100        6110        6120        6170        6180
        *           *           *           *           *
    GAT GAA TAT GAC TAT AGA TAT AAT CGG CCA AAA AGA GAG CCC ATA TCC
    Asp Glu Tyr Asp Tyr Arg Tyr Asn Arg Pro Lys Arg Glu Pro Ile Ser>

6150        6160
        *           *
    CTG ACA CTA GCT GTA ATG CTC GGA GTG GCT GCA GGC GTG GGA
    Leu Thr Leu Ala Val Met Leu Gly Val Ala Ala Gly Val Gly>
```

FIG. 2Y (SEQ. ID NO: 2) cont'd

```
      6190      6200      6210      6220      6230
        *         *         *         *         *
ACA GGA ACG GCT GCC CTA ATC ACA GGA CCG CAA CAG CTG GAG AAA GGA
Thr Gly Thr Ala Ala Leu Ile Thr Gly Pro Gln Gln Leu Glu Lys Gly>

6240      6250      6260      6270      6280
        *         *         *         *         *
CTT AGT AAC CTA CAT CGA ATT GTA ACG GAA GAT CTC CAA GCC CTA GAA
Leu Ser Asn Leu His Arg Ile Val Thr Glu Asp Leu Gln Ala Leu Glu>

6290      6300      6310      6320      6330
        *         *         *         *         *
AAA TCT GTC AGT AAC CTG GAG GAA TCC CTA ACC TCC TTA TCT GAA GTG
Lys Ser Val Ser Asn Leu Glu Glu Ser Leu Thr Ser Leu Ser Glu Val>

6340      6350      6360      6370      6380
        *         *         *         *         *
GTT CTA CAG AAC AGA AGG GGG TTA GAT CTG TTA TTT CTA AAA GAA GGA
Val Leu Gln Asn Arg Arg Gly Leu Asp Leu Leu Phe Leu Lys Glu Gly>

6390      6400      6410      6420
        *         *         *         *
GGG TTA TGT GTA GCC TTA AAA GAG GAA TGC TGC TTC TAT GTA GAT CAC
Gly Leu Cys Val Ala Leu Lys Glu Glu Cys Cys Phe Tyr Val Asp His>
```

FIG. 2Z (SEQ. ID NO: 2) cont'd

```
      6430        6440        6450        6460        6470
       *           *           *           *           *
TCA GGA GCC ATC AGA GAC TCC ATG AGC AAG CTT AGA GAA AGG TTA GAG
Ser Gly Ala Ile Arg Asp Ser Met Ser Lys Leu Arg Glu Arg Leu Glu>

6480        6490        6500        6510        6520
       *           *           *           *           *
AGG CGT CGA AGG GAA AGA GAG GCT GAC CAG GGG TGG TTT GAA GGA TGG
Arg Arg Arg Arg Glu Arg Glu Ala Asp Gln Gly Trp Phe Glu Gly Trp>

6530        6540        6550        6560        6570
       *           *           *           *           *
TTC AAC AGG TCT CCT TGG ATG ACC CTG CTT TCT GCT CTG ACG GGG
Phe Asn Arg Ser Pro Trp Met Thr Leu Leu Ser Ala Leu Thr Gly>

6580        6590        6600        6610        6620
       *           *           *           *           *
CCC CTA GTA GTC CTG CTC CTG TTA CTT ACA GTT GGG CCT TGC TTA ATT
Pro Leu Val Val Leu Leu Leu Leu Thr Val Gly Pro Cys Leu Ile>

6630        6640        6650        6660
       *           *           *           *
AAT AGG TTT GTT GCC TTT GTT AGA GAA CGA GTG AGT GCA GTC CAG ATC
Asn Arg Phe Val Ala Phe Val Arg Glu Arg Val Ser Ala Val Gln Ile>
```

FIG. 2AA (SEQ. ID NO: 2) cont'd

```
      6670        6680        6690        6700        6710
        *           *           *           *           *
ATG GTA CTT AGG CAA CAG TAC CAA GGC CTT CTG AGC CAA GGA GAA ACT
Met Val Leu Arg Gln Gln Tyr Gln Gly Leu Leu Ser Gln Gly Glu Thr 6720        6730        6740        6750        6760        6770
        *           *           *           *           *           *
GAC CTC TAGCCTTC CCAGTTCTAA GATTAGAACT ATTAACAAGA CAAGAAGTGG
Asp Leu>

6780        6790        6800        6810        6820        6830
        *           *           *           *           *           *
GGAATGAAAG GATGAAAATG CAACCTAACC CTCCCAGAAC CCAGGAAGTT AATAAAAAGC 6840        6850        6860        6870        6880        6890
        *           *           *           *           *           *
TCTAAATGCC CCCGAATTCC AGACCCTGCT GGCTGCCAGT AAATAGGTAG AAGGTCACAC 6900        6910        6920        6930        6940        6950
        *           *           *           *           *           *
TTCCTATTGT TCCAGGGCCT GCTATCCTGG CCTAAGTAAG ATTAACAGGA ATGAGTTGAC 6960        6970        6980        6990        7000        7010
        *           *           *           *           *           *
TAATCGCTTA TCTGGATTCT GTAAAACTGA CTGGCACCAT AGAAGAATTG ATTACACATT
```

FIG. 2AB (SEQ. ID NO: 2) cont'd

```
          7020       7030       7040       7050       7060       7070
            *          *          *          *          *          *
     GACAGCCCTA GTGACCTATC TCAACTGCAA TCTGTCACTC TGCCCAGGAG CCCAGCAGA 7080       7090       7100       7110       7120       7130
            *          *          *          *          *          *
     TGCGGACCTC CGGAGCTATT TTAAAATGAT TGGTCCACGG AGCGGGGCT CTCGATATTT 7140       7150       7160       7170       7180       7190
            *          *          *          *          *          *
     TAAAATGATT GGTCCATGGA GCGGGGCTC TCGATATTTT AAAATGATTG GTTTGTGACG 7200       7210       7220       7230       7240       7250
            *          *          *          *          *          *
     CACAGGCTTT GTTGTGAACC CCATAAAAGC TGTCCCGATT CCGCACTCGG GGCCGCAGTC 7260       7270       7280       7290       7300       7310
            *          *          *          *          *          *
     CTCTACCCCT GGGTGGGTA CGACTGTGG CCCCAGGGG CTTGGAATAA AAATCCTCTT 7320       7330
            *          *
     GCTGTTTGCA TCAAAAAAAA AAA
```

FIG. 2AC (SEQ. ID NO: 3)

```
          10         20         30         40         50         60
           *          *          *          *          *          *
    GCGTGGTGTA CGACTGTGGG CCCCAGCGCG CTTGAATAAA AAATCCTCTT GCTGTTTGCA 70         80         90        100        110        120
           *          *          *          *          *          *
    TCAAGACCGC TTTCGTGTAG TGATTAAGGG GAGTCGCCTT TTCCGAGCCT GGAGTTCTT 130        140        150        160        170        180
           *          *          *          *          *          *
    TTTGCTGGTC TTACATTTGG GGGCTCGTCC GGATCTGTC GCGGCCACCC CTAACACCCG 190        200        210        220        230        240
           *          *          *          *          *          *
    AGAACCGACT TGGAGGTAAA AAGGATCCTC TTTTTAACGT GTATGCATGT ACCGGCCGGC 250        260        270        280        290        300
           *          *          *          *          *          *
    GTCTCTGTTC TGAGTGTCTG TTTTCAGTGG TGCGGCTTT CGGTTTGCAG CTGTCCCTC 310        320        330        340        350        360
           *          *          *          *          *          *
    AGGCCGTAAG GCTGGGGGA CTGTGATCAG CAGACGTGCT AGAGGATCA CAGGCTGCTG
```

FIG. 3A (SEQ. ID NO: 3) cont'd

```
         370        380        390        400        410        420
          *          *          *          *          *          *
CCTGGGGGA CGCCCCGGGA GGTGAGGAGA GCCAGGGACG CCTGGTGGTC TCCTACTGTC 430        440        450        460        470        480
          *          *          *          *          *          *
GGTCAGAGGA CCGAATTCTG TTGCTGAAGC GAAAGCTTCC CCCTCCCGGA CCGTCCGACT 490        500        510        520        530        540
          *          *          *          *          *          *
CTTTGCCTG CTTGTGGAAG AGTGGGACG GTCACGTGTG TCTGGATCTG TTGGTTTCTG 550        560        570        580        590
          *          *          *          *          *
TTTTGTGTGT CTTTGTCTTG TGTGTCCTTG TCTACAGTTT TAAT ATG GGA CAG ACG
                                               Met Gly Gln Thr>

600        610        620        630        640
          *          *          *          *          *
GTG ACG ACC CCT CTT AGT TTG ACT CTC GAC CAT TGG ACT GAA GTT AAA
Val Thr Thr Pro Leu Ser Leu Thr Leu Asp His Trp Thr Glu Val Lys>

650        660        670        680        690
          *          *          *          *          *
TCC AGG GCT CAT AAT TTG TCA GTT CAG GTT AAG AAG GGA CCT TGG CAG
Ser Arg Ala His Asn Leu Ser Val Gln Val Lys Lys Gly Pro Trp Gln>
```

FIG. 3B (SEQ. ID NO: 3) cont'd

```
     700         710         720         730         740
      *     *     *     *     *     *     *     *     *
ACT TTC TGT GTC TCT GAA TGG CCG ACA TTC GAT GTT GGA TGG CCA TCA
Thr Phe Cys Val Ser Glu Trp Pro Thr Phe Asp Val Gly Trp Pro Ser>

750         760         770         780
      *     *     *     *     *     *     *     *
GAG GGG ACC TTT AAT TCT GAG ATT ATC CTG GCT GTT AAA GCA GTT ATT
Glu Gly Thr Phe Asn Ser Glu Ile Ile Leu Ala Val Lys Ala Val Ile>

790         800         810         820         830
  *     *     *     *     *     *     *     *     *
TTT CAG ACT GGA CCC GGC TCT CAT CCC GAT CAG GAG CCC TAT ATC CTT
Phe Gln Thr Gly Pro Gly Ser His Pro Asp Gln Glu Pro Tyr Ile Leu>

840         850         860         870         880
      *     *     *     *     *     *     *     *     *
ACG TGG CAA GAT TTG GCA GAG GAT CCT CCG CCA TGG GTT AAA CCA TGG
Thr Trp Gln Asp Leu Ala Glu Asp Pro Pro Pro Trp Val Lys Pro Trp>

890         900         910         920         930
      *     *     *     *     *     *     *     *     *
CTG AAT AAG CCA AGA AAG CCA GGT CCC CGA ATT CTG GCT CTT GGA GAG
Leu Asn Lys Pro Arg Lys Pro Gly Pro Arg Ile Leu Ala Leu Gly Glu>
```

FIG. 3C (SEQ. ID NO: 3) cont'd

```
      940         950         960         970         980
       *           *           *           *           *
AAA AAC AAA CAC TCG GCT GAG GAG AAA GTC AAG CCC TCT CCT CAT ATC TAC
Lys Asn Lys His Ser Ala Glu Glu Lys Val Lys Pro Ser Pro His Ile Tyr>

990        1000        1010        1020
       *           *           *           *
CCC GAG ATT GAG GAG CCA CCG GCT TGG CCG GAA CCC CAA TCT GTT CCC
Pro Glu Ile Glu Glu Pro Pro Ala Trp Pro Glu Pro Gln Ser Val Pro>

1030        1040        1050        1060        1070
 *           *           *           *           *
CCA CCC CCT TAT CTG GCA CAG GGT GCC GCG AGG GGA CCC TTT GCC CCT
Pro Pro Pro Tyr Leu Ala Gln Gly Ala Ala Arg Gly Pro Phe Ala Pro>

1080        1090        1100        1110        1120
       *           *           *           *           *
CCT GGA GCT CCG GCG GTG GAG GGA CCT GCT GCA GGG ACT CGG AGC CGG
Pro Gly Ala Pro Ala Val Glu Gly Pro Ala Ala Gly Thr Arg Ser Arg>

1130        1140        1150        1160        1170
       *           *           *           *           *
AGG GGC GCC ACC CCG GAG CGG ACA GAC GAG ATC GCG ACA TTA CCG CTG
Arg Gly Ala Thr Pro Glu Arg Thr Asp Glu Ile Ala Thr Leu Pro Leu>
```

FIG. 3D (SEQ. ID NO: 3) cont'd

```
              1180        1190        1200        1210        1220
                *           *           *           *           *
          CGC ACG TAC GGC CCT CCC ACA CCG GGG CAA TTG CAG CCC CTC CAG
          Arg Thr Tyr Gly Pro Pro Thr Pro Gly Gln Leu Gln Pro Leu Gln>

1230        1240        1250        1260
                *           *           *           *
          TAT TGG CCC TTT TCT GCA GAT CTC TAT AAT TGG AAA ACT AAC CAT
          Tyr Trp Pro Phe Ser Ser Ala Asp Leu Tyr Asn Trp Lys Thr Asn His>

1270        1280        1290        1300        1310
            *           *           *           *           *
          CCC CCT TTC TCG GAG GAT CCC CAA CGC CTC ACG GGG TTG GTG GAG TCC
          Pro Pro Phe Ser Glu Asp Pro Gln Arg Leu Thr Gly Leu Val Glu Ser>

1320        1330        1340        1350        1360
            *           *           *           *           *
          CTT ATG TTC TCT CAC CAG CCT ACT TGG GAT GAT TGT CAA CAG CTG CTG
          Leu Met Phe Ser His Gln Pro Thr Trp Asp Asp Cys Gln Gln Leu Leu>

1370        1380        1390        1400        1410
                *           *           *           *           *
          CAG ACA CTC TTC ACA ACC GAG GAG CGA GAG AGA ATT CTA TTA GAG GCT
          Gln Thr Leu Phe Thr Thr Glu Glu Arg Glu Arg Ile Leu Leu Glu Ala>
```

FIG. 3E (SEQ. ID NO: 3) cont'd

```
      1420      1430      1440      1450      1460
       *    *    *    *    *    *    *    *    *
AGA AAA AAT GTT CCT GGG GCC GAC GGG CGA CCC ACG CGG TTG CAA AAT
Arg Lys Asn Val Pro Gly Ala Asp Gly Arg Pro Thr Arg Leu Gln Asn>

1470      1480      1490      1500
       *    *    *    *    *    *    *    *
GAG ATT GAC ATG GGA TTT CCC TTA ACT CGC CCC GGT TGG GAC TAC AAC
Glu Ile Asp Met Gly Phe Pro Leu Thr Arg Pro Gly Trp Asp Tyr Asn>

1510      1520      1530      1540      1550
 *    *    *    *    *    *    *    *    *    *
ACG GCT GAA GGT AGG GAG AGC TTG AAA ATC TAT CGC CAG GCT CTG GTG
Thr Ala Glu Gly Arg Glu Ser Leu Lys Ile Tyr Arg Gln Ala Leu Val>

1560      1570      1580      1590      1600
       *    *    *    *    *    *    *    *    *
GCG GGT CTC CGG GGC TCA AGA CGG CCC ACT AAT TTG GCT AAG GTA
Ala Gly Leu Arg Gly Ala Ser Arg Arg Pro Thr Asn Leu Ala Lys Val>

1610      1620      1630      1640      1650
       *    *    *    *    *    *    *    *    *
AGA GAA GTG ATG CAG GGA CCG AAT GAA CCC CCC TCT GTT TTT CTT GAG
Arg Glu Val Met Gln Gly Pro Asn Glu Pro Pro Ser Val Phe Leu Glu>
```

FIG. 3F (SEQ. ID NO: 3) cont'd

```
         1660       1670       1680       1690       1700
           *          *          *          *          *
AGG CTC TTG GAA GCC TTC AGG CGG TAC ACC CCT TTT GAT CCC ACC TCA
Arg Leu Leu Glu Ala Phe Arg Arg Tyr Thr Pro Phe Asp Pro Thr Ser>

1710       1720       1730       1740
           *          *          *          *
GAG GCC CAA AAA GCC TCA GTG GCT TTG GCC TTT ATA GGA CAG TCA GCC
Glu Ala Gln Lys Ala Ser Val Ala Leu Ala Phe Ile Gly Gln Ser Ala>

1750       1760       1770       1780       1790
   *          *          *          *          *
TTG GAT ATT AGA AAG CTT CAG AGA CTG AAG GAG GCA GAG TTA CAG GAG GCT
Leu Asp Ile Arg Lys Leu Gln Arg Leu Lys Glu Gly Leu Gln Glu Ala>

1800       1810       1820       1830       1840
           *          *          *          *          *
GAG TTA CGT GAT CTA GTG AAG GAG AAA GAG GAA AAA GTA TAT TAC AAA AGG
Glu Leu Arg Asp Leu Val Lys Glu Lys Glu Glu Lys Val Tyr Tyr Lys Arg>

1850       1860       1870       1880       1890
           *          *          *          *          *
GAG ACA GAA GAA GAA AGG GAA CAA AGA GAA AAG GAA AGA GAA GAG GAA
Glu Thr Glu Glu Glu Arg Glu Gln Arg Glu Lys Glu Arg Glu Glu Glu>
```

FIG. 3G (SEQ. ID NO: 3) cont'd

```
      1900        1910        1920        1930        1940
       *           *           *           *           *
AGG GAG GAA AGA CGT AAT AAA CGG CAA GAG AAG AAT TTG ACT AAG ATC
Arg Glu Glu Arg Arg Asn Lys Arg Gln Glu Lys Asn Leu Thr Lys Ile>

1950        1960        1970        1980
       *           *           *           *
TTG GCT GCA GTG GTT GAA GGG AAA AGC AAT ACG GAA AGA GAG AGA GAT
Leu Ala Ala Val Val Glu Gly Lys Ser Asn Thr Glu Arg Glu Arg Asp>

1990        2000        2010        2020        2030
       *           *           *           *           *
TTT AGG AAA ATT AGG TCA GGC CCT AGA CAG TCA GGG AAC CTG GGC AAT
Phe Arg Lys Ile Arg Ser Gly Pro Arg Gln Ser Gly Asn Leu Gly Asn>

2040        2050        2060        2070        2080
       *           *           *           *           *
AGG ACC CCA CTC GAC AAG GAC CAA TGT GCA TAT TGT AAA GAA AGA GGA
Arg Thr Pro Leu Asp Lys Asp Gln Cys Ala Tyr Cys Lys Glu Arg Gly>

2090        2100        2110        2120        2130
       *           *           *           *           *
CAC TGG GCA AGG AAC TGC CCC AAG AAG GGA AAC AAA GGA CCA AGG ATC
His Trp Ala Arg Asn Cys Pro Lys Lys Gly Asn Lys Gly Pro Arg Ile>
```

FIG. 3H (SEQ. ID NO: 3) cont'd

```
        2140       2150       2160       2170       2180
          *          *          *          *          *
CTA GCT CTA GAA GAT AAA GAT TAGG GGAGACGGGG TTCGACCCC
Leu Ala Leu Glu Glu Asp Lys Asp>

2190       2200       2210       2220       2230       2240
          *          *          *          *          *          *
CTCCCCGAGC CCAGGTAAC TTTGAAGGTG GAGGGGCAAC CAGTTGAGTT CCTGGTTGAT 2250       2260       2270       2280       2290       2300
          *          *          *          *          *          *
ACCGGAGCGA AACATTCAGT GCTACTACAG CCATTAGGAA AACTAAAAGA TAAAAAATCC 2310       2320       2330       2340       2350
          *          *          *          *          *
TGGGTG ATG GGT GCC ACA GGG CAA CAA CAG TAT CCA TGG ACT ACC CGA AGA
       Met Gly Ala Thr Gly Gln Gln Gln Tyr Pro Trp Thr Thr Arg Arg>

2360       2370       2380       2390
          *          *          *          *
ACA GTT GAC TTG GGA GTG GGA CGG GTA ACC CAC TCG TTT CTG GTC ATA
Thr Val Asp Leu Gly Val Gly Arg Val Thr His Ser Phe Leu Val Ile>
```

FIG. 3I (SEQ. ID NO: 3) cont'd

```
       2400       2410       2420       2430       2440
         *          *          *          *          *
                 CCT GAG TGC CCA GCA CCC CTC TTA GGT AGA GAC TTA TTG ACC AAG ATG
                 Pro Glu Cys Pro Ala Pro Leu Gly Arg Asp Leu Leu Thr Lys Met>

2450       2460       2470       2480       2490
         *          *          *          *          *
       GGA GCA CAA ATT TCT TTT GAA CAA GGG AAA CCA GAA GTG TCT GCA AAT
       Gly Ala Gln Ile Ser Phe Glu Gln Gly Lys Pro Glu Val Ser Ala Asn>

2500       2510       2520       2530       2540
         *          *          *          *          *
       AAC AAA CCT ATC ACT GTG TTG ACC CTC CAA TTA GAT GAC GAA TAT CGA
       Asn Lys Pro Ile Thr Val Leu Thr Leu Gln Leu Asp Asp Glu Tyr Arg>

2550       2560       2570       2580       2590
         *          *          *          *          *
       CTA TAC TCT CCC CTA AAG GTA AAG CCT GAT CAA AAT ATA CAA TTC TGG TTG
       Leu Tyr Ser Pro Leu Lys Val Lys Pro Asp Gln Asn Ile Gln Phe Trp Leu>

2600       2610       2620       2630
         *          *          *          *
       GAA CAG TTT CCC CAA GCC TGG GCA GAA ACC GCA GGG ATG GGT TTG GCA
       Glu Gln Phe Pro Gln Ala Trp Ala Glu Thr Ala Gly Met Gly Leu Ala>
```

FIG. 3J (SEQ. ID NO: 3) cont'd

```
 2640         2650         2660         2670         2680
  *            *            *            *            *
AAG CAA GTT CCC CCA CAA GTT ATT CAA CTG AAG GCC AGT GCC ACA CCA
Lys Gln Val Pro Pro Gln Val Ile Gln Leu Lys Ala Ser Ala Thr Pro>

2690         2700         2710         2720         2730
  *            *            *            *            *
GTG TCA GTC AGA CAG TAC CCC TTG AGT AAA GAA GCT CAA GAA GGA ATT
Val Ser Val Arg Gln Tyr Pro Leu Ser Lys Glu Ala Gln Glu Gly Ile>

2740         2750         2760         2770         2780
  *            *            *            *            *
CGG CCG CAT GTC CAA AGA TTA ATC CAA CAG GGC ATC CTA GTT CCT GTC
Arg Pro His Val Gln Arg Leu Ile Gln Gln Gly Ile Leu Val Pro Val>

2790         2800         2810         2820         2830
  *            *            *            *            *
CAA TCT CCC TGG AAT ACT CCC CTG CTA CCG GTT AGA AAG CCT GGG ACT
Gln Ser Pro Trp Asn Thr Pro Leu Leu Pro Val Arg Lys Pro Gly Thr>

2840         2850         2860         2870
  *            *            *            *
AAT GAC TAT CGA CCA GTA CAG GAC TTG AGA GAG GTC AAT AAA CGG GTG
Asn Asp Tyr Arg Pro Val Gln Asp Leu Arg Glu Val Asn Lys Arg Val>
```

FIG. 3K (SEQ. ID NO: 3) cont'd

```
         2880       2890       2900       2910       2920
           *          *          *          *          *
                    CAG GAT ATA CAC CCA ACA GTC CCG AAC CCT TAT AAC CTC TTG TGT GCT
                    Gln Asp Ile His Pro Thr Val Pro Asn Pro Tyr Asn Leu Leu Cys Ala>

2930       2940       2950       2960       2970
           *          *          *          *          *
        CTC CCA CCC CAA CGG AGC TGG TAT ACA GTA TTG GAC TTA AAG GAT GCC
        Leu Pro Pro Gln Arg Ser Trp Tyr Thr Val Leu Asp Leu Lys Asp Ala>

2980       2990       3000       3010       3020
           *          *          *          *          *
        TTC TTC TGC CTG AGA TTA CAC CCC ACT AGC CAA CCA CTT TTT GCC TTC
        Phe Phe Cys Leu Arg Leu His Pro Thr Ser Gln Pro Leu Phe Ala Phe>

3030       3040       3050       3060       3070
           *          *          *          *          *
        GAA TGG AGA GAT CCA GGT ACG GGA AGA ACC GGG CAG CTC ACC TGG ACC
        Glu Trp Arg Asp Pro Gly Thr Gly Arg Thr Gly Gln Leu Thr Trp Thr>

3080       3090       3100       3110
           *          *          *          *
        CGA CTG CCC CAA GGG TTC AAG AAC TCC CCG ACC ATC TTT GAC GAA GCC
        Arg Leu Pro Gln Gly Phe Lys Asn Ser Pro Thr Ile Phe Asp Glu Ala>
```

FIG. 3L (SEQ. ID NO: 3) cont'd

```
3120        3130           3140           3150           3160
 *    *      *       *      *       *      *       *      *       *
     CTA CAC AGA GAC CTG GCC AAC TTC AGG ATC CAA CAC CCT CAG GTG ACC
     Leu His Arg Asp Leu Ala Asn Phe Arg Ile Gln His Pro Gln Val Thr>

3170        3180           3190           3200           3210
 *    *      *       *      *       *      *       *      *       *
     CTC CTC CAG TAC GTG GAT GAC CTG CTT CTG GCG GGA ACC AAA CAG
     Leu Leu Gln Tyr Val Asp Asp Leu Leu Leu Ala Gly Ala Thr Lys Gln>

3220        3230           3240           3250           3260
 *    *      *       *      *       *      *       *      *       *
     GAC TGC TTA GAA GCC ACG AAG GCA CTA CTG CTG GAA TTG TCT GAC CTA
     Asp Cys Leu Glu Ala Thr Lys Ala Leu Leu Leu Glu Leu Ser Asp Leu>

3270        3280           3290           3300           3310
 *    *      *       *      *       *      *       *      *       *
     GGC TAC AGA GCC TCT GCT AAG AAG GCC CAG ATT TGC AGG AGA GAG GTA
     Gly Tyr Arg Ala Ser Ala Lys Lys Ala Gln Ile Cys Arg Arg Glu Val>

3320        3330           3340           3350
 *    *      *       *      *       *      *       *
     ACA TAC TTG GGG TAC AGT TTG CGG GAC GGG CAG TGG CTG ACG GAG
     Thr Tyr Leu Gly Tyr Ser Leu Arg Asp Gly Gln Arg Trp Leu Thr Glu>
```

FIG. 3M (SEQ. ID NO: 3) cont'd

```
      3360        3370        3380        3390        3400
        *           *           *           *           *
GCA CGG AAG AAA ACT GTA GTC CAG ATA CCG GCC CCA ACC ACA GCC AAA
Ala Arg Lys Lys Thr Val Val Gln Ile Pro Ala Pro Thr Thr Ala Lys>

3410        3420        3430        3440        3450
        *           *           *           *           *
CAA ATG AGA GAG TTT TTG GGG ACA GCT GGA TTT TGC AGA CTG TGG ATC
Gln Met Arg Glu Phe Leu Gly Thr Ala Gly Phe Cys Arg Leu Trp Ile>

3460        3470        3480        3490        3500
        *           *           *           *           *
CCG GGG TTT GCG ACC TTA GCA GCC CCA CTC TAC CCG CTA ACC AAA GAA
Pro Gly Phe Ala Thr Leu Ala Ala Pro Leu Tyr Pro Leu Thr Lys Glu>

3510        3520        3530        3540        3550
        *           *           *           *           *
AAA GGG GAA TTC TCC TGG GCT CCT GAG CAC CAG AAG GCA TTT GAT GCT
Lys Gly Glu Phe Ser Trp Ala Pro Glu His Gln Lys Ala Phe Asp Ala>

3560        3570        3580        3590
        *           *           *           *
ATC AAA AAG GCC CTG CTG AGC GCA CCT GCT CTG GCC CTC CCT GAC GTA
Ile Lys Lys Ala Leu Leu Ser Ala Pro Ala Leu Ala Leu Pro Asp Val>
```

FIG. 3N (SEQ. ID NO: 3) cont'd

```
3600        3610        3620        3630        3640
  *           *           *           *           *
ACT AAA CCC TTT ACC CTT TAT GTG GAT GAG CGT AAG GGA GTA GCC CGG
Thr Lys Pro Phe Thr Leu Tyr Val Asp Glu Arg Lys Gly Val Ala Arg>

3650        3660        3670        3680        3690
  *           *           *           *           *
GGA GTT TTA ACC CAA ACC CTA GGA CCA TGG AGA AGA CCT GTC GCC TAC
Gly Val Leu Thr Gln Thr Leu Gly Pro Trp Arg Arg Pro Val Ala Tyr>

3700        3710        3720        3730        3740
  *           *           *           *           *
CTG TCA AAG AAG CTC GAT CCT GTA GCC AGT GGT TGG CCC ATA TGC CTG
Leu Ser Lys Lys Leu Asp Pro Val Ala Ser Gly Trp Pro Ile Cys Leu>

3750        3760        3770        3780        3790
  *           *           *           *           *
AAG GCT ATC GCA GCT GTG GCC ATA CTG GTC AAG GAC GCT GAC AAA TTG
Lys Ala Ile Ala Ala Val Ala Ile Leu Val Lys Asp Ala Asp Lys Leu>

3800        3810        3820        3830
  *           *           *           *
ACT TTG GGA CAG AAT ATA ACT GTA ATA GCC CCC CAT GCA TTG GAG AAC
Thr Leu Gly Gln Asn Ile Thr Val Ile Ala Pro His Ala Leu Glu Asn>
```

FIG. 3O (SEQ. ID NO: 3) cont'd

```
     3840              3850              3860              3870              3880
       *                 *                 *                 *                 *
     ATC GTT CGG CAG CCC CCA GAC CGA TGG ATG ACC AAC GCC CGC ATG ACC
     Ile Val Arg Gln Pro Pro Asp Arg Trp Met Thr Asn Ala Arg Met Thr>

3890              3900              3910              3920              3930
       *                 *                 *                 *                 *
     CAC TAT CAA AGC CTG CTC ACA GAG AGG GTC ACG TTC GCT CCA CCA
     His Tyr Gln Ser Leu Leu Thr Glu Arg Val Thr Phe Ala Pro Pro>

3940              3950              3960              3970              3980
       *                 *                 *                 *                 *
     GCC GCT CTC AAC CCT GCC ACT CTT CTG CCT GAA GAG ACT GAT GAA CCA
     Ala Ala Leu Asn Pro Ala Thr Leu Leu Pro Glu Glu Thr Asp Glu Pro>

3990              4000              4010              4020              4030
       *                 *                 *                 *                 *
     GTG ACT CAT GAT TGC CAT CAA CTA TTG ATT GAG GAG ACT GGG GTC CGC
     Val Thr His Asp Cys His Gln Leu Leu Ile Glu Glu Thr Gly Val Arg>

4040              4050              4060              4070
       *                 *                 *                 *
     AAG GAC CTT ACA GAC ATA CCG CTG ACT GGA GAA GTG CTA ACC TGG TTC
     Lys Asp Leu Thr Asp Ile Pro Leu Thr Gly Glu Val Leu Thr Trp Phe>
```

FIG. 3P (SEQ. ID NO: 3) cont'd

```
    4080              4090            4100            4110            4120
      *                 *               *               *               *
           ACT GAC GGA AGC AGC TAT GTG GTG GAA GGT AAG AGG ATG GCT GGG GCG
           Thr Asp Gly Ser Ser Tyr Val Val Glu Gly Lys Arg Met Ala Gly Ala>

4130              4140            4150            4160            4170
      *                 *               *               *               *
           GCG GTG GAC GGG ACC CGC ACG ATC TGG GCC AGC CTG CCG GAA
           Ala Val Asp Gly Thr Arg Thr Ile Trp Ala Ser Ser Leu Pro Glu>

4180              4190            4200            4210            4220
      *                 *               *               *               *
           GGA ACT TCA GCA CAA AAG GCT GAG CTC ATG GCC CTC ACG CAA GCT TTG
           Gly Thr Ser Ala Gln Lys Ala Glu Leu Met Ala Leu Thr Gln Ala Leu>

4230              4240            4250            4260            4270
      *                 *               *               *               *
           CGG CTG GCC GAA GGG AAA TCC ATA AAC ATT TAT ACG GAC AGC AGG TAT
           Arg Leu Ala Glu Gly Lys Ser Ile Asn Ile Tyr Thr Asp Ser Arg Tyr>

4280              4290            4300            4310
      *                 *               *               *
           GCC TTT GCG ACT GCA CAC GTA CAT GGG GCC ATC TAT AAA CAA AGG GGG
           Ala Phe Ala Thr Ala His Val His Gly Ala Ile Tyr Lys Gln Arg Gly>
```

FIG. 3Q (SEQ. ID NO: 3) cont'd

```
         4330          4340          4350          4360
  *        *     *       *     *       *     *       *     *
TTG CTT ACC TCA GCA GGG AGG GAA ATA AAG AAC AAA GAG GAA ATT CTA
Leu Leu Thr Ser Ala Gly Arg Glu Ile Lys Asn Lys Glu Glu Ile Leu⟩

4370          4380          4390          4400          4410
  *        *     *       *     *       *     *       *     *       *
AGC CTA TTA GAA GCC GTA CAT TTA CCA AAA AGG CTA GCT ATT ATA CAC
Ser Leu Leu Glu Ala Val His Leu Pro Lys Arg Leu Ala Ile Ile His⟩

4420          4430          4440          4450          4460
  *        *     *       *     *       *     *       *     *       *
TGT CCT GGA CAT CAG AAA GCT AAA GAT CTC ATA TCC AGA GGA AAC CAG
Cys Pro Gly His Gln Lys Ala Lys Asp Leu Ile Ser Arg Gly Asn Gln⟩

4470          4480          4490          4500          4510
  *        *     *       *     *       *     *       *     *       *
ATG GCT GAC CGG GTT GCC AAG CAG GCA GCC CAG GGT GTT AAC CTT CTG
Met Ala Asp Arg Val Ala Lys Gln Ala Ala Gln Gly Val Asn Leu Leu⟩

4520          4530          4540          4550
  *        *     *       *     *       *     *       *
CCT ATA ATA GAA ATG CCC AAA GCC CCA GAA CCC AGA CGA CAG TAC ACC
Pro Ile Ile Glu Met Pro Lys Ala Pro Glu Pro Arg Arg Gln Tyr Thr⟩
```

FIG. 3R (SEQ. ID NO: 3) cont'd

```
     4560           4570           4580           4590           4600
       *              *              *              *              *
              CTA GAA GAC TGG CAA GAG ATA AAA AAG ATA GAC CAG TTC TCT GAG ACT
              Leu Glu Asp Trp Gln Glu Ile Lys Lys Ile Asp Gln Phe Ser Glu Thr>

4610           4620           4630           4640           4650
       *              *              *              *              *
              CCG GAA GGG ACC TGC TAT ACC TCA GAT GGG AAG GAA ATC CTG CCC CAC
              Pro Glu Gly Thr Cys Tyr Thr Ser Asp Gly Lys Glu Ile Leu Pro His>

4660           4670           4680           4690           4700
       *              *              *              *              *
              AAA GAA GGG TTA GAA TAT GTC CAA CAG ATA CAT CGT CTA ACC CAC CTA
              Lys Glu Gly Leu Glu Tyr Val Gln Gln Ile His Arg Leu Thr His Leu>

4710           4720           4730           4740           4750
       *              *              *              *              *
              GGA ACT AAA CAC CTG CAG CAG TTG GTC AGA ACA TCC CCT TAT CAT GTT
              Gly Thr Lys His Leu Gln Gln Leu Val Arg Thr Ser Pro Tyr His Val>

4760           4770           4780           4790
       *              *              *              *
              CTG AGG CTA CCA GGA GTC GCT GAC TCG GTG GTC AAA CAT TGT GTG CCC
              Leu Arg Leu Pro Gly Val Ala Asp Ser Val Val Lys His Cys Val Pro>
```

FIG. 3S (SEQ. ID NO: 3) cont'd

```
       4810        4820        4830        4840
4800    *     *     *     *     *     *     *     *
TGC CAG CTG GTT AAT GCT AAT CCT TCC AGA ATG CCT CCA GGG AAG AGA
Cys Gln Leu Val Asn Ala Asn Pro Ser Arg Met Pro Pro Gly Lys Arg>

4860        4870        4880        4890
4850    *     *     *     *     *     *     *     *
CTA AGG GGA AGC CAC CCA GGC GCT CAC TGG GAA GTG GAC TTC ACT GAG
Leu Arg Gly Ser His Pro Gly Ala His Trp Glu Val Asp Phe Thr Glu>

4910        4920        4930        4940
4900    *     *     *     *     *     *     *     *
GTA AAG CCG GCT AAA TAC GGA AAC AAA TAC CTA TTG GTT TTT GTA GAC
Val Lys Pro Ala Lys Tyr Gly Asn Lys Tyr Leu Leu Val Phe Val Asp>

4960        4970        4980        4990
4950    *     *     *     *     *     *     *     *
ACC TTT TCA GGA TGG GTA GAG GCT TAT CCT ACT AAG AAA GAG ACT TCA
Thr Phe Ser Gly Trp Val Glu Ala Tyr Pro Thr Lys Lys Glu Thr Ser>

5010        5020        5030
5000    *     *     *     *     *     *     *     *
ACC GTG GCT AAA AAA ATA CTG GAA GAA ATT TTT CCA AGA TTT GGA
Thr Val Ala Lys Lys Ile Leu Glu Glu Ile Phe Pro Arg Phe Gly>
```

FIG. 3T (SEQ. ID NO: 3) cont'd

```
       5040        5050        5060        5070        5080
         *           *           *           *           *
       ATA CCT AAG GTA ATA GGG TCA GAC AAT GGT CCA GCT TTT GTT GCC CAC
       Ile Pro Lys Val Ile Gly Ser Asp Asn Gly Pro Ala Phe Val Ala Gln>

5090        5100        5110        5120        5130
         *           *           *           *           *
       GTA AGT CAG GGA CTG GCC AAG ATA TTG GGG ATT GAT TGG AAA CTG CAT
       Val Ser Gln Gly Leu Ala Lys Ile Leu Gly Ile Asp Trp Lys Leu His>

5140        5150        5160        5170        5180
         *           *           *           *           *
       TGT GCA TAC AGA CCC CAA AGC TCA GGA CAG CAG GTA GAG AGG ATG AAT AGA
       Cys Ala Tyr Arg Pro Gln Ser Ser Gly Gln Val Glu Arg Met Asn Arg>

5190        5200        5210        5220        5230
         *           *           *           *           *
       ACC ATT AAA GAG ACC CTT ACT AAA TTG ACC GCG GAG ACT GGC GTT AAT
       Thr Ile Lys Glu Thr Leu Thr Lys Leu Thr Ala Glu Thr Gly Val Asn>

5240        5250        5260        5270
         *           *           *           *
       GAT TGG ATA GCT CTC CTG CCC TTT GTG CTT TTT AGG GTT AGG AAC ACC
       Asp Trp Ile Ala Leu Leu Pro Phe Val Leu Phe Arg Val Arg Asn Thr>
```

FIG. 3U (SEQ. ID NO: 3) cont'd

```
         5280            5290            5300            5310            5320
           *               *               *               *               *
                         CCT GGA CAG TTT GGG CTG ACC CCC TAT GAA TTA CTC TAC GGG GGA CCC
                         Pro Gly Gln Phe Gly Leu Thr Pro Tyr Glu Leu Leu Tyr Gly Gly Pro>

5330            5340            5350            5360            5370
           *               *               *               *               *
         CCC CCA TTG GTA GAA ATT GCT TCT GTA CAT AGT GCT GAC GTG CTG CTT
         Pro Pro Leu Val Glu Ile Ala Ser Val His Ser Ala Asp Val Leu Leu>

5380            5390            5400            5410            5420
           *               *               *               *               *
         TCC CAG CCT TTG TTC TCT AGG CTC AAG GCA CTT GAG TGG GTG AGA CAA
         Ser Gln Pro Leu Phe Ser Arg Leu Lys Ala Leu Glu Trp Val Arg Gln>

5430            5440            5450            5460            5470
           *               *               *               *               *
         CGA GCG TGG AGG CAA CTC CGG GAG GCC TAC TCA GGA GGA GAC TTG
         Arg Ala Trp Arg Gln Leu Arg Glu Ala Tyr Ser Gly Gly Asp Leu>

5480            5490            5500            5510
           *               *               *               *
         CAG ATC CCA CAT CGT TTC CAA GTG GGA GAT TCA GTC TAC GTT AGA CGC
         Gln Ile Pro His Arg Phe Gln Val Gly Asp Ser Val Tyr Val Arg Arg>
```

FIG. 3V (SEQ. ID NO: 3) cont'd

```
          5520          5530          5540          5550          5560
            *             *             *             *             *
          CAC CGT GCA GGA AAC CTC GAG ACT CGG TGG AAG GGC CCT TAT CTC GTA
          His Arg Ala Gly Asn Leu Glu Thr Arg Trp Lys Gly Pro Tyr Leu Val>

5570          5580          5590          5600          5610
            *             *             *             *             *
          CTT TTG ACC ACA CCA ACG GCT GTG AAA GTC GAA GGA ATC TCC ACC TGG
          Leu Leu Thr Thr Pro Thr Ala Val Lys Val Glu Gly Ile Ser Thr Trp>

5620          5630          5640          5650          5660
            *             *             *             *             *
          ATC CAT GCA TCC CAC GTT AAA CCG CGG CCA CCT CCC GAT TCG GGG TGG
          Met His Pro Thr Leu Asn Arg Arg His Leu Pro Ile Arg Gly Gly>

Ile His Ala Ser His Val Lys Pro Ala Pro Pro Asp Ser Gly Trp>

5670          5680          5690          5700          5710
            *             *             *             *             *
          AAA GCC GAA AAG ACT GAA AAT CCC CTT AAG CTT CGC CTC CAT CGC GTG
          Lys Pro Lys Arg Leu Lys Ile Pro Leu Ser Phe Ala Ser Ile Ala Trp>

Lys Ala Glu Lys Thr Glu Asn Pro Leu Lys Leu Arg Leu His Arg Val>
```

FIG. 3W

(SEQ. ID NO: 3) cont'd

```
          5720          5730          5740          5750          5760
            *             *             *             *             *
GTT CCT TAC TCT GTC AAT AAC CTC TCA GAC T AAT GGT ATG CGC ATA GGA
Phe Leu Thr Leu Ser Ile Thr Ser Gln Thr  Asn Gly Met Arg Ile Gly>

Val Pro Tyr Ser Val Asn Asn Leu Ser Asp>

5770          5780          5790          5800
            *             *             *             *
GAC AGC CTG AAC TCC CAT AAA CCC TTA TCT CTC ACC TGG TTA ATT ACT
Asp Ser Leu Asn Ser His Lys Pro Leu Ser Leu Thr Trp Leu Ile Thr>

5810          5820          5830          5840          5850
            *             *             *             *             *
GAC TCC GGC ACA GGT ATT AAT ATC AAC AAC ACT CAA GGG GAG GCT CCT
Asp Ser Gly Thr Gly Ile Asn Ile Asn Asn Thr Gln Gly Glu Ala Pro>

5860          5870          5880          5890          5900
            *             *             *             *             *
TTA GGA ACC TGG TGG CCT GAT CTA TAC GTT TGC CTC AGA TCA GTT ATT
Leu Gly Thr Trp Trp Pro Asp Leu Tyr Val Cys Leu Arg Ser Val Ile>

5910          5920          5930          5940          5950
            *             *             *             *             *
CCT AGT CTG ACC TCA CCC CCA GAT ATC CTC CAT GCT CAC GGA TTT TAT
Pro Ser Leu Thr Ser Pro Pro Asp Ile Leu His Ala His Gly Phe Tyr>
```

FIG. 3X (SEQ. ID NO: 3) cont'd

```
        5960          5970          5980          5990          6000
          *             *             *             *             *
GTT TGC CCA GGA CCA AAT AAT GGA AAA CAT TGC GGA AAT CCC AGA
Val Cys Pro Gly Pro Asn Asn Gly Lys His Cys Gly Asn Pro Arg>

6010          6020          6030          6040
          *             *             *             *
GAT TTC TTT TGT AAA CAA TGG AAC TGT GTA ACC TCT AAT GAT GGA TAT
Asp Phe Phe Cys Lys Gln Trp Asn Cys Val Thr Ser Asn Asp Gly Tyr>

6050          6060          6070          6080          6090
          *             *             *             *             *
TGG AAA TGG CCA ACC AGC TCT CAG CAG GAT AGG GTA AGT TTT TCT TAT GTC
Trp Lys Trp Pro Thr Ser Gln Gln Asp Arg Val Ser Phe Ser Tyr Val>

6100          6110          6120          6130          6140
          *             *             *             *             *
AAC ACC TAT ACC AGC TCT GGA CAA TTT AAT TAC CTG ACC TGG ATT AGA
Asn Thr Tyr Thr Ser Ser Gly Gln Phe Asn Tyr Leu Thr Trp Ile Arg>

6150          6160          6170          6180          6190
          *             *             *             *             *
ACT GGA AGC CCC AAG TGC TCT CCT TCA GAC CTA GAT TAC CTA AAA ATA
Thr Gly Ser Pro Lys Cys Ser Pro Ser Asp Leu Asp Tyr Leu Lys Ile>
```

FIG. 3Y (SEQ. ID NO: 3) cont'd

```
          6200            6210            6220            6230            6240
            *               *               *               *               *
        AGT TTC ACT GAG AAA GGA AAA CAA GAA AAT ATC CTA AAA TGG GTA AAT
        Ser Phe Thr Glu Lys Gly Lys Gln Glu Asn Ile Leu Lys Trp Val Asn>

6250            6260            6270            6280
            *               *               *               *
        GGT ATG TCT TGG GGA ATG GTA TAT TAT GGA GGC TCG GGT AAA CAA CCA
        Gly Met Ser Trp Gly Met Val Tyr Tyr Gly Gly Ser Gly Lys Gln Pro>

6290           6300            6310            6320            6330
   *              *               *               *               *
        GGC TCC ATT CTA ACT ATT CGC CTC AAA ATA AAC CAG CTG GAG CCT CCA
        Gly Ser Ile Leu Thr Ile Arg Leu Lys Ile Asn Gln Leu Glu Pro Pro>

6340            6350            6360            6370            6380
            *               *               *               *               *
        ATG GCT ATA GGA CCA AAT ACG GTC TTG ACG GGT CAA AGA CCC CCA ACC
        Met Ala Ile Gly Pro Asn Thr Val Leu Thr Gly Gln Arg Pro Pro Thr>

6390            6400            6410            6420            6430
            *               *               *               *               *
        CAA GGA CCA GGA CCA TCC TCT AAC ATA ACT TCT GGA TCA GAC CCC ACT
        Gln Gly Pro Gly Pro Ser Ser Asn Ile Thr Ser Gly Ser Asp Pro Thr>
```

FIG. 3Z (SEQ. ID NO: 3) cont'd

```
        6440            6450            6460            6470            6480
          *               *               *               *               *
GAG TCT AAC AGC ACG ACT AAA ATG GGG GCA AAA CTT TTT AGC CTC ATC
Glu Ser Asn Ser Thr Thr Lys Met Gly Ala Lys Leu Phe Ser Leu Ile>

6490            6500            6510            6520
          *               *               *               *
CAG GGA GCT TTT CAA GCT CTT AAC TCC ACG ACT CCA GAG GCT ACC TCT
Gln Gly Ala Phe Gln Ala Leu Asn Ser Thr Thr Pro Glu Ala Thr Ser>

6530            6540            6550            6560            6570
  *               *               *               *               *
TCT TGT TGG CTA TGC TTA GCT TCG GGC CCA CCT TAC TAT GAA GGA ATG
Ser Cys Trp Leu Cys Leu Ala Ser Gly Pro Pro Tyr Tyr Glu Gly Met>

6580            6590            6600            6610            6620
  *               *               *               *               *
GCT AGA AGA GGG AAA TTC AAT GTG ACA AAA GAA CAT AGA GAC CAA TGC
Ala Arg Arg Gly Lys Phe Asn Val Thr Lys Glu His Arg Asp Gln Cys>

6630            6640            6650            6660            6670
  *               *               *               *               *
ACA TGG GGA TCC CAA AAT AAG CTT ACC CTT ACT GAG GTT TCT GGA AAA
Thr Trp Gly Ser Gln Asn Lys Leu Thr Leu Thr Glu Val Ser Gly Lys>
```

FIG. 3AA (SEQ ID NO: 3) cont'd

```
           6680        6690        6700        6710        6720
             *           *           *           *           *
GGC ACC TGC ATA GGA AAG GTT CCC CCA TCC CAC CAA CAC CTT TGT AAC
Gly Thr Cys Ile Gly Lys Val Pro Pro Ser His Gln His Leu Cys Asn>

6730        6740        6750        6760
             *           *           *           *
CAC ACT GAA GCC TTT AAT CAA ACC TCT GAG AGT CAA TAT CTG GTA CCT
His Thr Glu Ala Phe Asn Gln Thr Ser Glu Ser Gln Tyr Leu Val Pro>

6770        6780        6790        6800        6810
   *           *           *           *           *
GGT TAT GAC AGG TGG GCA TGT AAT ACT GGA TTA ACC CCT TGT GTT
Gly Tyr Asp Arg Trp Trp Ala Cys Asn Thr Gly Leu Thr Pro Cys Val>

6820        6830        6840        6850        6860
             *           *           *           *           *
TCC ACC TTG GTT TTT AAC CAA ACT AAA GAT TTT TGC ATT ATG GTC CAA
Ser Thr Leu Val Phe Asn Gln Thr Lys Asp Phe Cys Ile Met Val Gln>

6870        6880        6890        6900        6910
             *           *           *           *           *
ATT GTT CCC CGA GTG TAT TAC TAT CCC GAA AAA GCA ATC CTT GAT GAA
Ile Val Pro Arg Val Tyr Tyr Tyr Pro Glu Lys Ala Ile Leu Asp Glu>
```

FIG. 3AB (SEQ. ID NO: 3) cont'd

```
       6920      6930      6940      6950      6960
        *         *         *         *         *
TAT GAC TAC AGA AAT CAT CGA CAA AAG AGA GAA CCC ATA TCT CTG ACA
Tyr Asp Tyr Arg Asn His Arg Gln Lys Arg Glu Pro Ile Ser Leu Thr>

6970      6980      6990      7000
        *         *         *         *
CTT GCT GTG ATG CTC GGA CTT GGA GTG GCA GCA GGT GTA GGA ACA GGA
Leu Ala Val Met Leu Gly Leu Gly Val Ala Ala Gly Val Gly Thr Gly>

7010      7020      7030      7040      7050
  *         *         *         *         *
ACA GCT GCC CTG GTC ACG GGA CCA CAG CAG CTA GAA ACA GGA CTT AGT
Thr Ala Ala Leu Val Thr Gly Pro Gln Gln Leu Glu Thr Gly Leu Ser>

7060      7070      7080      7090      7100
        *         *         *         *         *
AAC CTA CAT CGA ATT GTA ACA GAA GAT CTC CAA GCC CTA GAA AAA TCT
Asn Leu His Arg Ile Val Thr Glu Asp Leu Gln Ala Leu Glu Lys Ser>

7110      7120      7130      7140      7150
  *         *         *         *         *
GTC AGT AAC CTG GAG GAA TCC CTA ACC TCC TTA TCT GAA GTA GTC CTA
Val Ser Asn Leu Glu Glu Ser Leu Thr Ser Leu Ser Glu Val Val Leu>
```

FIG. 3AC (SEQ. ID NO: 3) cont'd

```
       7160           7170           7180           7190           7200
         *              *              *              *              *
CAG AAT AGA AGA GGG TTA GAT TTA TTA TTT CTA AAA GAA GGA GGA TTA
Gln Asn Arg Arg Gly Leu Asp Leu Leu Phe Leu Lys Glu Gly Gly Leu>

7210           7220           7230           7240
         *              *              *              *
TGT GTA GCC TTG AAG GAG GAA TGC TGT TTT TAT GTG GAT CAT TCA GGG
Cys Val Ala Leu Lys Glu Glu Cys Cys Phe Tyr Val Asp His Ser Gly>

7250           7260           7270           7280           7290
  *              *              *              *              *
GCC ATC AGA GAC TCC ATG AAC AAG CTT AGA GAA AGG TTG GAC AAG CGT
Ala Ile Arg Asp Ser Met Asn Lys Leu Arg Glu Arg Leu Asp Lys Arg>

7300           7310           7320           7330           7340
         *              *              *              *              *
CGA AGG GAA AAG GAA ACT ACT CAA GGG TGG TTT GAG TGG TTC AAC
Arg Arg Glu Lys Glu Thr Thr Gln Gly Trp Phe Glu Gly Trp Phe Asn>

7350           7360           7370           7380           7390
         *              *              *              *              *
AGG TCT CTT TGG TTG GCT ACC CTA CTT TCT GCT TTA ACA GGA CCC TTA
Arg Ser Leu Trp Leu Ala Thr Leu Leu Ser Ala Leu Thr Gly Pro Leu>
```

FIG. 3AD (SEQ. ID NO: 3) cont'd

```
              7450      7460      7470      7480
                *         *         *         *
      TTA ATT GCC TTC ATT AGA GAA CGA ATA AGT GCA GTC CAG ATC ATG GTA
      Leu Ile Ala Phe Ile Arg Glu Arg Ile Ser Ala Val Gln Ile Met Val>

7490      7500      7510      7520      7530
     *         *         *         *         *
   CTT AGA CAA CAG TAC CAA AGC CCG TCT AGC AGG GAA GCT GGC CGC
   Leu Arg Gln Gln Tyr Gln Ser Pro Ser Ser Arg Glu Ala Gly Arg>

7540      7550      7560      7570      7580      7590
       *         *         *         *         *         *
   TAGCTCT ACCAGTCTA AGATTAGAAC TATTAACAAG AGAAGAAGTG GGAATGAAA 7600      7610      7620      7630      7640      7650
     *         *         *         *         *         *
   GGATGAAAAT ACAACCTAAG CTAATGAGAA GCTTAAAATT GTTCTGAATT CCAGAGTTTG 7660      7670      7680      7690      7700      7710
     *         *         *         *         *         *
   TTCCTTATAG GTAAAGATT AGTTTTTG CGTTTTAAA ATATGCGGAA GTAAAATAGG 7720      7730      7740      7750      7760      7770
     *         *         *         *         *         *
   CCCTGAGTAC ATGTCTCTAG GCATGAAACT TCTTGAAACT ATTTGAGATA ACAAGAAAAG
```

FIG. 3AE (SEQ. ID NO: 3) cont'd

```
        7780       7790       7800       7810       7820       7830
         *          *          *          *          *          *
GGAGTTTCTA ACTGCTTGTT TAGCTTCTGT AAAACTGGTT GCGCCATAAA GATGTTGAAA 7840       7850       7860       7870       7880       7890
         *          *          *          *          *          *
TGTTGATACA CATATCTTGG TGACAACATG TCTCCCCCAC CCGAAACAT GGGCAAATGT 7900       7910       7920       7930       7940       7950
         *          *          *          *          *          *
GTAACTCTAA AACAATTTAA ATTAATTGGT CCACGAAGCG CGGGCTCTCG AAGTTTTAAA 7960       7970       7980       7990       8000       8010
         *          *          *          *          *          *
TTGACTGGTT TGTGATATTT TGAAATGATT GGTTTGTAAA GCGCGGGCTT TGTTGTGAAC 8020       8030       8040       8050       8060       8070
         *          *          *          *          *          *
CCCATAAAAG CTGTCCGGAC TCCACACTCG GGGCCGCAGT CCTCTACCCC TGCGTGGTGT 8080       8090       8100       8110       8120       8130
         *          *          *          *          *          *
ACGACTGTGG GCCCAGCGC GCTTGGAATA AAAATCCTCT TGCTGTTTGC ATCAAAAAAA
```

FIG. 3AF

SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
       (A) LENGTH: 8060 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
CTCGAGACTC GGTGGAAGGG CCCTTATCTC GTACTTTTGA CCACACCAAC GGCTGTGAAA      60
GTCGAAGGAA TCTCCACCTG GATCCATGCA TCCCACGTTA AGCCGGCGCC ACCTCCCGAT     120
TCGGGGTGGA AAGCCGAAAA GACTGAAAAT CCCCTTAAGC TTCGCCTCCA TCGCGTGGTT     180
CCTTACTCTG TCAATAACCT CTCAGACTAA TGGTATGCGC ATAGGAGACA GCCTGAACTC     240
CCATAAACCC TTATCTCTCA CCTGGTTAAT TACTGACTCC GGCACAGGTA TTAATATCAA     300
CAACACTCAA GGGGAGGCTC CTTTAGGAAC CTGGTGGCCT GATCTATACG TTTGCCTCAG     360
ATCAGTTATT CCTAGTCTGA CCTCACCCCC AGATATCCTC CATGCTCACG GATTTTATGT     420
TTGCCCAGGA CCACCAAATA ATGGAAAACA TTGCGGAAAT CCCAGAGATT TCTTTTGTAA     480
ACAATGGAAC TGTGTAACCT CTAATGATGG ATATTGGAAA TGGCCAACCT CTCAGCAGGA     540
TAGGGTAAGT TTTTCTTATG TCAACACCTA TACCAGCTCT GGACAATTTA ATTACCTGAC     600
CTGGATTAGA ACTGGAAGCC CCAAGTGCTC TCCTTCAGAC CTAGATTACC TAAAAATAAG     660
TTTCACTGAG AAAGGAAAAC AAGAAAATAT CCTAAAATGG GTAAATGGTA TGTCTTGGGG     720
AATGGTATAT TATGGAGGCT CGGGTAAACA ACCAGGCTCC ATTCTAACTA TTCGCCTCAA     780
AATAAACCAG CTGGAGCCTC CAATGGCTAT AGGACCAAAT ACGGTCTTGA CGGGTCAAAG     840
ACCCCCAACC CAAGGACCAG GACCATCCTC TAACATAACT TCTGGATCAG ACCCCACTGA     900
GTCTAGCAGC ACGACTAAAA TGGGGGCAAA ACTTTTTAGC CTCATCCAGG GAGCTTTTCA     960
AGCTCTTAAC TCCACGACTC CAGAGGCTAC CTCTTCTTGT TGGCTATGCT TAGCTTTGGG    1020
CCCACCTTAC TATGAAGGAA TGGCTAGAAG AGGGAAATTC AATGTGACAA AGAACATAG    1080
AGACCAATGC ACATGGGGAT CCCAAAATAA GCTTACCCTT ACTGAGGTTT CTGGAAAAGG    1140
CACCTGCATA GGAAAGGTTC CCCCATCCCA CCAACACCTT TGTAACCACA CTGAAGCCTT    1200
TAATCAAACC TCTGAAAGTC AATATCTGGT ACCTGGTTAT GACAGGTGGT GGGCATGTAA    1260
TACTGGATTA ACCCCTTGTG TTTCCACCTT GGTTTTTAAC CAAACTAAAG ATTTTTGCAT    1320
TATGGTCCAA ATTGTTCCCC GAGTGTATTA CTATCCCGAA AAAGCAATCC TTGATGAATA    1380
TGACTACAGA AATCATCGAC AAAAGAGAGA ACCCATATCT CTGACACTTG CTGTGATGCT    1440
CGGACTTGGA GTGGCAGCAG GTGTAGGAAC AGGAACAGCT GCCCTGGTCA CGGGACCACA    1500
GCAGCTAGAA ACAGGACTTA GTAACCTACA TCGAATTGTA ACAGAAGATC TCCAAGCCCT    1560
AGAAAAATCT GTCAGTAACC TGGAGGAATC CCTAACCTCC TTATCTGAAG TAGTCCTACA    1620
GAATAGAAGA GGGTTAGATT TATTATTTCT AAAAGAAGGA GGATTATGTG TAGCCTTGAA    1680
GGAGGAATGC TGTTTTTATG TGGATCATTC AGGGGCCATC AGAGACTCCA TGAACAAACT    1740
TAGAGAAAGG TTGGAGAAGC GTCGAAGGGA AAAGGAAACT ACTCAAGGGT GGTTTGAGGG    1800
```

```
ATGGTTCAAC AGGTCTCCTT GGTTGGCTAC CCTACTTTCT GCTTTAACAG GACCCTTAAT    1860

AGTCCTCCTC CTGTTACTCA CAGTTGGGCC ATGTATTATT AACAAGTTAA TTGCCTTCAT    1920

TAGAGAACGA ATAAGTGCAG TCCAGATCAT GGTACTTAGA CAACAGTACC AAAGCCCGTC    1980

TAGCAGGGAA GCTGGCCGCT AGCTCTACCA GTTCTAAGAT TAGAACTATT AACAAGAGAA    2040

GAAGTGGGGA ATGAAAGGAT GAAAATACAA CCTAAGCTAA TGAGAAGCTT AAAATTGTTC    2100

TGAATTCCAG AGTTTGTTCC TTATAGGTAA AAGATTAGGT TTTTTGCTGT TTTAAAATAT    2160

GCGGAAGTAA AATAGGCCCT GAGTACATGT CTCTAGGCAT GAAACTTCTT GAAACTATTT    2220

GAGATAACAA GAAAGGGAG TTTCTAACTG CTTGTTTAGC TTCTGTAAAA CTGGTTGCGC    2280

CATAAAGATG TTGAAATGTT GATACACATA TCTTGGTGAC AACATGTCTC CCCCACCCCG    2340

AAACATGCGC AAATGTGTAA CTCTAAAACA ATTTAAATTA ATTGGTCCAC GAAGCGCGGG    2400

CTCTCGAAGT TTTAAATTGA CTGGTTTGTG ATATTTGAA ATGATTGGTT TGTAAAGCGC    2460

GGGCTTTGCT GTGAACCCCA TAAAAGCTGT CCCGACTCCA CACTCGGGGC CGCAGTCCTC    2520

TACCCCTGCG TGGTGTACGA CTGTGGGCCC CAGCGCGCTT GGAATAAAAA TCCTCTTGCT    2580

GTTTGCATCA AGACCGCTTC TCGTGAGTGA TTAAGGGGAG TCGCCTTTTC CGAGCCTGGA    2640

GGTTCTTTTT GCTGGTCTTA CATTTGGGGG CTCGTCCGGG ATCTGTCGCG GCCACCCCTA    2700

ACACCCGAGA ACCGACTTGG AGGTAAAAAG GATCCTCTTT TTAACGTGTA TGCATGTACC    2760

GGCCGGCGTC TCTGTTCTGA GTGTCTGTTT TCAGTGGTGC GCGCTTTCGG TTTGCAGCTG    2820

TCCTCTCAGG CCGTAAGGGC TGGGGACTG TGATCAGCAG ACGTGCTAGG AGGATCACAG    2880

GCTGCTGCCC TGGGGACGC CCCGGGAGGT GAGGAGAGCC AGGGACGCCT GGTGGTCTCC    2940

TACTGTCGGT CAGAGGACCG AATTCTGTTG CTGAAGCGAA AGCTTCCCCC TCCGCGACCG    3000

TCCGACTCTT TTGCCTGCTT GTGGAATACG TGGACGGGTC ACGTGTGTCT GGATCTGTTG    3060

GTTTCTGTTT TGTGTGTCTT TGTCTTGTGT GTCCTTGTCT ACAGTTTTAA TATGGGACAG    3120

ACGGTGACGA CCCCTCTTAG TTTGACTCTC GACCATTGGA CTGAAGTTAA ATCCAGGGCT    3180

CATAATTTGT CAGTTCAGGT TAAGAAGGGA CCTTGGCAGA CTTTCTGTGT CTCTGAATGG    3240

CCGACATTCG ATGTTGGATG GCCATCAGAG GGGACCTTTA ATTCTGAGAT TATCCTGGCT    3300

GTTAAAGCAA TTATTTTTCA GACTGGACCC GGCTCTCATC CCGATCAGGA GCCCTATATC    3360

CTTACGTGGC AAGATTTGGC AGAGGATCCT CCGCCATGGG TTAAACCATG GCTGAATAAG    3420

CCAAGAAAGC CAGGTCCCCG AATTCTGGCT CTTGGAGAGA AAAACAAACA CTCGGCTGAA    3480

AAAGTCAAGC CCTCTCCTCA TATCTACCCC GAGATTGAGG AACCACCGGC TTGGCCGGAA    3540

CCCCAATCTG TTCCCCCACC CCCTTATCTG GCACAGGGTG CCGCGAGGGG ACCCTTTGCC    3600

CCTCCTGGAG CTCCGGCGGT GGAGGGACCT TCTGCAGGGA CTCGGAGCCG GAGGGGCGCC    3660

ACCCCGGAGC GGACAGACGA GATCGCGACA TTACCGCTGC GCACGTACGG CCCTCCCACA    3720

CCGGGGGGCC AATTGCAGCC CCTCCAGTAT TGGCCCTTTT CTTCTGCAGA TCTCTATAAT    3780

TGGAAAACTA ACCATCCCCC TTTCTCGGAG GATCCCCAAC GCCTCACGGG GTTGGTGGAG    3840

TCCCTTATGT TCTCTCACCA GCCTACTTGG GATGATTGTC AACAGCTGCT GCAGACACTC    3900

TTCACAACCG AGGAGCGAGA GAGAATTCTA TTAGAGGCTA GAAAAAATGT TCCTGGGGCC    3960

GACGGGCGAC CCACGCGGTT GCAAAATGAG ATTGACATGG GATTTCCCTT AACTCGCCCC    4020

GGTTGGGACT ACAACACGGC TGAAGGTAGG GAGAGCTTGA AAATCTATCG CCAGGCTCTG    4080

GTGGCGGGTC TCCGGGGCGC CTCAAGACGG CCCACTAATT TGGCTAAGGT AAGAGAAGTG    4140
```

-continued

```
ATGCAGGGAC CGAATGAACC CCCCTCTGTT TTTCTTGAGA GGCTCTTGGA AGCCTTCAGG    4200

CGGTACACCC CTTTTGATCC CACCTCAGAG GCCCAAAAAG CCTCAGTGGC TTTGGCCTTT    4260

ATAGGACAGT CAGCCTTGGA TATTAGAAAG AAGCTTCAGA GACTGGAAGG GTTACAGGAG    4320

GCTGAGTTAC GTGATCTAGT GAAGGAGGCA GAGAAAGTAT ATTACAAAAG GGAGACAGAA    4380

GAAGAAAGGG AACAAAGAAA AGAGAGAGAA AGAGAGGAAA GGGAGGAAAG ACGTAATAAA    4440

CGGCAAGAGA AGAATTTGAC TAAGATCTTG GCTGCAGTGG TTGAAGGGAA AAGCAATACG    4500

GAAAGAGAGA GAGATTTTAG GAAAATTAGG TCAGGCCCTA GACAGTCAGG GAACCTGGGC    4560

AATAGGACCC CACTCGACAA GGACCAATGT GCATATTGTA AAGAAAGAGG ACACTGGGCA    4620

AGGAACTGCC CCAAGAAGGG AAACAAAGGA CCAAGGATCC TAGCTCTAGA AGAAGATAAA    4680

GATTAGGGGA GACGGGGTTC GGACCCCCTC CCCGAGCCCA GGGTAACTTT GAAGGTGGAG    4740

GGGCAACCAG TTGAGTTCCT GGTTGATACC GGAGCGAAAC ATTCAGTGCT ACTACAGCCA    4800

TTAGGAAAAC TAAAAGATAA AAAATCCTGG GTGATGGGTG CACAGGGCAA CAACAGTATC    4860

CATGGACTAC CCGAAGACAG TTGACTTGGG AGTGGGACGG GTAACCCACT CGTTTCTGGT    4920

CATACCTGAG TGCCCAGCAC CCCTCTTAGG TAGAGACTTA TTGACCAAGA TGGGAGCACA    4980

AATTTCTTTT GAACAAGGGA AACCAGAAGT GTCTGCAAAT AACAAACCTA TCACTGTGTT    5040

GACCCTCCAA TTAGATGACG AATATCGACT ATACTCTCCC CTAGTAAAGC CTGATCAAAA    5100

TATACAATTC TGGTTGGAAC AGTTTCCCCA AGCCTGGGCA GAAACCGCAG GGATGGGTTT    5160

GGCAAAGCAA GTTCCCCCAC AAGTTATTCA ACTGAAGGCC AGTGCCACAC CAGTGTCAGT    5220

CAGACAGTAC CCCTTGAGTA AAGAAGCTCA AGAAGGAATT CGGCCGCATG TCCAAAGATT    5280

AATCCAACAG GGCATCCTAG TTCCTGTCCA ATCTCCCTGG AATACTCCCC TGCTACCGGT    5340

TAGAAAGCCT GGGACTAATG ACTATCGACC AGTACAGGAC TTGAGAGAGG TCAATAAACG    5400

GGTGCAGGAT ATACACCCAA CAGTCCCGAA CCCTTATAAC CTCTTGTGTG CTCTCCCACC    5460

CCAACGGAGC TGGTATACAG TATTGGACTT AAAGGATGCC TTCTTCTGCC TGAGATTACA    5520

CCCCACTAGC CAACCACTTT TTGCCTTCGA ATGGAGAGAT CCAGGTACGG GAAGAACCGG    5580

GCAGCTCACC TGGACCCGAC TGCCCCAAGG GTTCAAGAAC TCCCCGACCA TCTTTGACGA    5640

AGCCCTACAC AGAGACCTGG CCAACTTCAG GATCCAACAC CCTCAGGTGA CCCTCCTCCA    5700

GTACGTGGAT GACCTGCTTC TGGCGGGAGC CACCAAACAG GACTGCTTAG AAGGCACGAA    5760

GGCACTACTG CTGGAATTGT CTGACCTAGG CTACAGAGCC TCTGCTAAGA AGGCCCAGAT    5820

TTGCAGGAGA GAGGTAACAT ACTTGGGGTA CAGTTTACGG GACGGGCAGC GATGGCTGAC    5880

GGAGGCACGG AAGAAAACTG TAGTCCAGAT ACCGGCCCCA ACCACAGCCA AACAAATGAG    5940

AGAGTTTTTG GGGACAGCTG GATTTTGCAG ACTGTGGATC CCGGGGTTTG CGACCTTAGC    6000

AGCCCCACTC TACCCGCTAA CCAAAGAAAA AGGGGAATTC TCCTGGGCTC CTGAGCACCA    6060

GAAGGCATTT GATGCTATCA AAAAGGCCCT GCTGAGCGCA CCTGCTCTGG CCCTCCCTGA    6120

CGTAACTAAA CCCTTTACCC TTTATGTGGA TGAGCGTAAG GGAGTAGCCC GGGGAGTTTT    6180

AACCCAAACC CTAGGACCAT GGAGAAGACC TGTCGCCTAC CTGTCAAAGA AGCTCGATCC    6240

TGTAGCCAGT GGTTGGCCCA TATGCCTGAA GGCTATCGCA GCTGTGGCCA TACTGGTCAA    6300

GGACGCTGAC AAATTGACTT TGGGACAAGA ATATAACTGT AATAGCCCCC CATGCATTGG    6360

AGAACATCGT TCGGCAGCCC CCAGACCGAT GGATGACCAA CGCCCGCATG ACCCACTATC    6420

AAAGCCTGCT TCTCACAGAG AGGGTCACGT TCGCTCCACC AACCGCTCTC AACCCTGCCA    6480

CTCTTCTGCC TGAAGAGACT GATGAACCAG TGACTCATGA TTGCCATCAA CTATTGATTG    6540
```

-continued

```
AGGAGACTGG GGTCCGCAAG GACCTTACAG ACATACCGCT GACTGGAGAA GTGCTAACCT      6600

GGTTCACTGA CGGAAGCAGC TATGTGGTGG AAGGTAAGAG GATGGCTGGG GCGGCGGTGG      6660

TGGACGGGAC CCGCACGATC TGGGCCAGCA GCCTGCCGGG AGGAACTTCA GCACAAAAGG      6720

CTGAGCTCAT GGCCCTCACG CAAGCTTTGC GGCTGGCCGA AGGGAAATCC ATAAACATTT      6780

ATACGGACAG CAGGTATGCC TTTGCGACTG CACACGTACA TGGGGCCATC TATAAACAAA      6840

GGGGGTTGCT TACCTCAGCA GGGAGGGAAA TAAAGAACAA AGAGGAAATT CTAAGCCTAT      6900

TAGAAGCCGT ACATTTACCA AAAAGGCTAG CTATTATACA CTGTCCTGGA CATCAGAAAG      6960

CTAAAGATCT CATATCCAGA GGAAACCAGA TGGCTGACCG GGTTGCCAAG CAGGCAGCCC      7020

AGGGTGTTAA CCTTCTGCCT ATAATAGAAA TGCCCAAAGC CCCAGAACCC AGACGACAGT      7080

ACACCCTAGA AGACTGGCAA GAGATAAAAA AGATAGACCA TTCTCTGAGA CTCCGGAAGG      7140

GACCTGCTAT ACCTCAGATG GGAAGGAAAT CCTGCCCCAC AAAGAAGGGT TAGAATATGT      7200

CCAACAAGAT ACATCGTCTA ACCCACCTAG GAACTAAACA CCTGCAGCAG TTGGTCAGAA      7260

CATCCCCTTA TCATGTTCTG AGGCTACCAG GAGTGGCTGA CTCGGTGGTC AAACATTGTG      7320

TGCCCTGCCA GCTGGTTAAT GCTAATCCTT CCAGAATGCC TCCAGGGAAG AGACTAAGGG      7380

GAAGCCACCC AGGCGCTCAC TGGGAAGTGG ACTTCACTGA GGTAAAGCCG GCTAAATATG      7440

GAAACAAATA CCTATTGGTT TTTGTAGACA CCTTTTCAGG ATGGGTAGAG GCTTATCCTA      7500

CTAAGAAAGA GACTTCAACC GTGGTAGCTA AAAAAATACT GGAAGAAATT TTTCCAAGAT      7560

TTGGAATACC TAAGGTAATA GGGTCAGACA ATGGTCCAGC TTTTGTTGCC CAGGTAAGTC      7620

AGGGACTGGC CAAGATATTG GGGATTGATT GGAAACTGCA TTGTGCATAC AGACCCCAAA      7680

GCTCAGGACA GGTAGAGAGG ATGAATAGAA CCATTAAAGA GACCCTTACT AAATTGACCG      7740

CGGAGACTGG CGTTAATGAT TGGATAGCTC TCCTGCCCTT TGTGCTTTTT AGGGTTAGGA      7800

ACACCCCTGG ACAGTTTGGG CTGACCCCCT ATGAATTACT CTACGGGGA CCCCCCCCAT       7860

TGGTAGAAAT TGCTTCTGTA CATAGTGCTG ATGTGCTGCT TTCCCAGCCT TTGTTCTCTA      7920

GGCTCAAGGC ACTTGAGTGG GTGAGACAAC GAGCGTGGAG GCAACTCCGG GAGGCCTACT      7980

CAGGAGGAGG AGACTTGCAG ATCCCACATC GTTTCCAAGT GGGAGATTCA GTCTACGTTA      8040

GACGCCACCG TGCAGGAAAC                                                 8060
```

(2) INFORMATION FOR SEQ ID NO:2:

(i) SEQUENCE CHARACTERISTICS:
        (A) LENGTH: 7333 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
CTACCCCTGC GTGGTGTACG ACTGTGGGCC CCAGCGCGCT TGGAATAAAA ATCCTCTTGC        60

TGTTTGCATC AAGACCGCTT CTTGTGAGTG ATTTGGGGTG TCGCCTCTTC CGAGCCCGGA       120

CGAGGGGGAT TGTTCTTTTA CTGGCCTTTC ATTTGGTGCG TTGGCCGGGA AATCCTGCGA       180

CCACCCCTTA CACCCGAGAA CCGACTTGGA GGTAAAGGGA TCCCCTTTGG AACATATGTG       240

TGTGTCGGCC GGCGTCTCTG TTCTGAGTGT CTGTTTTCGG TGATGCGCGC TTTCGGTTTG       300

CAGCTGTCCT CTCAGACCGT AAGGACTGGA GGACTGTGAT CAGCAGACGT GCTAGGAGGA       360

TCACAGGCTG CCACCCTGGG GGACGCCCCG GGAGGTGGGG AGAGCCAGGG ACGCCTGGTG       420
```

```
GTCTCCTACT GTCGGTCAGA GGACCGAGTT CTGTTGTTGA AGCGAAAGCT TCCCCCTCCG        480

CGGCCGTCCG ACTCTTTTGC CTGCTTGTGG AAGACGCGGA CGGGTCGCGT GTGTCTGGAT        540

CTGTTGGTTT CTGTTTCGTG TGTCTTTGTC TTGTGCGTCC TTGTCTACAG TTTTAATATG        600

GGACAGACAG TGACTACCCC CCTTAGTTTG ACTCTCGACC ATTGGACTGA AGTTAGATCC        660

AGGGCTCATA ATTTGTCAGT TCAGGTTAAG AAGGGACCTT GGCAGACTTT CTGTGCCTCT        720

GAATGGCCAA CATTCGATGT TGGATGGCCA TCAGAGGGGA CCTTTAATTC TGAAATTATC        780

CTGGCTGTTA AGGCAATCAT TTTTCAGACT GGACCCGGCT CTCATCCTGA TCAGGAGCCC        840

TATATCCTTA CGTGGCAAGA TTTGGCAGAA GATCCTCCGC CATGGGTTAA ACCATGGCTA        900

AATAAACCAA GAAAGCCAGG TCCCCGAATC CTGGCTCTTG GAGAGAAAAA CAAACACTCG        960

GCCGAAAAAG TCGAGCCCTC TCCTCGTATC TACCCCGAGA TCGAGGAGCC GCCGACTTGG       1020

CCGGAACCCC AACCTGTTCC CCCACCCCCT TATCCAGCAC AGGGTGCTGT GAGGGGACCC       1080

TCTGCCCCTC CTGGAGCTCC GGTGGTGGAG GGACCTGCTG CCGGGACTCG AGCCGGAGA        1140

GGCGCCACCC CGGAGCGGAC AGACGAGATC GCGATATTAC CGCTGCGCAC CTATGGCCCT       1200

CCCATGCCAG GGGGCCAATT GCAGCCCCTC CAGTATTGGC CCTTTTCTTC TGCAGATCTC       1260

TATAATTGGA AAACTAACCA TCCCCCTTTC TCGGAGGATC CCCAACGCCT CACGGGGTTG       1320

GTGGAGTCCC TTATGTTCTC TCACCAGCCT ACTTGGGATG ATTGTCAACA GCTGCTGCAG       1380

ACACTCTTCA CAACCGAGGA GCGAGAGAGA ATTCTGTTAG AGGCTAAAAA AAATGTTCCT       1440

GGGGCCGACG GGCGACCCAC GCAGTTGCAA AATGAGATTG ACATGGGATT TCCCTTGACT       1500

CGCCCCGGTT GGGACTACAA CACGGCTGAA GGTAGGGAGA GCTTGAAAAT CTATCGCCAG       1560

GCTCTGGTGG CGGGTCTCCG GGGCGCCTCA AGACGGCCCA CTAATTTGGC TAAGGTAAGA       1620

GAGGTGATGC AGGGACCGAA CGAACCTCCC TCGGTATTTC TTGAGAGGCT CATGGAAGCC       1680

TTCAGGCGGT TCACCCCTTT TGATCCTACC TCAGAGGCCC AGAAAGCCTC AGTGGCCCTG       1740

GCCTTCATTG GCAGTCGGC TCTGGATATC AGGAAGAAAC TTCAGAGACT GGAAGGGTTA       1800

CAGGAGGCTG AGTTACGTGA TCTAGTGAGA GAGGCAGAGA AGGTGTATTA CAGAAGGGAG       1860

ACAGAAGAGG AGAAGGAACA GAGAAAAGAA AAGGAGAGAG AAGAAAGGGA GGAAAGACGT       1920

GATAGACGGC AAGAGAAGAA TTTGACTAAG ATCTTGGCCG CAGTGGTTGA AGGGAAGAGC       1980

AGCAGGGAGA GAGAGAGAGA TTTTAGGAAA ATTAGGTCAG GCCCTAGACA GTCAGGGAAC       2040

CTGGGCAATA GGACCCCACT CGACAAGGAC CAGTGTGCGT ATTGTAAAGA AAAAGGACAC       2100

TGGGCAAGGA ACTGCCCCAA GAAGGGAAAC AAAGGACCGA AGGTCCTAGC TCTAGAAGAA       2160

GATAAAGATT AGGGGAGACG GGGTTCGGAC CCCCTCCCCG AGCCCAGGGT AACTTTGAAG       2220

GTGGAGGGGC AACCAGTTGA GTTCCTGGTT GATACCGGAG CGGAGCATTC AGTGCTGCTA       2280

CAACCATTAG GAAAACTAAA AGAAAAAAAA TCCTGGGTGA TGGGTGCCAC AGGGCAACGG       2340

CAGTATCCAT GGACTACCCG AAGAACCGTT GACTTGGGAG TGGGACGGGT AACCCACTCG       2400

TTTCTGGTCA TCCCTGAGTG CCCAGTACCC CTTCTAGGTA GAGACTTACT GACCAAGATG       2460

GGAGCTCAAA TTTCTTTTGA ACAAGGAAGA CCAGAAGTGT CTGTGAATAA CAAACCCATC       2520

ACTGTGTTGA CCCTCCAATT AGATGATGAA TATCGACTAT ATTCTCCCCA AGTAAAGCCT       2580

GATCAAGATA TACAGTCCTG GTTGGAGCAG TTTCCCCAAG CCTGGGCAGA AACCGCAGGG       2640

ATGGGTTTGG CAAAGCAAGT TCCCCCACAG GTTATTCAAC TGAAGGCCAG TGCTACACCA       2700

GTATCAGTCA GACAGTACCC CTTGAGTAGA GAGGCTCGAG AAGGAATTTG GCCGCATGTT       2760
```

-continued

```
CAAAGATTAA TCCAACAGGG CATCCTAGTT CCTGTCCAAT CCCCTTGGAA TACTCCCCTG    2820

CTACCGGTTA GGAAGCCTGG GACCAATGAT TATCGACCAG TACAGGACTT GAGAGAGGTC    2880

AATAAAAGGG TGCAGGACAT ACACCCAACG GTCCCGAACC CTTATAACCT CTTGAGCGCC    2940

CTCCCGCCTG AACGGAACTG GTACACAGTA TTGGACTTAA AGATGCCTT CTTCTGCCTG     3000

AGATTACACC CCACTAGCCA ACCACTTTTT ACCTTCGAAT GGAGAGATCC AGGTACGGGA    3060

AGAACCGGGC AGCTCACCTG GACCCGACTG CCCCAAGGGT TCAAGAACTC CCCGACCATC    3120

TTTGACGAAG CCCTACACAG GGACCTGGCC AACTTCAGGA TCCAACACCC TCAGGTGACC    3180

CTCCTCCAGT ACGTGGATGA CCTGCTTCTG GCGGGAGCCA CCAAACAGGA CTGCTTAGAA    3240

GGTACGAAGG CACTACTGCT GGAATTGTCT GACCTAGGCT ACAGAGCCTC TGCTAAGAAG    3300

GCCCAGATTT GCAGGAGAGA GGTAACATAC TTGGGGTACA GTTTGCGGGG CGGGCAGCGA    3360

TGGCTGACGG AGGCACGGAA GAAAACTGTA GTCCAGATAC CGGCCCCAAC CACAGCCAAA    3420

CAAGTGAGAG AGTTTTTGGG GACAGCTGGA TTTTGCAGAC TGTGGATCCC GGGGTTTGCG    3480

ACCTTAGCAG CCCCACTCTA CCCGCTAACC AAAGAAAAAG GGGGTTGCTT ACCTCAGCAG    3540

GGAGGGAAAT AAAGAACAAA GAGGAAATTC TAAGCCTATT AGAAGCCTTA CATTTGCCAA    3600

AAAGGCTAGC TATTATACAC TGTCCTGGAC ATCAGAAAGC CAAAGATCTC ATATCTAGAG    3660

GGAACCAGAT GGCTGACCGG GTTGCCAAGC AGGCAGCCCA GGCTGTTAAC CTTCTGCCTA    3720

TAATAGAAAC GCCCAAAGCC CCAGAACCCA GACGACAGTA CACCCTAGAA GACTGGCAAG    3780

AGATAAAAAA GATAGACCAG TTCTCTGAGA CTCCGGAGGG GACCTGCTAT ACCTCATATG    3840

GGAAGGAAAT CCTGCCCCAC AAAGAAGGGT TAGAATATGT CCAACAGATA CATCGTCTAA    3900

CCCACCTAGG AACTAAACAC CTGCAGCAGT TGGTCAGAAC ATCCCCTTAT CATGTTCTGA    3960

GGCTACCAGG AGTGGCTGAC TCGGTGGTCA ACATTGTGT GCCCTGCCAG CTGGTTAATG     4020

CTAATCCTTC CAGAATACCT CCAGGAAAGA GACTAAGGGG AAGCCACCCA GGCGCTCACT    4080

GGGAAGTGGA CTTCACTGAG GTAAAGCCGG CTAAATACGG AAACAAATAT CTATTGGTTT    4140

TTGTAGACAC CTTTTCAGGA TGGGTAGAGG CTTATCCTAC TAAAAAGAG ACTTCAACCG     4200

TGGTGGCTAA GAAAATACTG GAGGAAATTT TTCCAAGATT TGGAATACCT AAGGTAATAG    4260

GGTCAGACAA TGGTCCAGCT TTCGTTGCCC AGGTAAGTCA GGGACTGGCC AAGATATTGG    4320

GGATTGATTG AAAACTGCAT TGTGCATACA GACCCCAAAG CTCAGGACAG GTAGAGAGGA    4380

TGAATAGAAC CATTAAGAG ACCCTTACCA AATTGACCAC AGAGACTGGC ATTAATGATT     4440

GGATGGCTCT CCTGCCCTTT GTGCTTTTTA GGGTGAGGAA CACCCCTGGA CAGTTTGGGC    4500

TGACCCCCTA TAAATTGCTC TACGGGGAC CCCCCCCGTT GGCAGAAATT GCCTTTGCAC     4560

ATAGTGCTGA TGTGCTGCTT TCCCAGCCTT TGTTCTCTAG GCTCAAGGCG CTCGAGTGGG    4620

TGAGGCAGCG AGCGTGGAAG CAGCTCCGGG AGGCCTACTC AGGAGGAGAC TTGCAAGTTC    4680

CACATCGCTT CCAAGTTGGA GATTCAGTCT ATGTTAGACG CCACCGTGCA GGAAACCTCG    4740

AGACTCGGTA GAAGGGACCT TATCTCGTAC TTTTGACCAC ACCAACGGCT GTGAAAGTCG    4800

AAGGAATCCC CTTAAGCTTC GCCTCCATCG CGTGGTTCCT TACTCTGTCA ATAACTCCTC    4860

AAGTTAATGG TAAACGCCTT GTGGACAGCC CGAACTCCCA TAAACCCTTA TCTCTCACCT    4920

GGTTACTTAC TGACTCCGGT ACAGGTATTA ATATTAACAG CACTCAAGGG GAGGCTCCCT    4980

TGGGGACCTG GTGGCCTGAA TTATATGTCT GCCTTCGATC AGTAATCCCT GGTCTCAATG    5040

ACCAGGCCAC ACCCCCGAT GTACTCCGTG CTTACGGGTT TTACGTTTGC CCAGGACCCC     5100

CAAATAATGA AGAATATTGT GGAAATCCTC AGGATTTCTT TTGCAAGCAA TGGAGCTGCA    5160
```

```
TAACTTCTAA TGATGGGAAT TGGAAATGGC CAGTCTCTCA GCAAGACAGA GTAAGTTACT    5220

CTTTTGTTAA CAATCCTACC AGTTATAATC AATTTAATTA TGGCCATGGG AGATGGAAAG    5280

ATTGGCAACA GCGGGTACAA AAAGATGTAC GAAATAAGCA AATAAGCTGT CATTCGTTAG    5340

ACCTAGATTA CTTAAAAATA AGTTTCACTG AAAAAGGAAA ACAAGAAAAT ATTCAAAAGT    5400

GGGTAAATGG TATATCTTGG GGAATAGTGT ACTATGGAGG CTCTGGGAGA AGAAAGGAT     5460

CTGTTCTGAC TATTCGCCTC AGAATAGAAA CTCAGATGGA ACCTCCGGTT GCTATAGGAC    5520

CAAATAAGGG TTTGGCCGAA CAAGGACCTC CAATCCAAGA ACAGAGGCCA TCTCCTAACC    5580

CCTCTGATTA CAATACAACC TCTGGATCAG TCCCCACTGA GCCTAACATC ACTATTAAAA    5640

CAGGGGCGAA ACTTTTTAGC CTCATCCAGG GAGCTTTTCA AGCTCTTAAC TCCACGACTC    5700

CAGAGGCTAC CTCTTCTTGT TGGCTTTGCT TAGCTTCGGG CCCACCTTAC TATGAGGGAA    5760

TGGCTAGAGG AGGGAAATTC AATGTGACAA AGGAACATAG AGACCAATGT ACATGGGGAT    5820

CCCAAAATAA GCTTACCCTT ACTGAGGTTT CTGGAAAAGG CACCTGCATA GGGATGGTTC    5880

CCCCATCCCA CCAACACCTT TGTAACCACA CTGAAGCCTT TAATCGAACC TCTGAGAGTC    5940

AATATCTGGT ACCTGGTTAT GACAGGTGGT GGGCATGTAA TACTGGATTA ACCCCTTGTG    6000

TTTCCACCTT GGTTTTCAAC CAAACTAAAG ACTTTTGCGT TATGGTCCAA ATTGTCCCCC    6060

GGGTGTACTA CTATCCCGAA AAAGCAGTCC TTGATGAATA TGACTATAGA TATAATCGGC    6120

CAAAAAGAGA GCCCATATCC CTGACACTAG CTGTAATGCT CGGATTGGGA GTGGCTGCAG    6180

GCGTGGGAAC AGGAACGGCT GCCCTAATCA CAGGACCGCA ACAGCTGGAG AAAGGACTTA    6240

GTAACCTACA TCGAATTGTA ACGGAAGATC TCCAAGCCCT AGAAAAATCT GTCAGTAACC    6300

TGGAGGAATC CCTAACCTCC TTATCTGAAG TGGTTCTACA GAACAGAAGG GGGTTAGATC    6360

TGTTATTTCT AAAAGAAGGA GGGTTATGTG TAGCCTTAAA AGAGGAATGC TGCTTCTATG    6420

TAGATCACTC AGGAGCCATC AGAGACTCCA TGAGCAAGCT TAGAGAAAGG TTAGAGAGGC    6480

GTCGAAGGGA AAGAGAGGCT GACCAGGGGT GGTTTGAAGG ATGGTTCAAC AGGTCTCCTT    6540

GGATGACCAC CCTGCTTTCT GCTCTGACGG GGCCCCTAGT AGTCCTGCTC CTGTTACTTA    6600

CAGTTGGGCC TTGCTTAATT AATAGGTTTG TTGCCTTTGT TAGAGAACGA GTGAGTGCAG    6660

TCCAGATCAT GGTACTTAGG CAACAGTACC AAGGCCTTCT GAGCCAAGGA GAAACTGACC    6720

TCTAGCCTTC CCAGTTCTAA GATTAGAACT ATTAACAAGA CAAGAAGTGG GGAATGAAAG    6780

GATGAAAATG CAACCTAACC CTCCCAGAAC CCAGGAAGTT AATAAAAAGC TCTAAATGCC    6840

CCCGAATTCC AGACCCTGCT GGCTGCCAGT AAATAGGTAG AAGGTCACAC TTCCTATTGT    6900

TCCAGGGCCT GCTATCCTGG CCTAAGTAAG ATAACAGGAA ATGAGTTGAC TAATCGCTTA    6960

TCTGGATTCT GTAAAACTGA CTGGCACCAT AGAAGAATTG ATTACACATT GACAGCCCTA    7020

GTGACCTATC TCAACTGCAA TCTGTCACTC TGCCCAGGAG CCCACGCAGA TGCGGACCTC    7080

CGGAGCTATT TTAAAATGAT TGGTCCACGG AGCGCGGGCT CTCGATATTT TAAAATGATT    7140

GGTCCATGGA GCGCGGGCTC TCGATATTTT AAAATGATTG GTTTGTGACG CACAGGCTTT    7200

GTTGTGAACC CCATAAAAGC TGTCCCGATT CCGCACTCGG GGCCGCAGTC CTCTACCCCT    7260

GCGTGGTGTA CGACTGTGGG CCCCAGCGCG CTTGGAATAA AAATCCTCTT GCTGTTTGCA    7320

TCAAAAAAAA AAA                                                      7333
```

(2) INFORMATION FOR SEQ ID NO:3:
    (i) SEQUENCE CHARACTERISTICS:

(A) LENGTH: 8132 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

```
GCGTGGTGTA CGACTGTGGG CCCCAGCGCG CTTGGAATAA AAATCCTCTT GCTGTTTGCA      60
TCAAGACCGC TTCTCGTGAG TGATTAAGGG GAGTCGCCTT TTCCGAGCCT GGAGGTTCTT     120
TTTGCTGGTC TTACATTTGG GGGCTCGTCC GGGATCTGTC GCGGCCACCC CTAACACCCG     180
AGAACCGACT TGGAGGTAAA AAGGATCCTC TTTTTAACGT GTATGCATGT ACCGGCCGGC     240
GTCTCTGTTC TGAGTGTCTG TTTTCAGTGG TGCGCGCTTT CGGTTTGCAG CTGTCCTCTC     300
AGGCCGTAAG GGCTGGGGGA CTGTGATCAG CAGACGTGCT AGGAGGATCA CAGGCTGCTG     360
CCCTGGGGGA CGCCCCGGGA GGTGAGGAGA GCCAGGGACG CCTGGTGGTC TCCTACTGTC     420
GGTCAGAGGA CCGAATTCTG TTGCTGAAGC GAAAGCTTCC CCCTCCGCGA CCGTCCGACT     480
CTTTTGCCTG CTTGTGGAAG ACGTGGACGG GTCACGTGTG TCTGGATCTG TTGGTTTCTG     540
TTTTGTGTGT CTTTGTCTTG TGTGTCCTTG TCTACAGTTT TAATATGGGA CAGACGGTGA     600
CGACCCCTCT TAGTTTGACT CTCGACCATT GGACTGAAGT TAAATCCAGG GCTCATAATT     660
TGTCAGTTCA GGTTAAGAAG GGACCTTGGC AGACTTTCTG TGTCTCTGAA TGGCCGACAT     720
TCGATGTTGG ATGGCCATCA GAGGGGACCT TTAATTCTGA GATTATCCTG GCTGTTAAAG     780
CAGTTATTTT TCAGACTGGA CCCGGCTCTC ATCCCGATCA GGAGCCCTAT ATCCTTACGT     840
GGCAAGATTT GGCAGAGGAT CCTCCGCCAT GGGTTAAACC ATGGCTGAAT AAGCCAAGAA     900
AGCCAGGTCC CCGAATTCTG GCTCTTGGAG AGAAAAACAA ACACTCGGCT GAAAAAGTCA     960
AGCCCTCTCC TCATATCTAC CCCGAGATTG AGGAGCCACC GGCTTGGCCG GAACCCCAAT    1020
CTGTTCCCCC ACCCCCTTAT CTGGCACAGG GTGCCGCGAG GGGACCCTTT GCCCCTCCTG    1080
GAGCTCCGGC GGTGGAGGGA CCTGCTGCAG GGACTCGGAG CCGGAGGGGC GCCACCCCGG    1140
AGCGGACAGA CGAGATCGCG ACATTACCGC TGCGCACGTA CGGCCCTCCC ACACCGGGGG    1200
GCCAATTGCA GCCCCTCCAG TATTGGCCCT TTTCTTCTGC AGATCTCTAT AATTGGAAAA    1260
CTAACCATCC CCCTTTCTCG GAGGATCCCC AACGCCTCAC GGGGTTGGTG GAGTCCCTTA    1320
TGTTCTCTCA CCAGCCTACT TGGGATGATT GTCAACAGCT GCTGCAGACA CTCTTCACAA    1380
CCGAGGAGCG AGAGAGAATT CTATTAGAGG CTAGAAAAAA TGTTCCTGGG GCCGACGGGC    1440
GACCCACGCG GTTGCAAAAT GAGATTGACA TGGGATTTCC CTTAACTCGC CCCGGTTGGG    1500
ACTACAACAC GGCTGAAGGT AGGGAGAGCT TGAAAATCTA TCGCCAGGCT CTGGTGGCGG    1560
GTCTCCGGGG CGCCTCAAGA CGGCCCACTA ATTTGGCTAA GGTAAGAGAA GTGATGCAGG    1620
GACCGAATGA ACCCCCTCT GTTTTTCTTG AGAGGCTCTT GGAAGCCTTC AGGCGGTACA    1680
CCCCTTTTGA TCCCACCTCA GAGGCCCAAA AAGCCTCAGT GGCTTTGGCC TTTATAGGAC    1740
AGTCAGCCTT GGATATTAGA AAGAAGCTTC AGAGACTGGA AGGGTTACAG GAGGCTGAGT    1800
TACGTGATCT AGTGAAGGAG GCAGAGAAAG TATATTACAA AAGGGAGACA GAAGAAGAAA    1860
GGGAACAAAG AAAAGAGAGA GAAAGAGAGG AAAGGGAGGA AAGACGTAAT AAACGGCAAG    1920
AGAAGAATTT GACTAAGATC TTGGCTGCAG TGGTTGAAGG GAAAAGCAAT ACGGAAAGAG    1980
AGAGAGATTT TAGGAAAATT AGGTCAGGCC CTAGACAGTC AGGGAACCTG GCAATAGGA    2040
CCCCACTCGA CAAGGACCAA TGTGCATATT GTAAAGAAAG AGGACACTGG GCAAGGAACT    2100
```

```
GCCCCAAGAA GGGAAACAAA GGACCAAGGA TCCTAGCTCT AGAAGAAGAT AAAGATTAGG    2160

GGAGACGGGG TTCGGACCCC CTCCCCGAGC CCAGGGTAAC TTTGAAGGTG GAGGGGCAAC    2220

CAGTTGAGTT CCTGGTTGAT ACCGGAGCGA AACATTCAGT GCTACTACAG CCATTAGGAA    2280

AACTAAAAGA TAAAAAATCC TGGGTGATGG GTGCCACAGG GCAACAACAG TATCCATGGA    2340

CTACCCGAAG AACAGTTGAC TTGGGAGTGG GACGGGTAAC CCACTCGTTT CTGGTCATAC    2400

CTGAGTGCCC AGCACCCCTC TTAGGTAGAG ACTTATTGAC CAAGATGGGA GCACAAATTT    2460

CTTTTGAACA AGGGAAACCA GAAGTGTCTG CAAATAACAA ACCTATCACT GTGTTGACCC    2520

TCCAATTAGA TGACGAATAT CGACTATACT CTCCCCTAGT AAAGCCTGAT CAAAATATAC    2580

AATTCTGGTT GGAACAGTTT CCCCAAGCCT GGGCAGAAAC CGCAGGGATG GGTTTGGCAA    2640

AGCAAGTTCC CCCACAAGTT ATTCAACTGA AGGCCAGTGC CACACCAGTG TCAGTCAGAC    2700

AGTACCCCTT GAGTAAAGAA GCTCAAGAAG GAATTCGGCC GCATGTCCAA AGATTAATCC    2760

AACAGGGCAT CCTAGTTCCT GTCCAATCTC CCTGGAATAC TCCCCTGCTA CCGGTTAGAA    2820

AGCCTGGGAC TAATGACTAT CGACCAGTAC AGGACTTGAG AGAGGTCAAT AAACGGGTGC    2880

AGGATATACA CCCAACAGTC CCGAACCCTT ATAACCTCTT GTGTGCTCTC CCACCCCAAC    2940

GGAGCTGGTA TACAGTATTG GACTTAAAGG ATGCCTTCTT CTGCCTGAGA TTACACCCCA    3000

CTAGCCAACC ACTTTTTGCC TTCGAATGGA GAGATCCAGG TACGGGAAGA ACCGGGCAGC    3060

TCACCTGGAC CCGACTGCCC CAAGGGTTCA GAACTCCCC GACCATCTTT GACGAAGCCC     3120

TACACAGAGA CCTGGCCAAC TTCAGGATCC AACACCCTCA GGTGACCCTC CTCCAGTACG    3180

TGGATGACCT GCTTCTGGCG GGAGCCACCA ACAGGACTG CTTAGAAGGC ACGAAGGCAC     3240

TACTGCTGGA ATTGTCTGAC CTAGGCTACA GAGCCTCTGC TAAGAAGGCC CAGATTTGCA    3300

GGAGAGAGGT AACATACTTG GGGTACAGTT TGCGGGACGG GCAGCGATGG CTGACGGAGG    3360

CACGGAAGAA AACTGTAGTC CAGATACCGG CCCCAACCAC AGCCAAACAA ATGAGAGAGT    3420

TTTTGGGGAC AGCTGGATTT TGCAGACTGT GGATCCCGGG GTTTGCGACC TTAGCAGCCC    3480

CACTCTACCC GCTAACCAAA GAAAAGGGG AATTCTCCTG GGCTCCTGAG CACCAGAAGG     3540

CATTTGATGC TATCAAAAAG GCCCTGCTGA GCGCACCTGC TCTGGCCCTC CCTGACGTAA    3600

CTAAACCCTT TACCCTTTAT GTGGATGAGC GTAAGGGAGT AGCCCGGGGA GTTTAACCC     3660

AAACCCTAGG ACCATGGAGA AGACCTGTCG CCTACCTGTC AAAGAAGCTC GATCCTGTAG    3720

CCAGTGGTTG GCCCATATGC CTGAAGGCTA TCGCAGCTGT GGCCATACTG GTCAAGGACG    3780

CTGACAAATT GACTTTGGGA CAGAATATAA CTGTAATAGC CCCCCATGCA TTGGAGAACA    3840

TCGTTCGGCA GCCCCCAGAC CGATGGATGA CCAACGCCCG CATGACCCAC TATCAAAGCC    3900

TGCTTCTCAC AGAGAGGGTC ACGTTCGCTC CACCAGCCGC TCTCAACCCT GCCACTCTTC    3960

TGCCTGAAGA GACTGATGAA CCAGTGACTC ATGATTGCCA TCAACTATTG ATTGAGGAGA    4020

CTGGGGTCCG CAAGGACCTT ACAGACATAC CGCTGACTGG AGAAGTGCTA ACCTGGTTCA    4080

CTGACGGAAG CAGCTATGTG GTGGAAGGTA AGAGGATGGC TGGGGCGGCG GTGGTGGACG    4140

GGACCCGCAC GATCTGGGCC AGCAGCCTGC CGGAAGGAAC TTCAGCACAA AAGGCTGAGC    4200

TCATGGCCCT CACGCAAGCT TTGCGGCTGG CCGAAGGGAA ATCCATAAAC ATTTATACGG    4260

ACAGCAGGTA TGCCTTTGCG ACTGCACACG TACATGGGGC CATCTATAAA CAAAGGGGGT    4320

TGCTTACCTC AGCAGGGAGG GAAATAAAGA ACAAAGAGGA AATTCTAAGC CTATTAGAAG    4380

CCGTACATTT ACCAAAAAGG CTAGCTATTA TACACTGTCC TGGACATCAG AAAGCTAAAG    4440

ATCTCATATC CAGAGGAAAC CAGATGGCTG ACCGGGTTGC CAAGCAGGCA GCCCAGGGTG    4500
```

```
TTAACCTTCT GCCTATAATA GAAATGCCCA AAGCCCCAGA ACCCAGACGA CAGTACACCC    4560

TAGAAGACTG GCAAGAGATA AAAAAGATAG ACCAGTTCTC TGAGACTCCG GAAGGGACCT    4620

GCTATACCTC AGATGGGAAG GAAATCCTGC CCCACAAAGA AGGGTTAGAA TATGTCCAAC    4680

AGATACATCG TCTAACCCAC CTAGGAACTA AACACCTGCA GCAGTTGGTC AGAACATCCC    4740

CTTATCATGT TCTGAGGCTA CCAGGAGTGG CTGACTCGGT GGTCAAACAT TGTGTGCCCT    4800

GCCAGCTGGT TAATGCTAAT CCTTCCAGAA TGCCTCCAGG GAAGAGACTA AGGGGAAGCC    4860

ACCCAGGCGC TCACTGGGAA GTGGACTTCA CTGAGGTAAA GCCGGCTAAA TACGGAAACA    4920

AATACCTATT GGTTTTTGTA GACACCTTTT CAGGATGGGT AGAGGCTTAT CCTACTAAGA    4980

AAGAGACTTC AACCGTGGTG GCTAAAAAAA TACTGGAAGA AATTTTTCCA AGATTTGGAA    5040

TACCTAAGGT AATAGGGTCA GACAATGGTC CAGCTTTTGT TGCCCAGGTA AGTCAGGGAC    5100

TGGCCAAGAT ATTGGGGATT GATTGGAAAC TGCATTGTGC ATACAGACCC CAAAGCTCAG    5160

GACAGGTAGA GAGGATGAAT AGAACCATTA AAGAGACCCT TACTAAATTG ACCGCGGAGA    5220

CTGGCGTTAA TGATTGGATA GCTCTCCTGC CCTTTGTGCT TTTTAGGGTT AGGAACACCC    5280

CTGGACAGTT TGGGCTGACC CCCTATGAAT TACTCTACGG GGGACCCCCC CCATTGGTAG    5340

AAAATTGCTTC TGTACATAGT GCTGACGTGC TGCTTTCCCA GCCTTTGTTC TCTAGGCTCA    5400

AGGCACTTGA GTGGGTGAGA CAACGAGCGT GGAGGCAACT CCGGGAGGCC TACTCAGGAG    5460

GAGGAGACTT GCAGATCCCA CATCGTTTCC AAGTGGGAGA TTCAGTCTAC GTTAGACGCC    5520

ACCGTGCAGG AAACCTCGAG ACTCGGTGGA AGGGCCCTTA TCTCGTACTT TTGACCACAC    5580

CAACGGCTGT GAAAGTCGAA GGAATCTCCA CCTGGATCCA TGCATCCCAC GTTAAACCGG    5640

CGCCACCTCC CGATTCGGGG TGGAAAGCCG AAAAGACTGA AAATCCCCTT AAGCTTCGCC    5700

TCCATCGCGT GGTTCCTTAC TCTGTCAATA ACCTCTCAGA CTAATGGTAT GCGCATAGGA    5760

GACAGCCTGA ACTCCCATAA ACCCTTATCT CTCACCTGGT TAATTACTGA CTCCGGCACA    5820

GGTATTAATA TCAACAACAC TCAAGGGGAG GCTCCTTTAG GAACCTGGTG GCCTGATCTA    5880

TACGTTTGCC TCAGATCAGT TATTCCTAGT CTGACCTCAC CCCCAGATAT CCTCCATGCT    5940

CACGGATTTT ATGTTTGCCC AGGACCACCA AATAATGGAA AACATTGCGG AAATCCCAGA    6000

GATTTCTTTT GTAAACAATG GAACTGTGTA ACCTCTAATG ATGGATATTG GAAATGGCCA    6060

ACCTCTCAGC AGGATAGGGT AAGTTTTTCT TATGTCAACA CCTATACCAG CTCTGGACAA    6120

TTTAATTACC TGACCTGGAT TAGAACTGGA AGCCCCAAGT GCTCTCCTTC AGACCTAGAT    6180

TACCTAAAAA TAAGTTTCAC TGAGAAAGGA AAACAAGAAA ATATCCTAAA ATGGGTAAAT    6240

GGTATGTCTT GGGGAATGGT ATATTATGGA GGCTCGGGTA ACAACCAGG CTCCATTCTA     6300

ACTATTCGCC TCAAAATAAA CCAGCTGGAG CCTCCAATGG CTATAGGACC AAATACGGTC    6360

TTGACGGGTC AAAGACCCCC AACCCAAGGA CCAGGACCAT CCTCTAACAT AACTTCTGGA    6420

TCAGACCCCA CTGAGTCTAA CAGCACGACT AAAATGGGGG CAAAACTTTT TAGCCTCATC    6480

CAGGGAGCTT TTCAAGCTCT TAACTCCACG ACTCAGAGG CTACCTCTTC TTGTTGGCTA     6540

TGCTTAGCTT CGGGCCCACC TTACTATGAA GGAATGGCTA AAGAGGGAA ATTCAATGTG     6600

ACAAAAGAAC ATAGAGACCA ATGCACATGG GGATCCCAAA ATAAGCTTAC CCTTACTGAG    6660

GTTTCTGGAA AAGGCACCTG CATAGGAAAG GTTCCCCCAT CCCACCAACA CCTTTGTAAC    6720

CACACTGAAG CCTTTAATCA AACCTCTGAG AGTCAATATC TGGTACCTGG TTATGACAGG    6780

TGGTGGGCAT GTAATACTGG ATTAACCCCT TGTGTTTCCA CCTTGGTTTT TAACCAAACT    6840
```

-continued

```
AAAGATTTTT GCATTATGGT CCAAATTGTT CCCCGAGTGT ATTACTATCC CGAAAAAGCA    6900

ATCCTTGATG AATATGACTA CAGAAATCAT CGACAAAAGA GAGAACCCAT ATCTCTGACA    6960

CTTGCTGTGA TGCTCGGACT TGGAGTGGCA GCAGGTGTAG GAACAGGAAC AGCTGCCCTG    7020

GTCACGGGAC CACAGCAGCT AGAAACAGGA CTTAGTAACC TACATCGAAT TGTAACAGAA    7080

GATCTCCAAG CCCTAGAAAA ATCTGTCAGT AACCTGGAGG AATCCCTAAC CTCCTTATCT    7140

GAAGTAGTCC TACAGAATAG AAGAGGGTTA GATTTATTAT TTCTAAAAGA AGGAGGATTA    7200

TGTGTAGCCT TGAAGGAGGA ATGCTGTTTT TATGTGGATC ATTCAGGGGC CATCAGAGAC    7260

TCCATGAACA AGCTTAGAGA AAGGTTGGAG AAGCGTCGAA GGGAAAAGGA AACTACTCAA    7320

GGGTGGTTTG AGGGATGGTT CAACAGGTCT CTTTGGTTGG CTACCCTACT TTCTGCTTTA    7380

ACAGGACCCT TAATAGTCCT CCTCCTGTTA CTCACAGTTG GGCCATGTAT TATTAACAAG    7440

TTAATTGCCT TCATTAGAGA ACGAATAAGT GCAGTCCAGA TCATGGTACT TAGACAACAG    7500

TACCAAAGCC CGTCTAGCAG GGAAGCTGGC CGCTAGCTCT ACCAGTTCTA AGATTAGAAC    7560

TATTAACAAG AGAAGAAGTG GGGAATGAAA GGATGAAAAT ACAACCTAAG CTAATGAGAA    7620

GCTTAAAATT GTTCTGAATT CCAGAGTTTG TTCCTTATAG GTAAAGATT AGGTTTTTTG    7680

CTGTTTTAAA ATATGCGGAA GTAAAATAGG CCCTGAGTAC ATGTCTCTAG GCATGAAACT    7740

TCTTGAAACT ATTTGAGATA ACAAGAAAAG GGAGTTTCTA ACTGCTTGTT TAGCTTCTGT    7800

AAAACTGGTT GCGCCATAAA GATGTTGAAA TGTTGATACA CATATCTTGG TGACAACATG    7860

TCTCCCCCAC CCCGAAACAT GCGCAAATGT GTAACTCTAA AACAATTTAA ATTAATTGGT    7920

CCACGAAGCG CGGGCTCTCG AAGTTTTAAA TTGACTGGTT TGTGATATTT TGAAATGATT    7980

GGTTTGTAAA GCGCGGGCTT TGTTGTGAAC CCCATAAAAG CTGTCCCGAC TCCACACTCG    8040

GGGCCGCAGT CCTCTACCCC TGCGTGGTGT ACGACTGTGG GCCCCAGCGC GCTTGGAATA    8100

AAAATCCTCT TGCTGTTTGC ATCAAAAAAA AA                                 8132
```

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
TGCCTAGAGA CATGTACTC                                                  19
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CCTCTTCTAG CCATTCCTTC A                                               21
```

(2) INFORMATION FOR SEQ ID NO:6:

(i) SEQUENCE CHARACTERISTICS:
        (A) LENGTH: 22 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TCGAGACTCG GTGGAAGGGC CC                                              22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GGGCCCTTCC ACCGAGTCTC GA                                              22

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ACCTGGATCC ATGCATCCCA CG                                              22

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGTGGGATGC ATGGATCCAG GT                                              22

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GGCGCCACCT CCCGATTCGG                                                 20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCGAATCGGG AGGTGGCGCC                                                    20

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

TCCCCTTAAG CTTCGCCTCC                                                    20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

GGAGGCGAAG CTTAAGGGGA                                                    20

(2) INFORMATION FOR SEQ ID NO:14:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

AAAAGCACAA AGGGCAGGAG AGC                                                23

(2) INFORMATION FOR SEQ ID NO:15:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

GCTCTCCTGC CCTTTGTGCT TTT                                                23

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

CCTTTAGGAA CCTGGTGGCC                                                    20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGCCACCAGG TTCCTAAAGG                                      20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CCCCCAGATA TCCTCCATGC                                      20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GCATGGAGGA TATCTGGGGG                                      20

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GCAGTTTCCA ATCAATCCCC AA                                  22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TTGGGGATTG ATTGGAAACT GC                                  22

(2) INFORMATION FOR SEQ ID NO:22:

```
    (i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:22:

TTTATGTTTG CCCAGGACCA CCA                                              23

(2) INFORMATION FOR SEQ ID NO:23:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:23:

TGGTGGTCCT GGGCAAACAT AAA                                              23

(2) INFORMATION FOR SEQ ID NO:24:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:24:

GGGAGGTGGC GCCGGCTTAA CGT                                              23

(2) INFORMATION FOR SEQ ID NO:25:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:25:

ACGTTAAGCC GGCGCCACCT CCC                                              23

(2) INFORMATION FOR SEQ ID NO:26:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:26:

CCCCCAACCC AAGGACCAGG ACCA                                             24

(2) INFORMATION FOR SEQ ID NO:27:

(i) SEQUENCE CHARACTERISTICS:
         (A) LENGTH: 24 base pairs
         (B) TYPE: nucleic acid
         (C) STRANDEDNESS: single
```

(D) TOPOLOGY: linear (ii) MOLECULE TYPE: cDNA (xi) SEQUENCE DESCRIPTION: SEQ ID NO:27:

TGGTCCTGGT CCTTGGGTTG GGGG                                                  24

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GCAGCACGAC TAAAATGGGG GC                                                    22

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GCCCCCATTT TAGTCGTGCT GC                                                    22

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

CCCCCATCCC ACCAACACCT                                                       20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

AGGTGTTGGT GGGATGGGGG                                                       20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

TCTCCCCCAC CCCGAAACAT                                           20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

ATGTTTCGGG GTGGGGGAGA                                           20

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

AGCCAAGAAA GCCAGGTCCC CGAA                                      24

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

TTCGGGGACC TGGCTTTCTT GGCT                                      24

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

AGGCTCTGGT GGCGGGTCTC C                                         21

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GGAGACCCGC CACCAGAGCC T                                         21

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CCGCAGGGAT GGGTTTGGCA                                             20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

TGCCAAACCC ATCCCTGCGG                                             20

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

GCTCACCTGG ACCCGACTGC CC                                        22

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

GGGCAGTCGG GTCCAGGTGA GC                                        22

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GTTTACGGGA CGGGCAGCGA TGGC                                     24

(2) INFORMATION FOR SEQ ID NO:43:

(i) SEQUENCE CHARACTERISTICS:

(A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

GCCATCGCTG CCCGTCCCGT AAAC                                     24

(2) INFORMATION FOR SEQ ID NO:44:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

TGGCTGGGGC GGCGGTGGTG GACGGG                                   26

(2) INFORMATION FOR SEQ ID NO:45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

CCCGTCCACC ACCGCCGCCC CAGCCA                                   26

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GCCCAAAGCC CCAGAACCCA GACG                                     24

(2) INFORMATION FOR SEQ ID NO:47:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

CGTCTGGGTT CTGGGGCTTT GGGC                                     24

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

GATGAACAGG CAGACATCTG                                         20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

CGCTTACAGA CAAGCTGTGA                                         20

(2) INFORMATION FOR SEQ ID NO:50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

AGAACAAAGG CTGGGAAGC                                          19

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

ATAGGAGACA GCCTGAACTC                                         20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

GGACCATTGT CTGACCCTAT                                         20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

GTCAACACCT ATACCAGCTC                                           20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

CATCTGAGGT ATAGCAGGTC                                           20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

GCAGGTGTAG GAACAGGAAC                                           20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

ACCTGTTGAA CCATCCCTCA                                           20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CGAATGGAGA GATCCAGGTA                                           20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

CCTGCATCAC TTCTCTTACC                                           20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

TTGCCTGCTT GTGGAATACG                                                  20

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

CAAGAGAAGA AGTGGGGAAT G                                                21

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

CACAGTCGTA CACCACGCAG                                                  20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

GGGAGACAGA AGAAGAAAGG                                                  20

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

CGATAGTCAT TAGTCCCAGG                                                  20

(2) INFORMATION FOR SEQ ID NO:64:

(i) SEQUENCE CHARACTERISTICS:
        (A) LENGTH: 21 base pairs

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

TGCTGGTTTG CATCAAGACC G                                         21

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

GTCGCAAAGG CATACCTGCT                                           20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

ACAGAGCCTC TGCTAAGAAG                                           20

(2) INFORMATION FOR SEQ ID NO:67:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

GCAGCTGTTG ACAATCATC                                            19

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

TATGAGGAGA GGGCTTGACT                                           20

(2) INFORMATION FOR SEQ ID NO:69:

(i) SEQUENCE CHARACTERISTICS:
        (A) LENGTH: 19 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:69:

AGCAGACGTG CTAGGAGGT                                                19

(2) INFORMATION FOR SEQ ID NO:70:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:70:

TCCTCTTGCT GTTTGCATC                                                19

(2) INFORMATION FOR SEQ ID NO:71:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:71:

CAGACACTCA GAACAGAGAC                                               20

(2) INFORMATION FOR SEQ ID NO:72:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:72:

ACATCGTCTA ACCCACCTAG                                               20

(2) INFORMATION FOR SEQ ID NO:73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:73:

CTCGTTTCTG GTCATACCTG A                                             21

(2) INFORMATION FOR SEQ ID NO:74:

(i) SEQUENCE CHARACTERISTICS:
            (A) LENGTH: 19 base pairs
            (B) TYPE: nucleic acid
            (C) STRANDEDNESS: single
            (D) TOPOLOGY: linear -continued (ii) MOLECULE TYPE: cDNA (xi) SEQUENCE DESCRIPTION: SEQ ID NO:74:

GAGTACATCT CTCTAGGCA 19

MOLECULAR SEQUENCES OF SWINE RETROVIRUSES METHOD OF USING

This application is a continuation-in-part of U.S. Ser. No. 08/572,645, filed Dec. 14, 1995, now abandoned, which is hereby incorporated by reference.

FIELD OF THE INVENTION

The invention relates to porcine retroviral sequences, peptides encoded by porcine retroviral sequences, and methods of using the porcine retroviral nucleic acids and peptides.

BACKGROUND OF THE INVENTION

Advances in solid organ transplantation and a chronic shortage of suitable organ donors have made xenotransplantation an attractive alternative to the use of human allografts. However, the potential for introduction of a new group of infectious diseases from donor animals into the human population is a concern with the use of these methods.

The term applied to the natural acquisition by humans of infectious agents carried by other species is zoonosis. The transplantation of infection from nonhuman species into humans is best termed "direct zoonosis" or "xenosis."

Nonhuman primates and swine have been considered the main potential sources of organs for xenotransplantation (Niekrasz et al. (1992) *Transplant Proc* 24:625; Starzl et al. (1993) *Lancet* 341:65; Murphy et al. (1970) *Trans Proc* 4:546; Brede and Murphy (1972) *Primates Med* 7:18; Cooper et al. In Xenotransplantation: The Transplantation of Organs and Tissues between Species, eds. Cooper et al. (1991) p. 457; R Y Calne (1970) *Transplant Proc* 2:550; H. Auchincloss, Jr. (1988) *Transplantation* 46:1; and Chiche et al. (1993) *Transplantation* 6:1418). The infectious disease issues for primates and swine are similar to those of human donors. The prevention of infection depends on the ability to predict, to recognize, and to prevent common infections in the immunocompromised transplantation recipient (Rubin et al. (1993) *Antimicrob Agents Chemother* 37:619). Because of the potential carriage by nonhuman primates of pathogens easily adopted to humans, ethical concerns, and the cost of maintaining large colonies of primates, other species have received consideration as organ donors (Brede and Murphy (1972) *Primates Med* 7:18; Van Der Riet et al. (1987) *Transplant Proc* 19:4069; Katler In Xenotransplantation: The Transplantation of Organs and Tissues between Species, eds. Cooper et al. (1991) p. 457; Metzger et al. (1981) *J Immunol* 127:769; McClure et al. (1987) *Nature* 330:487; Letvin et al. (1987) *J Infect Dis* 156:406; Castro et al. (1991) *Virology* 184:219; Benveniste and Todaro (1973) *Proc Natl Acad Sci USA* 70:3316; and Teich, in RNA Tumor viruses, eds. Weiss et. al. (1985) p. 25) The economic importance of swine and experience in studies of transplantation in the miniature swine model have allowed some of the potential pathogens associated with these animals to be defined (Niekrasz et al. (1992) *Transplant Proc* 24:625; Cooper et al. In Xenotransplantation: The Transplantation of Organs and Tissues between Species, eds. Cooper et al. (1991) p. 457; and Leman et al. (1992) Diseases of Swine, 7th ed. Ames, Iowa:Iowa State University). Miniature swine have received consideration as organ donors because of a number of features of the species. The structure and function of the main pig organs are comparable to those of man. Swine attain body weights and organ sizes adequate to the provision of organs for human use. Lastly, veterinarians and commercial breeders have developed approaches to creation of specific-pathogen-free (SPF) swine with the ability to eliminate known pathogens from breeding colonies (Alexander et al. (1980) *Proc 6th Int Congr Pig Vet Soc*, Copenhagen; Betts (1961) *Vet Rec* 73:1349; Betts et al. (1960) *Vet Rec* 72:461; Caldwell etal. (1959) *J Am Vet Med Assoc* 135:504; and Yong (1964) *Adv Vet Sci* 9:61).

Concern exists over the transfer of porcine retroviruses by xenotransplantation (Smith (1993) *N Engl J Med* 328:141). Many of the unique properties of the retroviruses are due to the synthesis of a complementary DNA copy from the RNA template (by reverse transcriptase), and integration of this DNA into the host genome. The integrated retroviral copy (which is referred to as an endogenous copy or "provirus") can be transmitted via the germ line.

SUMMARY OF THE INVENTION

In general, the invention features a purified swine or miniature swine retroviral nucleic acid, e.g., a Tsukuba nucleic acid, a purified miniature swine retroviral nucleic acid sequence of SEQ ID NO:1 or its complement, SEQ ID NO:2 or its complement, or SEQ ID NO:3 or its complement, and methods of their use in detecting the presence of porcine, e.g., miniature swine, retroviral sequences.

In another aspect, the invention features a purified nucleic acid, e.g., a probe or primer, which can specifically hybridize with a purified swine or miniature swine retroviral genome, e.g., a Tsukuba genome, the sequence of SEQ ID NO:1 or its complement, SEQ ID NO:2 or its complement, or SEQ ID NO:3 or its complement.

In preferred embodiments the nucleic acid is other than the entire retroviral genome of SEQ ID NO:1 or its complement, SEQ ID NO:2 or its complement, or SEQ ID NO:3 or its complement, e.g., it is at least 1 nucleotide longer, or at least 1 nucleotide shorter, or differs in sequence at at least one position, e.g., the nucleic acid is a fragment of the sequence of SEQ ID NO:1 or its complement SEQ ID NO:2 or its complement, or SEQ ID NO:3 or its complement, or it includes sequence additional to that of SEQ ID NO:1, or its complement, SEQ ID NO:2 or its complement, or SEQ ID NO:3 or its complement.

In preferred embodiments, the nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other embodiments: the sequence of the nucleic acid differs from the corresponding sequence of SEQ ID NO:1 or its complement, SEQ ID NO:2 or its complement, or SEQ ID NO:3 or its complement, by 1, 2, 3, 4, or 5 base pairs; the sequence of the nucleic acid differs from the corresponding sequence of SEQ ID NO:1 or its complement, SEQ ID NO:2 or its complement, or SEQ ID NO:3 or its complement, by at least 1, 2,3,4, or 5 base pairs but less than 6, 7, 8, 9, or 10 base pairs.

In other preferred embodiments: the nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length.

In yet other preferred embodiments: the nucleic acid can specifically hybridize with a translatable region of a miniature swine retroviral genome, e.g., the retroviral genome of SEQ ID NO:1, or its complement, SEQ ID NO:2 or its complement, or SEQ ID NO:3 or its complement, e.g., a region from the gag, pol, or env gene; the probe or primer can specifically hybridize with an untranslated region of a miniature swine retroviral genome, e.g., the retroviral genome of SEQ ID NO:1, or its complement SEQ ID NO:2 or its complement, or SEQ ID NO:3 or its complement; the probe or primer can specifically hybridize with a non-conserved region of a miniature swine retroviral genome, e.g., the retroviral genome of SEQ ID NO:1, or its complement, SEQ ID NO:2 or its complement, or SEQ ID NO:3 or its complement; the probe or primer can specifically hybridize with the highly conserved regions of a miniature swine retroviral genome, e.g., the retroviral genome of SEQ ID NO:1, or its complement, SEQ ID NO:2 or its complement, or SEQ ID NO:3 or its complement.

In preferred embodiments, the primer is selected from the group consisting of SEQ ID NOs:4–74.

In preferred embodiments, hybridization of the probe to retroviral sequences can be detected by standard methods, e.g., by radiolabeled probes or by probes bearing nonradioactive markers such as enzymes or antibody binding sites. For example, a probe can be conjugated with an enzyme such as horseradish peroxidase, where the enzymatic activity of the conjugated enzyme is used as a signal for hybridization. Alternatively, the probe can be coupled to an epitope recognized by an antibody, e.g., an antibody conjugated to an enzyme or another marker.

In another aspect, the invention features a reaction mixture which includes a target nucleic acid, e.g., a human, swine, or a miniature swine nucleic acid, and a purified second nucleic acid, e.g., a probe or primer, as, e.g., is described herein, which specifically hybridizes with the sequence of SEQ ID NO:1 or its complement, SEQ ID NO:2 or its complement, or SEQ ID NO:3 or its complement, a swine or a miniature swine retroviral nucleic acid, e.g., a Tsukuba nucleic acid.

In preferred embodiments, the target nucleic acid: includes RNA; or includes DNA.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a xenogeneic recipient, e.g., a primate, e.g., a human.

In a preferred embodiment: the second nucleic acid is a porcine retroviral sequence, probe or primer, e.g., as described herein, e.g., a Tsukuba-1 retroviral sequence; the second nucleic acid is a sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In preferred embodiments the second nucleic acid is: a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g., from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof.

In another aspect, the invention features a method for screening a cell or a tissue, e.g., a cellular or tissue transplant, e.g., a xenograft, for the presence or expression of a swine or a miniature swine retrovirus or retroviral sequence, e.g., an endogenous miniature swine retrovirus. The method includes:

contacting a target nucleic acid from the tissue with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g., from nucleotides 86–1999) of SEQ ID NO:1, nucleotides 4738–6722 (e.g., from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which hybridization can occur, hybridization being indicative of the presence or expression of an endogenous miniature swine retrovirus or retroviral sequence in the tissue or an endogenous swine retrovirus in the tissue.

In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In preferred embodiments, the tissue or cellular transplant is selected from the group consisting of: heart, lung, liver, bone marrow, kidney, brain cells, neural tissue, pancreas or pancreatic cells, thymus, or intestinal tissue.

In other preferred embodiments, the target nucleic acid is: DNA; RNA; or cDNA.

In other preferred embodiments, the target nucleic acid is taken from: a tissue sample, or a blood sample, e.g., a tissue biopsy sample, e.g., a tissue sample suitable for in situ hybridization or immunohistochemistry.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In a preferred embodiment the target nucleic acid is RNA, or a nucleic acid amplified from RNA in the tissue, and hybridization is correlated with expression of an endogenous miniature swine retrovirus or retroviral sequence or an endogenous swine retrovirus.

In a preferred embodiment the target nucleic acid is DNA, or a nucleic acid amplified from DNA in the tissue, and hybridization is correlated with the presence of an endogenous miniature swine retrovirus or an endogenous swine retrovirus.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of screening a porcine derived cell or tissue for the presence of an activatable porcine retrovirus, e.g., an activatable porcine provirus. The method includes:
stimulating a porcine derived cell or tissue with a treatment which can activate a retrovirus;
contacting a target nucleic acid from the porcine derived cell or tissue with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g., from nucleotides 3112–4683) of SEQ ID NO:1, nucleotides 598–2169 (e.g., from nucleotides 598–2169) of SEQ ID NO:2, or nucleotides 585–2156 (e.g., from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g., from nucleotides 86–1999) of SEQ ID NO:1, nucleotides 4738–6722 (e.g., from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid hybridization being indicative of the presence of an activatable porcine provirus in the porcine derived cell or tissue.

In preferred embodiments the treatment is: contact with a drug, e.g., a steroid or a cytotoxic agent, infection or contact with a virus, the induction of stress, e.g., nutritional stress or immunologic stress, e.g., contact with a T-cell, e.g., a reactive T-cell.

In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In other preferred embodiments, the target nucleic acid is taken from: a tissue sample, or a blood sample, e.g., a tissue biopsy sample, e.g., a tissue sample suitable for in situ hybridization or immunohistochemistry.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a miniature swine genome or a swine genome for the presence of a porcine retrovirus or retroviral sequence, e.g., an endogenous porcine retrovirus. The method includes:

contacting the miniature swine (or swine) genomic DNA with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which the sequences can hybridize, hybridization being indicative of the presence of the endogenous porcine retrovirus or retroviral sequence in the miniature swine (or swine) genome.

In preferred embodiments, the method further includes amplifying all or a portion of the miniature swine (or swine) genome with primers which specifically hybridize to the sequence of SEQ ID NO:1 or its complement, SEQ ID NO:2 or its complement, or SEQ ID NO:3 or its complement.

In a preferred embodiment: the second nucleic acid is a porcine retroviral sequence, probe or primer, e.g., as described herein, e.g., a Tsukuba-1 retroviral sequence; the second nucleic acid is a sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a genetically modified miniature swine or a genetically modified swine for the presence or expression of a miniature swine or swine retrovirus or retroviral sequence, e.g., an endogenous miniature swine retrovirus. The method includes:

contacting a target nucleic acid from the genetically modified miniature swine or swine with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which hybridization can occur, hybridization being indicative of the presence or expression of an endogenous miniature swine retrovirus or retroviral sequence or swine retrovirus or retroviral sequence in the genetically modified miniature swine or swine.

In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of assessing the potential risk associated with the transplantation of a graft from a donor miniature swine or swine into a recipient animal, e.g., a miniature swine or swine, a non-human primate, or a human. The method includes:

contacting a target nucleic acid from the donor, recipient or the graft, with a second sequence chosen from the group of: a nucleic acid sequence which specifically hybridizes a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof;

a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which the sequences can hybridize, hybridization being indicative of a risk associated with the transplantation.

In a preferred embodiment: the second nucleic acid is a Tsukuba-1 retroviral sequence, probe or primer, e.g., as described herein; the second nucleic acid is a porcine retroviral sequence, probe or primer, e.g., as described herein; the second nucleic acid is the sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine potential donor organ; RNA, DNA or cDNA, e.g., cDNA made from an RNA template, isolated from a miniature swine organ which has been transplanted into a organ recipient, e.g.,a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine potential donor organ; RNA, DNA or cDNA, e.g., cDNA made from an RNA template, isolated from a swine organ which has been transplanted into a organ recipient, e.g., a recipient swine or a xenogeneic recipient, e.g., a primate, e.g., a human.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of determining if an endogenous miniature swine or swine retrovirus or retroviral sequence genome includes a mutation which modulates its expression, e.g., results in misexpression. The method includes:

determining the structure of the endogenous retroviral genome, and comparing the structure of the endogenous retroviral genome with the retroviral sequence of SEQ ID NO:1 or its complement, SEQ ID NO:2 or its complement, or SEQ ID NO:3 or its complement, a difference being predictive of a mutation.

In preferred embodiments the method includes sequencing the endogenous genome and comparing it with a sequence from SEQ ID NO:1 or its complement, SEQ ID NO:2 or its complement, or SEQ ID NO:3 or its complement.

In preferred embodiments, the method includes using primers to amplify, e.g., by PCR, LCR (ligase chain reaction), or other amplification methods, a region of the endogenous retroviral genome, and comparing the structure of the amplification product to the sequence of SEQ ID NO:1 or its complement, SEQ ID NO:2 or its complement, or SEQ ID NO:3 or its complement to determine if there is difference in sequence between retroviral genome and SEQ ID NO:1 or its complement, SEQ ID NO:2 or its complement, or SEQ ID NO:3 or its complement. The method further includes determining if one or more restriction sites exist in the endogenous retroviral genome, and determining if the sites exist in SEQ ID NO:1 or its complement, SEQ ID NO:2 or its complement, or SEQ ID NO:3 or its complement.

In preferred embodiments, the mutation is a gross defect, e.g., an insertion, inversion, translocation or a deletion, of all or part of the retroviral genome.

In preferred embodiments, detecting the mutation can include: (i) providing a labeled PCR probe amplified from DNA (e.g., SEQ ID NO:1, SEQ ID NO:2, or SEQ ID NO:3) containing a porcine retroviral nucleotide sequence which hybridizes to a sense or antisense sequence from the porcine retroviral genome(e.g., SEQ ID NO:1, SEQ ID NO:2, or SEQ ID NO:3), or naturally occurring mutants thereof; (ii) exposing the probe/primer to nucleic acid of the tissue (e.g., genomic DNA) digested with a restriction endonuclease; and (iii) detecting by in situ hybridization of the probe/primer to the nucleic acid, the presence or absence of the genetic lesion. Alternatively, direct PCR analysis, using primers specific for porcine retroviral genes (e.g., genes comprising the nucleotide sequence shown in SEQ ID NO:1, SEQ ID NO:2, or SEQ ID NO:3), can be used to detect the presence or absence of the genetic lesion in the porcine retroviral genome by comparing the products amplified.

In another aspect, the invention features a method of providing a miniature swine or a swine free of an endogenous retrovirus or retroviral sequence, e.g., activatable retrovirus, insertion at a preselected site. The method includes:

performing a breeding cross between a first miniature swine (or swine) having a retroviral insertion at the preselected site and a second miniature swine (or swine) not having a retroviral insertion at a preselected site, e.g., the same site, and recovering a progeny miniature swine (or swine), not having the insertion, wherein the presence or absence of the retroviral insertion is determined by contacting the genome of a miniature swine(or swine) with a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO: 1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid.

In preferred embodiments, the nucleic acid is hybridized to nucleic acid, e.g., DNA from the genome, of the first animal or one of its ancestors.

In preferred embodiments, the nucleic acid is hybridized to nucleic acid, e.g., DNA from the genome, of the second animal or one of its ancestors.

In preferred embodiments, the nucleic acid is hybridized to nucleic acid, e.g., DNA from the genome, of the progeny animal or one of its descendants.

In preferred embodiments, the nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the nucleic acid is a full length retroviral genome.

In another aspect, the invention features a method of evaluating a treatment, e.g., an immunosuppressive treatment, for the ability to activate a retrovirus, e.g., an endogenous porcine retrovirus. The method includes:

administering a treatment to a subject, e.g., a miniature swine (or a swine), having an endogenous porcine retrovirus; and detecting expression of the porcine retrovirus with a purified nucleic acid sequence which specifically hybridizes to the sequence of SEQ ID NO:1 or its complement, SEQ ID NO:2 or its complement, or SEQ ID NO:3 or its complement.

In preferred embodiments, the immunosuppresive treatment includes radiation, chemotherapy or drug treatment.

In preferred embodiments: the treatment is one which can induce immunological tolerance; the treatment is one which can introduce new genetic material, e.g., introduce new genetic material into a miniature swine genome (or a swine genome) or into the genome of a host which receives a swine or a miniature swine graft, e.g., the treatment is one which introduces a new genetic material via retroviral mediated transfer.

In a preferred embodiment: the purified nucleic acid is a Tsukuba-1 retroviral sequence, probe or primer, e.g., as described herein; the purified nucleic acid is a porcine retroviral sequence, probe or primer, e.g., as described herein; the purified nucleic acid is the sequence of SEQ ID NO:1 or its complement, SEQ ID NO:2 or its complement, or SEQ ID NO:3 or its complement, or a fragment of such sequence or complement at least 10, 20, or 30, basepairs in length.

In preferred embodiments, the purified nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the purified nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the purified nucleic acid is a full length retroviral genome.

In preferred embodiments the second nucleic acid is: a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g., from nucleotides 3 112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof, a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof.

In another aspect, the invention features a method of localizing the origin of a porcine retroviral infection. The method includes:

contacting a target nucleic acid from the graft with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g., from nucleotides 3112–4683) of SEQ ID NO:1, nucleotides 598–2169 (e.g., from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof;

a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid contacting a target nucleic acid from the recipient with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof, a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid; hybridization to the nucleic acid from the graft correlates with the porcine retroviral infection in the graft; and hybridization to the nucleic acid from the recipient correlates with the porcine retroviral infection in the recipient.

In preferred embodiments, the target nucleic acid includes: genomic DNA, RNA or cDNA, e.g., cDNA made from an RNA template.

In a preferred embodiment: the second nucleic acid is a porcine retroviral sequence, probe or primer, e.g., as described herein, e.g., a Tsukuba-1 retroviral sequence; the second nucleic acid is a sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the recipient is an animal, e.g., a miniature swine, a swine, a non-human primate, or a human.

In preferred embodiments, the graft is selected from the group consisting of: heart, lung, liver, bone marrow or kidney.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of screening a cell, e.g., a cell having a disorder, e.g., a proliferative disorder, e.g., a tumor cell, e.g., a cancer cell, e.g., a lymphoma or a hepatocellular carcinoma, developing in a graft recipient, e.g., a xenograft, for the presence or expression of a porcine retrovirus or retroviral sequence. The method includes:

contacting a target nucleic acid from a tumor cell with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g., from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid, under conditions in which the sample and the nucleic acid sequence can hybridize, hybridization being indicative of the presence of the endogenous porcine retrovirus or retroviral sequence in the tumor cell.

In preferred embodiments, the target nucleic acid from a tumor cell includes: genomic DNA, RNA or cDNA, e.g., cDNA made from an RNA template.

In a preferred embodiment: the second nucleic acid is a porcine retroviral sequence, probe or primer, e.g., as described herein, e.g., a Tsukuba-1 retroviral sequence; the second nucleic acid is a sequence of SEQ ID NO:1 or its complement, SEQ ID NO:2 or its complement, or SEQ ID NO:3 or its complement, or a fragment of the sequence or complement at least 10, 20, or 30, basepairs in length.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method of screening a human subject for the presence or expression of an endogenous porcine retrovirus or retroviral sequence comprising:

contacting a target nucleic acid derived from the human subject with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g., from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4.738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid under conditions in which the sequences can hybridize, hybridization being indicative of the presence of the endogenous porcine retrovirus or retroviral sequence in the human subject.

In preferred embodiments, the target nucleic acid derived from a human subject is DNA, RNA or cDNA sample, nucleic acid from a blood sample or a tissue sample, e.g., a tissue biopsy sample.

In preferred embodiments, the human subject is a miniature swine or swine xenograft recipient, or a person who has come into contact with a miniature swine or swine xenograft recipient.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In preferred embodiments: the recipient is tested for the presence of porcine retroviral sequences prior to implantation of swine or miniature swine tissue.

In another aspect, the invention features a method of screening for viral mutations which modulate, e.g., increase or decrease, susceptibility of a porcine retrovirus to an antiviral agent, e.g., an antiviral antibiotic. The method includes:

administering a treatment, e.g., an antiviral agent, e.g., an antiviral antibiotic;

isolating a putative mutant porcine retroviral strain;

determining a structure of the putative mutant retroviral strain; and comparing the structure to SEQ ID NO:1 or its complement, SEQ ID NO:2 or its complement, or SEQ ID NO:3 or its complement.

In another aspect, the invention features a method of screening for viral mutations which modulate, e.g., increase or decrease, susceptibility of a porcine retrovirus to an antiviral agent, e.g., an antiviral antibiotic. The method includes:

growing the porcine retrovirus in a presence of a treatment, e.g., an antiviral agent, e.g., an antiviral antibiotic; and determine the amount of porcine retroviral DNA synthesized by hybridizing the porcine retroviral DNA to a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156)of SEQ ID NO:3, or naturally occurring mutants thereof, a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof; a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid.

In preferred embodiments, the method further includes amplifying the porcine retroviral nucleic acid with primers which specifically hybridize to the sequence of SEQ ID NO:1 or its complement, SEQ ID NO:2 or its complement, or SEQ ID NO:3 or its complement, e.g., by polymerase chain reaction quantitative DNA testing (PDQ).

In a preferred embodiment: the second nucleic acid is a Tsukuba-1 retroviral sequence, probe or primer, e.g., as described herein; the second nucleic acid is a porcine retroviral sequence, probe or primer, e.g., as described herein;the second nucleic acid is the sequence of SEQ ID NO:1 or its complement, SEQ ID NO:2 or its complement, or SEQ ID NO:3 or its complement.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a porcine-derived product for the presence or expression of a swine or miniature swine retrovirus or retroviral sequence, e.g., an endogenous miniature swine retrovirus. The method includes:

contacting a target nucleic acid from the porcine-derived product with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement; a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof; a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof, a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof, a swine or miniature swine retroviral nucleic acid; or a Tsukuba nucleic acid, under conditions in which hybridization can occur, hybridization being indicative of the presence or expression of an endogenous miniature swine or swine retrovirus or retroviral sequence s in the porcine-derived product.

In preferred embodiments the product is: a protein product, e.g., insulin; a food product; or a cellular transplant, e.g., a swine or miniature swine cell which is to be transplanted into a host, e.g., a swine or miniature swine cell which is genetically engineered to express a desired product, In preferred embodiments, the method further includes amplifying the target nucleic acid with primers which specifically hybridize to the sequence of SEQ ID NO:1 or its complement, SEQ ID NO:2 or its complement, or SEQ ID NO:3 or its complement.

In other preferred embodiments, the target nucleic acid is: DNA; RNA; or cDNA.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a transgenic miniature swine or swine having a transgenic element, e.g., a base change, e.g., a change from A to G, or an insertion or a deletion of one or more nucleotides at an endogenous porcine retroviral insertion site, e.g., a retroviral insertion which corresponds to the retroviral genome of SEQ ID NO:1 or its complement, SEQ ID NO:2 or its complement, or SEQ ID NO:3 or its complement.

In preferred embodiments, the transgenic element is a knockout, e.g., a deletion, insertion or a translocation, of one or more nucleic acids, which alters the activity of the endogenous porcine retrovirus.

In another aspect, the invention features a method of inhibiting expression of an endogenous porcine retrovirus, including: inserting a mutation, e.g. a deletion into the endogenous retrovirus.

In preferred embodiments, the endogenous porcine retrovirus is inactivated.

In preferred embodiments, the mutation can be a point mutation, an inversion, translocation or a deletion of one or more nucleotides of SEQ ID NO:1 or its complement, SEQ ID NO:2 or its complement, or SEQ ID NO:3 or its complement.

In another aspect, the invention features a method of detecting a recombinant virus or other pathogen, e.g., a protozoa or fungi. The method includes:

providing a pathogen having porcine retroviral sequence; and determining if the pathogen includes non-porcine retroviral sequence, the presence of non-porcine retroviral sequence being indicative of viral recombination.

In preferred embodiments, the method further includes determining the structure of a retrovirus by comparing the retrovirus sequence with sequence of SEQ ID NO:1 or its complement, SEQ ID NO:2 or its complement, or SEQ ID NO:3 or its complement, a difference being indicative of viral recombination.

In preferred embodiments, the method further includes comparing the structure of the retrovirus with a human retroviral sequence, e.g., HTLV1, HIV1, or HIV2, a similarity in structure being indicative of viral recombination.

In another aspect, the invention features a method of determining the copy number, size, or completeness of a porcine retrovirus or retroviral sequence, e.g., in the genome of a donor, recipient or a graft. The method includes:

contacting a target nucleic acid from the donor, recipient or a graft, with a second sequence chosen from the group of: a sequence which can specifically hybridize to a porcine retroviral sequence; a sequence which can specifically hybridize to the sequence of SEQ ID NO:1 or its complement; a sequence which can specifically hybridize to the sequence of SEQ ID NO:2 or its complement; a sequence which can specifically hybridize to the sequence of SEQ ID NO:3 or its complement;

a nucleic acid of at least 10 consecutive nucleotides of sense or antisense sequence which encodes a gag protein; a nucleic acid of at least 10 consecutive nucleotides of sense or antisense sequence from nucleotides 2452–4839 (e.g, from nucleotides 3112–4683) of SEQ ID NO:1, nucleotides 598–2169 (e.g, from nucleotides 598–2169) of SEQ ID NO:2, or nucleotides 585–2156 (e.g, from nucleotides 585–2156) of SEQ ID NO:3, or naturally occurring mutants thereof;

a nucleic acid of at least 10 consecutive nucleotides of sense or antisense sequence which encodes a pol protein; a nucleic acid of at least 10 consecutive nucleotides of sense or antisense sequence from nucleotides 4871–8060 of SEQ ID NO:1, nucleotides 2320–4737 of SEQ ID NO:2, or nucleotides 2307–5741 of SEQ ID NO:3, or naturally occurring mutants thereof;

a nucleic acid of at least 10 consecutive nucleotides of sense or antisense sequence which encodes a env protein; a nucleic acid of at least 10 consecutive nucleotides of sense or antisense sequence from nucleotides 2–1999 (e.g, from nucleotides 86–1999) of SEQ ID NO:1, nucleotides 4738–6722 (e.g, from nucleotides 4738–6722) of SEQ ID NO:2, or nucleotides 5620–7533 of SEQ ID NO:3, or naturally occurring mutants thereof; a swine or miniature swine retroviral nucleic acid; or a Tsukuba nucleic acid.

In preferred embodiments, the method further includes amplifying the porcine retroviral nucleic acid with primers which specifically hybridize to the sequence of SEQ ID NO:1 or its complement, SEQ ID NO:2 or its complement, or SEQ ID NO:3 or its complement, e.g., by polymerase chain reaction quantitative DNA testing (PDQ) or nested PCR.

In preferred embodiments, the target nucleic acid includes: genomic DNA isolated from a miniature swine; RNA or cDNA, e.g., cDNA made from an RNA template, isolated from a miniature swine; DNA, RNA or cDNA, e.g., cDNA made from an RNA template, isolated from a miniature swine organ, e.g., a kidney; RNA, DNA or cDNA, e.g., cDNA made from an RNA template, isolated from a miniature swine organ which has been transplanted into a organ recipient, e.g., a xenogeneic recipient, e.g., a primate, e.g., a human.

In preferred embodiments, the target nucleic acid includes: genomic DNA isolated from a swine; RNA or cDNA, e.g., cDNA made from an RNA template, isolated from a swine; DNA, RNA or cDNA, e.g., cDNA made from an RNA template, isolated from a swine organ, e.g., a kidney; RNA, DNA or cDNA, e.g., cDNA made from an RNA template, isolated from a swine organ which has been transplanted into a organ recipient, e.g., a xenogeneic recipient, e.g., a primate, e.g., a human.

In preferred embodiments, the second nucleic acid has at least 60%, 70%, 72%, more preferably at least 85%, more preferably at least 90%, more preferably at least 95%, most preferably at least 98%, 99% or 100% sequence identity or homology with a sequence from SEQ ID NO:1 or its complement, SEQ ID NO:2 or its complement, or SEQ ID NO:3 or its complement.

In other preferred embodiments: the second nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length; the second nucleic acid is a full length retroviral genome.

In another aspect, the invention features a method for screening a tissue, e.g., a cellular or tissue transplant, e.g., a xenograft, or a tissue from a graft recipient, for the presence or expression of a swine or a miniature swine retroviral sequence, e.g., an endogenous miniature swine retrovirus. The method includes: contacting a tissue sample with an antibody specific for a retroviral protein, e.g., an anti-gag, pol, or env antibody, and thereby determining if the sequence is present or expressed.

In preferred embodiments the protein is encoded by a sequence from: the sequence of SEQ ID NO:1 or its complement, SEQ ID NO:2 or its complement, or SEQ ID NO:3 or its complement.

In preferred embodiments, the tissue is selected from the group consisting of: heart, lung, liver, bone marrow, kidney, brain cells, neural tissue, pancreas or pancreatic cells, thymus, or intestinal tissue.

A "purified preparation" or a "substantially pure preparation" of a polypeptide as used herein, means a polypeptide which is free from one or more other proteins, lipids, and nucleic acids with which it naturally occurs. Preferably, the polypeptide, is also separated from substances which are used to purify it, e.g., antibodies or gel matrix, such as polyacrylamide. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 $\mu$g of the polypeptide; at least 1, 10, or 100 mg of the polypeptide.

Specifically hybridize, as used herein, means that a nucleic acid hybridizes to a target sequence with substantially greater degree than it does to other sequences in a reaction mixture. By substantially greater means a difference sufficient to determine if the target sequence is present in the mixture.

A "treatment", as used herein, includes any therapeutic treatment, e.g., the administration of a therapeutic agent or substance, e.g., a drug or irradiation.

A "purified preparation of nucleic acid", is a nucleic acid which is one or both of: not immediately contiguous with one or both of the coding sequences with which it is immediately contiguous (i.e., one at the 5' end and one at the 3' end) in the naturally-occurring genome of the organism from which the nucleic acid is derived; or which is substantially free of a nucleic acid sequence or protein with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional sequences. A purified retroviral genome is a nucleic acid which is substantially free of host nucleic acid or viral protein.

"Homologous", as used herein, refers to the sequence similarity between two polypeptide molecules or between two nucleic acid molecules. When a position in both of the two compared sequences is occupied by the same amino acid or base monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology. The term sequence identity has substantially the same meaning.

The term "provirus" or "endogenous retrovirus," as used herein, refers to an integrated form of the retrovirus.

The terms "peptides", "proteins", and "polypeptides" are used interchangeably herein.

As used herein, the term "transgenic element" means a nucleic acid sequence, which is partly or entirely heterologous, i.e., foreign, to the animal or cell into which it is introduced but which is designed to be inserted, or is inserted, into the animal's genome in such a way as to alter the genome of the cell into which it is inserted. The term includes elements which cause a change in the sequence, or in the ability to be activated, of an endogenous retroviral sequence. Examples of transgenic elements include those which result in changes, e.g., substitutions (e.g., A for G), insertions or deletions of an endogenous retroviral sequence (or flanking regions) which result in inhibition of activation or misexpression of a retroviral product.

As used herein, the term "transgenic cell" refers to a cell containing a transgenic element.

As used herein, a "transgenic animal" is any animal in which one or more, and preferably essentially all, of the cells of the animal includes a transgenic element. The transgenic element can be introduced into the cell, directly or indirectly by introduction into a precursor of the cell, by way of deliberate genetic manipulation, such as by microinjection. This molecule may be integrated within a chromosome, or it may be extrachromosomally replicating DNA.

As described herein, one aspect of the invention features a pure (or recombinant) nucleic acid which includes a miniature swine (or swine) retroviral genome or fragment thereof, e.g., nucleotide sequence encoding a gag-pol or env polypeptide, and/or equivalents of such nucleic acids. The term "nucleic acid", as used herein, can include fragments and equivalents. The term "equivalent" refers to nucleotide sequences encoding functionally equivalent polypeptides or functionally equivalent polypeptides which, for example, retain the ability to react with an antibody specific for a gag-pol or env polypeptide. Equivalent nucleotide sequences will include sequences that differ by one or more nucleotide substitutions, additions or deletions, such as allelic variants, and will, therefore, include sequences that differ from the nucleotide sequence of gag, pol, or env shown in herein due to the degeneracy of the genetic code.

"Misexpression", as used herein, refers to a non-wild type pattern of gene expression, e.g.,porcine retroviral, e.g., Tsukuba-1 gene expression, e.g., gag, pol or env gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing, size, amino acid sequence, post-translational modification, stability, or biological activity of the expressed, porcine retroviral, e.g. Tsukuba-1, polypeptides; a pattern of expression that differs from wild type in terms of the effect of an environmental stimulus or extracellular stimulus on expression of the porcine retroviral, e.g., Tsukuba-1 genes, e.g., a pattern of increased or decreased expression (as compared with wild type) in the presence of an increase or decrease in the strength of the stimulus.

Methods of the invention can be used with swine or miniature swine.

Endogenous retrovirus is a potential source of infection not always susceptible to conventional breeding practices. Many proviruses are defective and unable to replicate. Provirus, if intact, can be activated by certain stimuli and then initiate viral replication using the host's cellular mechanisms. Retroviral infection will often not harm the host cell. However, replication of virus may result in viremia, malignant transformation (e.g., via insertion of retroviral oncogenes), degeneration, or other insertional effects (e.g., gene inactivation). The effects of such infection may not emerge for many years. The spectrum of behavior of active lentiviral infection in humans is well described relative to HIV. These include AIDS, unusual infections and tumors, recombinant and other viruses, and antigenic variation which may prevent the generation of protective immunity by the infected host.

Screening of animals will allow elimination of donors with active replication of known viruses. Inactive proviruses can be detected with genetic probes and removed or inactivated. These novel approaches will allow the identification and elimination of potential human pathogens derived from swine in a manner not possible in the outbred human organ donor population and, thus, will be important to the development of human xenotransplantation.

The porcine retroviral sequences of the invention are also useful as diagnostic probes to detect activation of endogenous porcine retroviruses following transplantation and xenotransplantation of organs derived from swine or miniature swine. The porcine retroviral sequences of the invention also provide diagnostic tools necessary to assess the risks associated with transplantation of organs from swine or miniature swine into human recipients. These sequences are also useful for the longitudinal evaluation of retroviral activation in the human recipient of miniature swine-derived organs.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And*

*Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Although methods and materials similar or equivalent to those described herein can be used in the practice or testing of the present invention, the preferred methods and materials are described below. All publications mentioned herein are incorporated by reference. In addition, the materials, methods, and examples are illustrative only and not intended to be limiting.

DETAILED DESCRIPTION OF THE DRAWINGS

DETAILED DESCRIPTION

Miniature Swine Retroviruses

Figure 1:
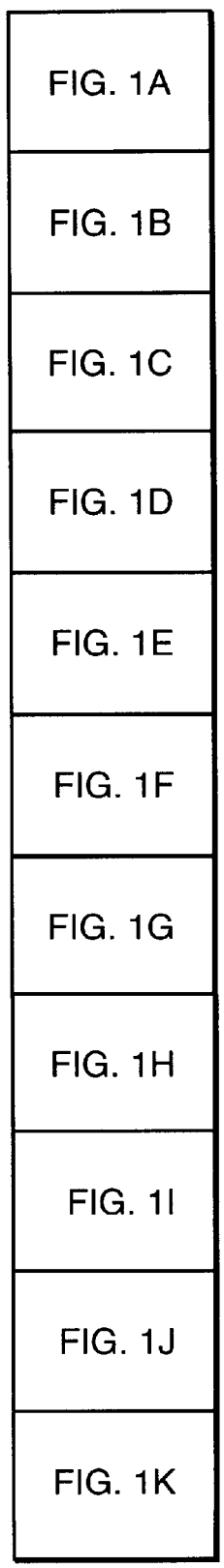
FIG. 1 is the nucleotide sequence (SEQ ID NO:1) of the Tsukuba-1 cDNA.
Figure 2:
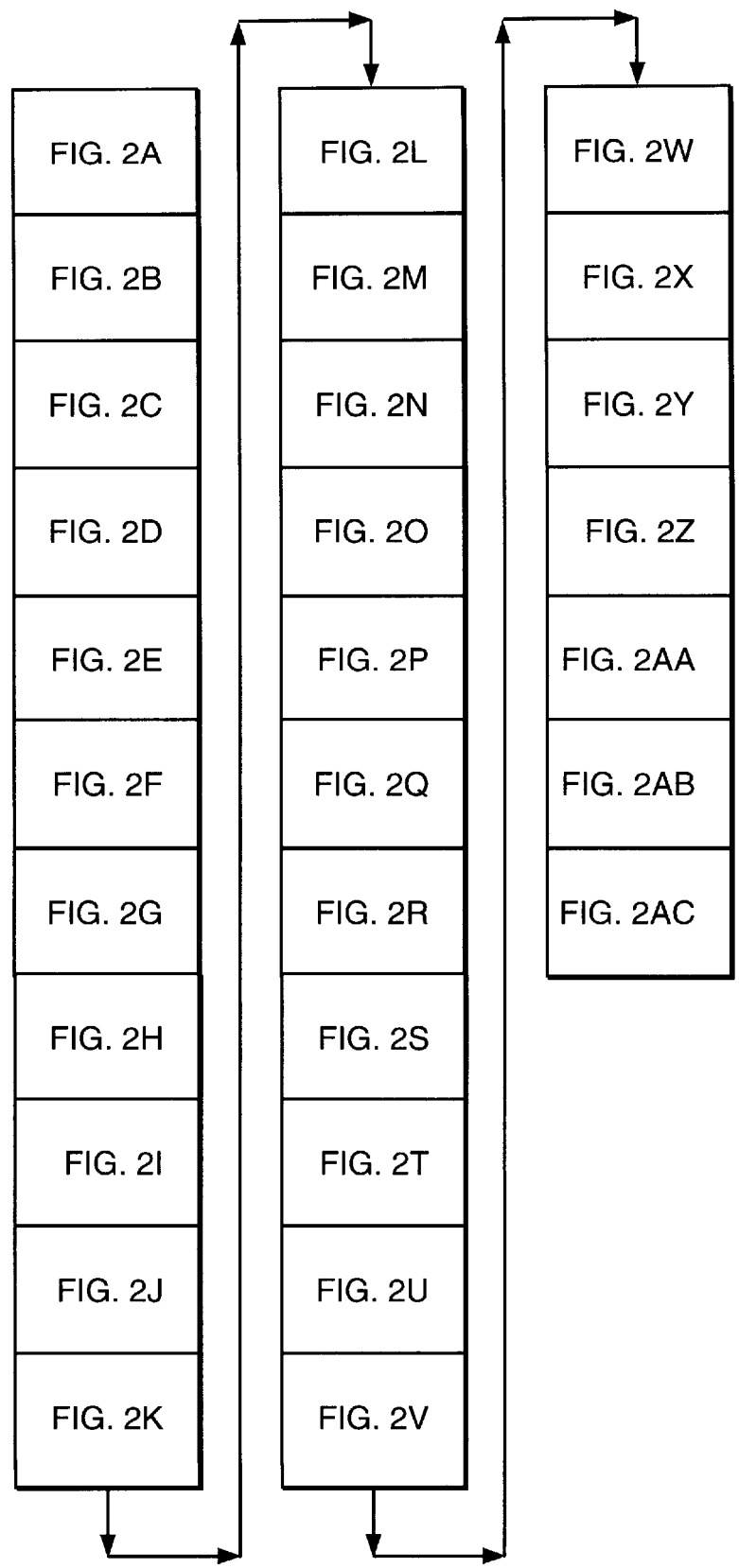
FIG. 2 is the nucleotide sequence (SEQ ID NO:2) of a defective retroviral genome isolated from the retrovirus from the PK-15 cell line.
Figure 3:
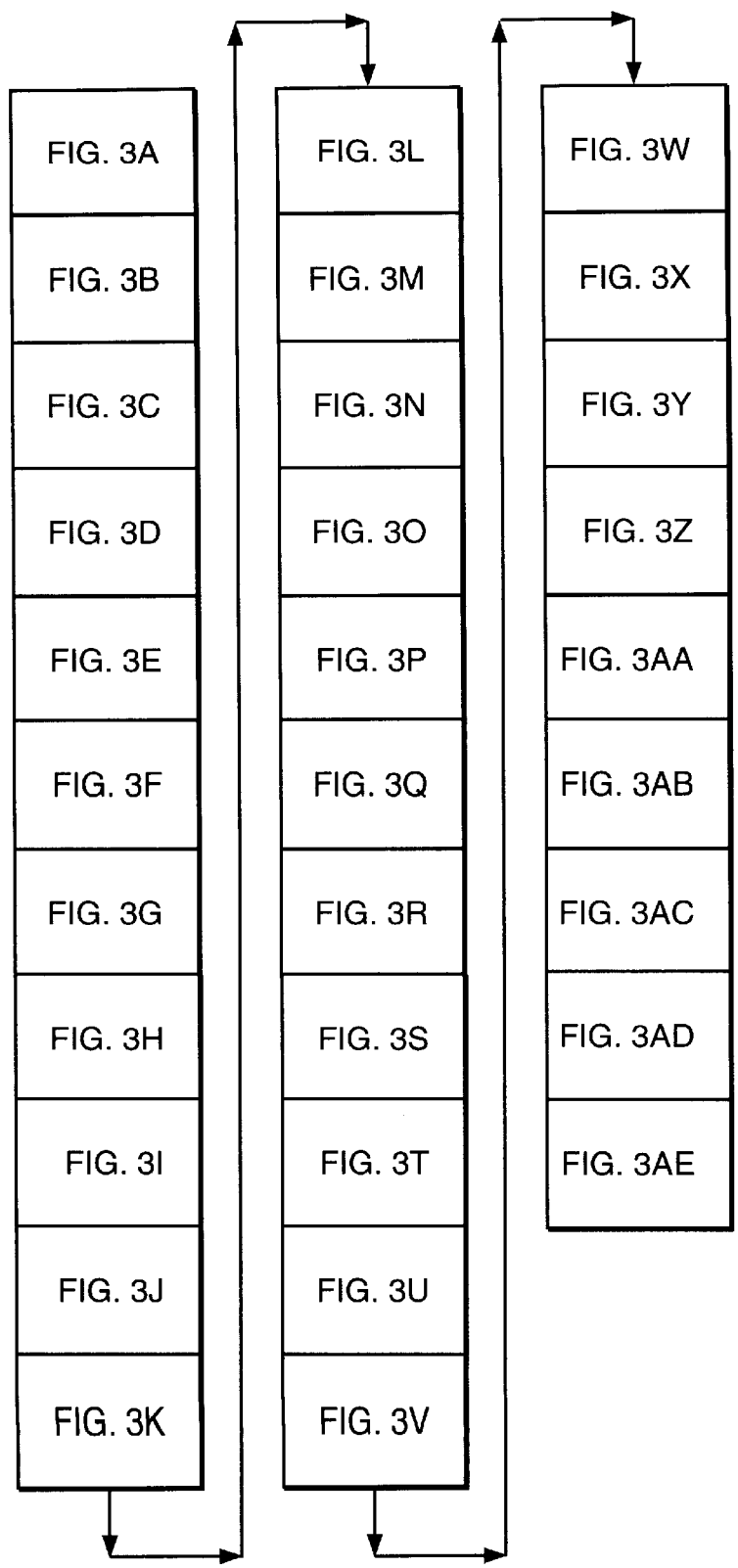
FIG. 3 is the nucleotide sequence (SEQ ID NO:3) of a retrovirus found in miniature swine.

Transplantation may increase the likelihood of retroviral activation, if intact and infectious proviruses are present. Many phenomena associated with transplantation, e.g., immune suppression, graft rejection, graft-versus-host disease, viral co-infection, cytotoxic therapies, radiation therapy or drug treatment, can promote activation of retroviral expression.

Many species are thought to carry retroviral sequences in their genomic DNA. The number of intact (complete) retroviral elements that could be activated is often unknown. Once activated, swine-derived viruses would require the appropriate receptor on human tissues to spread beyond the transplanted organ. Most intact endogenous proviruses (usually types B and C), once activated, are not pathogenic. However, coinfection with other viruses, recombination with other endogenous viruses, or modification of viral behavior in the foreign human environment may alter the pathogenicity, organ specificity or replication of the retroviruses or other infectious agents.

The lack of sequence data on pig viruses has impeded efforts to assess the number of porcine sequences, or porcine retroviral sequences, that have incorporated into the human genome or the frequency of incorporation.

The inventor, by showing that the Tsukuba-1 retrovirus is found in miniature swine, and by providing the entire sequence of the porcine retroviral (Tsukuba-1) genome, has allowed assessment of the risk of endogenous retroviruses in general clinical practice and more importantly in xenotransplantation.

The porcine retroviral sequences of the invention can be used to determine the level (e.g., copy number) of intact (i.e., potentially replicating) porcine provirus sequences in a strain of xenograft transplantation donors. For example, the copy number of the miniature swine retroviral sequences can be determined by the Polymerase Chain Reaction DNA Quantitation (PDQ) method, described herein, or by other methods known to those skilled in the art. This quantitation technique will allow for the selection of animal donors, e.g., miniature swine donors, without an intact porcine retroviral sequence or with a lower copy number of viral elements.

The porcine retroviral sequences of the invention can be used to determine if mutations, e.g., inversions, translocations, insertions or deletions, have occurred in the endogenous porcine retroviral sequence. Mutated viral genomes may be expression-deficient. For example, genetic lesions can be identified by exposing a probe/primer derived from porcine retrovirus sequence to nucleic acid of the tissue (e.g., genomic DNA) digested with a restriction endonucleases or by in situ hybridization of the probe/primer derived from the porcine retroviral sequence to the nucleic acid derived from donor, e.g., miniature swine, tissue. Alternatively, direct PCR analysis, using primers specific for porcine retroviral genes (e.g., genes comprising the nucleotide sequence shown in SEQ ID NO:1, 2, or 3), can be used to detect the presence or absence of the genetic lesion in the porcine retroviral genome.

Miniature swine retroviral sequences of the invention can also be use to detect viral recombinants within the genome, or in the circulation, cells, or transplanted tissue, between the porcine retrovirus and other endogenous human viruses or opportunistic pathogens (e.g. cytomegalovirus) of the immunocompromised transplant recipient. For example, pieces of the viral genome can be detected via PCR or via hybridization, e.g., Southern or Northern blot hybridization, using sequences derived from SEQ ID NO:1, 2, or 3 as primers for amplification or probes for hybridization.

Miniature swine retroviral sequences of the invention, e.g., PCR primers, allow quantitation of activated virus. Sequences of the invention also allow histologic localization (e.g., by in situ hybridization) of activated retrovirus. Localization allows clinicians to determine whether a graft should be removed as a source of potential retroviral infection of the human host or whether the retroviral infection was localized outside the graft.

Sequences of the invention, e.g., PCR primers, allow the detection of actively replicating virus, e.g., by using reverse transcribed PCR techniques known in the art. Standard techniques for reverse transcriptase measurements are often complicated, species-specific, and are of low sensitivity and specificity, and false positive results may develop using full-length probes for Southern and Northern molecular blotting. Sequences of the invention allow for sensitive and specific assays for the activation of virus and this will allow performance of a wide variety of tests, some of which are outlined below.

The invention provides for the testing and development of donor animals having reduced numbers of intact proviral insertions. It also provides for the testing of immunosuppressive regimens less likely to provide the conditions for active replication of retrovirus. Conditions likely to activate one retrovirus are generally more likely to activate other viruses including unknown retroviruses and known human pathogens including cytomegalovirus, hepatitis B and C viruses, Human Immunodeficiency Viruses (I and II). Given the availability of preventative therapies for these infections, these therapies could be used prophylactically in patients known to be susceptible to the activation of porcine retrovirus.

The miniature swine retroviral sequences of the invention can be used to measure the response of the miniature swine retroviral infection in humans to therapy, e.g., immunomodulatory or antiviral therapy, e.g., antiviral agents, e.g., antiviral antibiotics. With HIV, susceptibility to antiviral antibiotics is determined by the genetic sequence of the reverse transcriptase gene (RT pol region) and other genes. The ability to determine the exact sequence of the retroviral genes will allow the detection of mutations occurring during infection which would then confer resistance of this virus to antiviral agents. Primers, e.g., for the RT-pol region, of the invention can be used to detect and to sequence clinical viral isolates from patients which have developed mutations by PDQ method described herein. The primers of the invention can also be used to determine whether tumor cells, e.g., cancer cells, e.g. lymphoma or hepatocellular carcinoma, developing in xenograft recipients contain porcine retroviral elements.

The porcine retroviral sequences of the invention can also be used to detect other homologous retroviruses and to determine whether these are the same or different as compared to the Tusukuba-1 retroviral sequences. For example, within a species, the polymerase genes are highly conserved. PCR assays aimed at the gag-pol region followed by sequence analysis allow for this detection of homologous viruses. The appropriate regions of the Tsukuba-1 virus can be determined by using sequences derived from SEQ ID NO:1, described herein, to identify additional 5' and 3' viral genomic sequences. As is discussed elsewhere herein, the sequences from SEQ ID NO:1 were used to obtain the sequence of the PK-15 retroviral insert (SEQ ID NO:2) and of a retroviral insertion in a miniature swine (SEQ ID NO:3).

Miniature swine retroviral sequences of the invention can be used to screen donor animals and xenograft recipients after transplantation both for infection, and as a measure of the appropriate level of immune suppression, regarding susceptibility to infection. Physicians, medical staff, family, or individuals who come into contact with graft recipients, and others, can be screened for infection with virus derived from the xenograft recipient. Members of the population in general can also be screened. Such screening can be used for broad epidemiologic studies of the community. These methods can help in meeting the requirements of the F.D.A. regarding enhancing the safety of the recipients and of the community to exposure to new viruses introduced into the community by xenograft transplantation.

As is shown in Suzuka et al., 1986, FEBS 198:339, the swine retroviruses such as the Tsukuba-1 genome can exist as a circular molecule. Upon cloning the circular molecule is generally cleaved to yield a linear molecule. As will be understood by one skilled in the art, the start point and end point of the resulting linear molecule, and the relative subregions of the viral sequence will of course vary with the point of cleavage. For example, in the Suzuka et al. reference the LTR is shown to be in an internal fragment. This is indicated herein in that the order of gag, pol, env in SEQ ID NO 1 is shown as env, gag, pol, while elsewhere herein the order of these regions is given as the naturally occurring gag, pol, env order.

Primers Derived from the Porcine Retroviral (Tsukuba-1) Genome Sequence

A number of different primers useful in the methods of the invention have been described herein. One skilled in the art can identify additional primers from the viral sequence of SEQ ID NO:1 by using methods known in the art. For example, when trying to identify potentially useful primers one skilled in the art would look for sequences (sequences should be between about 15 and 30 nucleotides in length) which hybridize to SEQ ID NO:1 with high melting temperature; have a balanced distribution of nucleotides, e.g., a balanced distribution of A, T, C and Gs; have a terminal C or G; do not self-hybridize or internally complement.

Use of Primers Derived from the Porcine Retroviral (Tsukuba-1) Genome Sequence

I. Testing of Organs or Cells Prior to Transplantation

Potential donor animals can be screened for active retroviral replication prior to being used in transplantation. This allows avoidance of animals undergoing active viral replication. Replicating virus is often infectious in 100% of recipients, while nonreplicating, latent provirus generally causes infection in 5 to 25% of recipients.

II. Testing of Recipients

Serial samples, e.g., of white blood cells, can be obtained from a graft recipient monthly, e.g., for the first month and every three months thereafter. Tissue biopsies obtained for evaluation of graft function can be used to evaluate the activation of retroviral sequences or of the expression retroviral sequences in graft tissue. Samples can be screened for the presence of retrovirus infection both specifically for the homologous virus, for viral recombinants containing portions of the viral genome, and for other retroviruses, using, e.g., PCR primers for the pol region of the virus, which is the region most likely to be conserved. If virus is detected, quantitative PCR can be used to determine the relative stability of viral production. Cells isolated from xenograft recipients can be tested by cocultivation with permissive human and porcine (e.g., pig fallopian tube, pig macrophage, or pig testis) cell lines known to contain endogenous viruses. Isolated virus will be tested for homology with the parental strain and for mutations which might affect susceptibility to antiviral agents, e.g., antiviral antibiotics.

III. Testing of Surgical and Medical Personnel and Family Members of Graft Recipient Samples, e.g., white blood cells, can be banked (archived) from the surgical and medical personnel and from family members of the recipient prior to transplantation and at three months intervals for the first year and at least annually thereafter. Epidemiologic studies can be performed on these samples as well. These samples can be tested if the recipient becomes viremic or if unusual clinical manifestations are noted in these individuals.

IV. Testing of Tumor Cells

Tumor cells which develop from a graft, or a graft recipient, can be tested for the presence of active retrovirus and for proviruses.

V. Testing of Patients

Patients can be retested for any significant change in clinical condition or for increased immune suppression of graft rejection which may be associated with an increased risk of viral activation.

Sequencing of the Porcine Retroviral (Tsukuba-1) Genome

A clone (Pλ8.8) containing the 8060 bp XhoI porcine retrovirus (Tsukuba-1) insert was used to transfect competent *E. coli*, and DNA was isolated for sequencing. The strategy used to sequence the 8060 bp porcine retrovirus genome included a combination of procedures which are outlined below.

Random fragments (1–3 kb) of the clone (Pλ8.8) were generated by sonication. The fragments were blunt-ended and were subcloned into the EcoRV site of the pBluescript SK vector. Plasmid DNA was prepared using a modified alkaline lysis procedure. DNA sequencing was performed using DyeDeoxy termination reactions (ABI). Base specific fluorescent dyes were used as labels. Sequencing reactions were analyzed on 4.75% polyacrylamide gels by an ABI 373A-S or 373S automated sequencer. Subsequent data analysis was performed on Sequencer™ 3.0 software. The following internal sequencing primers were synthesized:

```
AP1    5'  GATGAACAGGCAGACATCTG   3'  (SEQ ID NO:48)
AP2    5'  CGCTTACAGACAAGCTGTGA   3'  (SEQ ID NO:49)
AP3    5'  AGAACAAAGGCTGGGAAAGC   3'  (SEQ ID NO:50)
AP4    5'  ATAGGAGACAGCCTGAACTC   3'  (SEQ ID NO:51)
AP5    5'  GGACCATTGTCTGACCCTAT   3'  (SEQ ID NO:52)
AP6    5'  GTCAACACCTATACCAGCTC   3'  (SEQ ID NO:53)
AP7    5'  CATCTGAGGTATAGCAGGTC   3'  (SEQ ID NO:54)
AP8    5'  GCAGGTGTAGGAACAGGAAC   3'  (SEQ ID NO:55)
AP9    5'  ACCTGTTGAACCATCCCTCA   3'  (SEQ ID NO:56)
AP10   5'  CGAATGGAGAGATCCAGGTA   3'  (SEQ ID NO:57)
AP11   5'  CCTGCATCACTTCTCTTACC   3'  (SEQ ID NO:58)
AP12   5'  TTGCCTGCTTGTGGAATACG   3'  (SEQ ID NO:59)
AP13   5'  CAAGAGAAGAAGTGGGGAATG  3'  (SEQ ID NO:60)
AP14   5'  CACAGTCGTACACCACGCAG   3'  (SEQ ID NO:61)
AP15   5   GGGAGACAGAAGAAGAAAGG   3'  (SEQ ID NO:62)
AP16   5'  CGATAGTCATTAGTCCCAGG   3'  (SEQ ID NO:63)
AP17   5'  TGCTGGTTTGCATCAAGACCG  3'  (SEQ ID NO:64)
AP18   5'  GTCGCAAAGGCATACCTGCT   3'  (SEQ ID NO:65)
AP19   5'  ACAGAGCCTCTGCTAAGAAG   3'  (SEQ ID NO:66)
AP20   5'  GCAGCTGTTGACAATCATC    3'  (SEQ ID NO:67)
AP21   5'  TATGAGGAGAGGGCTTGACT   3'  (SEQ ID NO:68)
AP22   5'  AGCAGACGTGCTAGGAGGT    3'  (SEQ ID NO:69)
AP23   5'  TCCTCTTGCTGTTTGCATC    3'  (SEQ ID NO:70)
AP24   5'  CAGACACTCAGAACAGAGAC   3'  (SEQ ID NO:71)
AP25   5'  ACATCGTCTAACCCACCTAG   3'  (SEQ ID NO:72)
AP26   5'  CTCGTTTCTGGTCATACCTGA  3'  (SEQ ID NO:73)
AP27   5'  GAGTACATCTCTCTAGGCA    3'  (SEQ ID NO:74)
AP28   5'  TGCCTAGAGACATGTACTC    3'  (SEQ ID NO:4)
AP29   5'  CCTCTTCTAGCCATTCCTTCA  3'  (SEQ ID NO:5)
```

The clone (Pλ8.8) containing the 8060 bp XhoI porcine retrovirus (Tsukuba-1) insert was deposited with ATCC on Dec. 27, 1995 (ATCC Deposit No.97396).

Determination of the Porcine Retroviral (Tsukuba-1) Copy Number in a Miniature Swine Total genomic DNA was isolated from miniature swine kidney by the methods known in the art. The isolated genomic DNA was digested with either EcoRI or HindIII restriction enzyme. The DNA digests were electrophoresed on an agarose gel, Southern blotted and hybridized to the full-length, purified, Tsukuba-1 sequence (SEQ ID NO:1) under high stringency conditions (0.1×SSC, 65° C.). In both digested samples (EcoRI or HindIII) at least six copies of the high molecular fragments of the miniature swine genome (over 16 Kb in size) hybridized to SEQ ID NO:1, indicating the presence of homologous retroviral sequences in porcine DNA.

Susceptibility Testing by Polymerase Chain Reaction DNA Quantitation (PDQ)

Polymerase chain reaction (PCR) DNA quantitation (PDQ) susceptibility testing can be used to rapidly and directly measure nucleoside sensitivity of porcine retrovirus isolates. PCR can be used to quantitate the amount of porcine retroviral RNA synthesized after in vitro infection of peripheral blood mononuclear cells. The relative amounts of porcine retroviral RNA in cell lysates from cultures maintained at different drug concentrations reflect drug inhibition of virus replication. With the PDQ method both infectivity titration and susceptibility testing can be performed on supernatants from primary cultures of peripheral blood mononuclear cells.

The PDQ experiments can be performed essentially as described by Eron et al., PNAS USA 89:3241–3245, 1992. Briefly, aliquots (150µl) of serial dilutions of virus sample can be used to infect 2×10$^6$ PHA-stimulated donor PBMCs in 1.5 ml of growth medium per well of a flat-bottom 24-well plate (Coming). Separate cell samples can be counted, harvested, and lysed at 48, 72 and 96 hr. Quantitative PCR and porcine retrovirus copy-number determination can then be performed in duplicate on each lysate.

The results of a PDQ infectivity titration assay can be used to determine the virus dilution and length of culture time employed in a subsequent PDQ susceptibility test. These parameters should be chosen so that the yield of porcine retrovirus specific PCR product for the untreated control infection would fall on the porcine retrovirus copy-number standard curve before the curve approached its asymptotic maximum, or plateau. PHA-stimulated donor PBMCs can be incubated with drug for 4 hr prior to infection. Duplicate wells in a 24-well plate should receive identical porcine retrovirus inocula for each drug concentration tested and for the untreated infected controls. Uninfected controls and drug toxicity controls should be included in each experiment. All cultures can be harvested and cells lysed for PCT after either 48 or 72 hr. Previously characterized isolates can be used as assay standards in each experiment.

Cell pellets can be lysed in various volumes of lysis buffer (50 mM KCl/10 mM Tris•HCl, pH 8.3/2.5 mM MgCl$_2$/0.5% Nonidet P-40/0.5% Tween 20/0.01% proteinase K) to yield a concentration of 1.2×10$^4$ cell equivalents/µl. Uniformity to cell lysate DNA concentrations should be confirmed in representative experiments by enhancement of Hoechst 33258 fluorescence (Mini-Fluorometer, Hoefer).

A conserved primer pair can be synthesized according to the pol gene sequences. The primers can than be used to amplify a 1580-base pair fragment of the porcine retrovirus pol gene from 1.2×10$^5$ cell equivalents of lysate by using PCR (GeneAmp, Cetus) under standard conditions. Amplifications should be repeated if porcine retrovirus DNA is amplifiable from reagent controls.

Porcine retrovirus pol gene amplification products can be specifically detected and quantitated as described (Conway, B.C. (1990) in Techniques in HIV Research, (Aldovani & Walker, eds.) (Stockton, N.Y.) pp.40–46). Heat-denatured PCR products can be hybridized in a Streptavidin-coated microtiter plate well with both biotinylated capture probe and horseradish peroxidase (HRP)-labeled detector probe [enzyme-linked oligonucleotide solution sandwich hybridization assay ((ELOSA), DuPont Medical Products, Billerica, Mass.) for 60 min at 37° C. After extensive washing to remove all reactants except probe-DNA hybrids, an HRP chromogen, tetramethylbenzidine (TMBlue, Transgenic Sciences, Worcester, Mass.), should be added to each well. The HRP-catalyzed color development should be stopped after 1 hr by addition of sulfuric acid to 0.65 M. Absorbance (OD) at 450 nm can be measured in an automated microtiter plate reader (SLT Labinstruments, Hillsborough, N.C.).

A standard curve of porcine retrovirus DNA copy number can be generated in each PCR by using a dilution series of cells containing one porcine proviral genome per cell.

Preparation of a Miniature Swine Having a Knockout of Tsukuba-1 Viral Sequence Using Isogenic DNA Targeting Vectors Isogenic DNA, or DNA that is substantially identical in sequence between the targeting vector and the target DNA in the chromosomes, greatly increases the frequency for homologous recombination events and gene targeting efficiency. Using isogenic-DNA targeting vectors, targeting frequencies of 80% or higher can be achieved in mouse embryonic stem cells. This is in contrast to non-isogenic DNA vectors which normally yield targeting frequencies of around 0.5% to 5%. i.e., approximately two orders of magnitude lower than isogenic DNA vectors. Isogenic DNA constructs are predominantly integrated into chromosomes by homologous recombination rather than random integration. As a consequence, targeted mutagenesis of viral sequences, e.g., viral genes, can be carried out in biological systems including zygotes, which do not lend themselves to the use of elaborate selection protocols, resulting in production of animals, e.g., miniature swine, free of, or having a reduced number of, activatable viral sequences. In order for the isogenic DNA approach to be feasible, targeting vectors should be constructed from a source of DNA that is identical to the DNA of the organism to be targeted. Ideally, isogenic DNA targeting is carried out in inbred strains of animals, e.g., inbred miniature swine, in which all genetic loci are homozygous. Any animal of that strain can serve as a source for generating isogenic targeting vectors. This protocol for isogenic gene targeting is outlined in TeRiele et al., PNAS 89:5128–5132, 1992 and PCT/US92/07184, herein incorporated by reference. A protocol for producing Tsukuba-1 knockout miniature swine is described briefly below.

An insertion vector is designed as described by Hasty and Bradley (Gene Targeting Vectors for Mammalian Cells, in Gene Targeting: A Practical Approach, ed, Alexandra L. Joyner, IRL Press 1993). Insertion vectors require that only one crossover event occur for integration by homologous recombination into the native locus. The double strand breaks, the two ends of the vector which are known to be highly recombinogenic, are located on adjacent sequences on the chromosome. The targeting frequencies of such constructions will be in the range of 30 to 50%. One disadvantage of insertion vectors, in general, concerns the sequence duplications that are introduced and that potentially make the locus unstable. All these constructions are made using standard cloning procedures.

Replacement vectors have also been extensively described by Hasty and Bradley. Conceptually more straight forward than the insertion vector, replacement vectors use an essentially co-linear fragment of a stretch of Tsukuba-1 genomic sequence. Preferably, the DNA sequence from which an isogenic replacement vector is constructed includes approximately 6 to 10 kb of uninterrupted DNA. Two crossovers, one on either side of the selectable marker causes the mutant targeting vector to become integrated and replace the wild-type gene.

Microinjection of the isogenic transgene DNA into one of the pronuclei of a porcine embryo at the zygote stage (one-cell embryo) is accomplished by modification of a protocol described earlier (Hammer et al. 1985, Nature 315, 680; Pursel et al. 1989, Science 244, 1281). The age and the weight of the donor pigs, e.g., haplotype specific miniswine, are critical to success. Optimally, the animals are of age 8 to 10 months and weigh 70 to 85 lbs. This increases the probability of obtaining an adequate supply of one-cell embryos for microinjection of the transgenes. In order to allow for accurate timing of the embryo collections at this stage from a number of embryo donors, the gilts are synchronized using a preparation of synthetic progesterone (Regumate). Hormone implants are applied to designated gilts 30 days prior to the date of embryo collection. Twenty days later, ten days prior to the date of collection, the implants are removed and the animals are treated with additional hormones to induce superovulation to increase the number of embryos for microinjection. Three days following implant removal, the animals are treated with 400 to 1000 IU of pregnant mare serum gonadotropin (PMSG) and with 750 IU of human chorionic gonadotropin (hCG) three to four days later. These animals are bred by artificial insemination (AI) on two consecutive days Following injection of hCG.

Embryo collections are performed as follows: three days following the initial injection of hCG, the animals are anesthetized with an intramuscular injection of Telazol (3 mg/lb), Rompum (2 mg/lb) and Atropine (1 mg/lb). A midline laparotomy is performed and the reproductive tract exteriorized. Collection of the zygotes is performed by cannulating the ampulla of the oviduct and flushing the oviduct with 10 to 15 ml phosphate buffered saline, pre-warmed to 39° C. Following the collection the donor animals are prepared for recovery from surgery according to USDA guidelines. Animals used twice for embryo collections are euthanized according to USDA guidelines.

Injection of the transgene DNA into the pronuclei of the zygotes is carried out as summarized below: Zygotes are maintained in medium HAM F-12 supplemented with 10% fetal calf serum at 38° C. in 5% $CO_2$ atmosphere. For injection the zygotes are placed into BMOC-2 medium, centrifuged at 13,000 g to partition the embryonic lipids and visualize the pronuclei. The embryos are placed in an injection chamber (depression slide) containing the same medium overlaid with light paraffin oil. Microinjection is performed on a Nikon Diaphot inverted-microscope equipped with Nomarski optics and Narishige micromanipulators. Using 40× lens power the embryos are held in place with a holding pipette and injected with a glass needle which is back-filled with the solution of DNA containing the transgenic element, e.g., a mutant viral gene (2 μg/ml). Injection of approximately 2 picoliters of the solution (4 femptograms of DNA), which is equivalent to around 500 copies of the transgenic element. e.g., a mutant viral gene, is monitored by the swelling of the pronucleus by about 50%. Embryos that are injected are placed into the incubator prior to transfer to recipient animals.

Recipient animals are prepared similarly to the donor animals, but not superovulated. Prior to the transfer of the injected embryos, recipient gilts are anesthetized, the abdomen opened surgically by applying a longitudinal incision and the ovaries exteriorized. The oviduct ipsilateral to the ovary with the larger number of corpus lutei is flushed, the embryos checked to evaluate if the animals is reproductively sound. Approximately 4 to 6 zygotes injected with the transgenic element, e.g., a mutant viral gene, are transferred to the flushed oviduct, the abdominal incision sutured and the animals placed in a warm area for recovery. The status of the pregnancy is monitored by ultrasound starting at day 25, or approximately one week following the expected date of implantation. Pregnant recipients are housed separately until they are due to farrow.

Newborn piglets are analyzed for integration of the transgenic element into chromosomal DNA. Genomic DNA is extracted from an ear punch or a blood sample and initial screening is performed using PCR. Animals that are potentially transgenic element-positive are confirmed by Southern analysis. Transgenic founder animals are subjected to further analysis regarding the locus of transgenic element integration using Southern analysis.

The Isolation and Sequencing of an Endogenous Swine Retroviral Insert and of a Retroviral Insert in Porcine PK-15 Cells Cloning of PK15 and PAL Endogenous Retroviruses I. Poly $A^+$RNA Isolation Peripheral blood lymphocytes (PBLs) were prepared from haplotype d/d miniswine using standard protocols known in the art. The PBLs were cultured in the presence of 1% phytohemagglutinin (PHA) for about 84 hours. The activated PBLs were collected and total RNA was isolated using commercially available kits, such at Gentra's (Minneapolis, Minn.) PUREscript Kit. Poly A+RNA was isolated from the total RNA using another commercially available product, Dynal Dynabeads (Lake Success, N.Y.). Northern analysis of the RNA using a pig retroviral probe confirmed the presence of potentially full-length retroviral genome RNA. RNA from PK1 5 cells was isolated using similar protocols.

II. Construction of the cDNA Libraries

Using Superscript Choice System (Life Technologies Ltd, Gibco BRL, Gaithersburg, Md.) for cDNA Synthesis, a cDNA library was constructed using oligo dT to make the first strand cDNA. The use of Superscript reverse transcriptase was important in order to obtain full-length retroviral (RV) cDNAs, due to the length of the RV RNA. The cDNA library was enriched for large cDNA fragments by size selecting >4 kb fragments by gel electrophoresis. The cDNAs were cloned into Lambda ZAP Express (Clontech Laboratories, Inc. Palo Alto, Calif.), which is one of the few commercially available cDNA vectors that would accept inserts in the 1–12kb range.

III. Screening of the cDNA Libraries $0.75–1.2 \times 10^6$ independent clones were screened using either gag and pol or gag and env probes. Double positive clones were further purified until single isolates were obtained (1 or 2 additional rounds of screening).

IV. Characterization of the Clones

Between 18 and 30 double positive clones were selected for evaluation. Lambda DNA was prepared using standard protocols such as the Lambda DNA Kit (Qiagen Inc., Chatsworth, Calif.). The clones were analyzed by PCR to check for (a) RV genes, and (b) determine the size of insert and LTR regions. Restriction digests were also done to confirm the size of insert and to attempt to categorize the clones. Clones containing the longest inserts and having consistent and predicted PCR data were sequenced.

Development of a PCR-Based Assay for the Detection of the Presence of an Endogenous Retrovirus in Cells, Tissues, Organs, Miniswine or Recipient hosts (e.g., Primates, Humans)

Using a commercially available computer software program (such as RightPrimer, Oligo 4.0, MacVector or Geneworks), one can analyze sequences disclosed herein for the selection of PCR primer pairs. The criteria for the general selection of primer pairs includes:

a. The Tm of each primer is between 65–70° C.
b. The Tm's for each pair differ by no more than 3° C.
c. The PCR fragment is between 200–800 bp in length
d. There are no repeats, self complementary bases, primer-dimer issues, etc for each pair A. Additional criteria for: A pig-specific PCR assay
a. Primers are selected within porcine-specific regions of the sequence—such as within gag, env, or U3. Porcine-specific primers are defined as sequences which overall have <70% homology to the corresponding region in human, mouse and primate retroviruses. In addition, the last five bases at the 3' end of the primer should be unique to the pig retroviral sequence.
b. Primers should have no more than one or two mismatched bases based on the miniswine, and retroviral sequences disclosed herein. These mismatched bases should not be within the last three or four bases of the 3' end of the primer.

B. Additional criteria for: Miniswine-specific PCR assay
a. Primers are selected such that there are at least one or two mismatches between miniswine and domestic pig sequences. At least one of these mismatches should be located within the last three or four bases at the 3' end of the primer. Preferably, these mismatches would be a change from either a G or C in miniswine to either an A or T in domestic pig.

RT-PCR Strategy

There are a number of commercially available RT-PCR Kits for routine amplification of fragments. Several primer pairs should be tested to confirm Tm and specificity. Location of primers within the sequence depends in part on what question is being answered. RT-PCR should answer questions about expression and presence of RV sequences. PCR will not necessarily answer the question of whether the retroviral sequence is full-length or encodes a replication competent retrovirus. A positive signal in these tests only says there is RV sequence present. Indication of the possibility of full-length viral genomes being present can be obtained by performing long PCR using primers in U5 and U3. A commercial kit for long RT-PCR amplification is available (Takara RNA LA PCR Kit). Confirmation of full-length viral genomes requires infectivity studies and/or isolation of viral particles.

Northern analyses would complement RT-PCR data. Detection of bands at the predicted size of full-length viral genomes with hybridization probes from env, U3 or U5 would provide stronger evidence. The presence of other small bands hybridizing would indicate the amount of defective viral fragments present.

Elisa-Based Assay to Detect the Presence of Porcine Retroviral Proteins, Polypeptides or Peptides In addition to the use of nucleic acid-based, e.g., PCR-based assays, to detect the presence of retroviral sequences, ELISA based assays can detect the presence of porcine retroviral proteins, polypeptides and peptides.

The basic steps to developing an ELISA include (a) generation of porcine retroviral specific peptides, polypeptides and proteins; (b) generation of antibodies which are specific for the porcine retroviral sequences; (c) developing the assay.

Using the retroviral sequences disclosed herein, antigenic peptides can be designed using computer based programs such as MacVector or Geneworks to analyse the retroviral sequences. Alternatively, it is possible to express the porcine retroviral sequences in gene expression systems and to purify the expressed polypeptides or proteins. After synthesis, the peptides, polypeptides or proteins are used to immunize mice or rabbits and to develop serum containing antibodies.

Having obtained the porcine retroviral specific antibodies the ELISA can be developed as follows. ELISA plates are coated with a volume of polyclonal or monoclonal antibody (capture antibody) which is reactive with the analyte to be tested. Such analytes include porcine retroviruses or retroviral proteins such as env or p24. The ELISA plates are then incubated at 4° C. overnight. The coated plates are then washed and blocked with a volume of a blocking reagent to reduce or prevent non-specific hybridization. Such blocking reagents include bovine serum albumin (BSA), fetal bovine serum (FBS), milk, or gelatin. The temperature for the blocking process is 37° C. Plates can be used immediately or stored frozen at −20° C. until needed. The plates are then washed, loaded with a serial dilution of the analyte, incubated at 37° C., and washed again. Bound analyte is detected using a detecting antibody. Detecting antibodies include enzyme-linked, fluoresceinated, biotin-conjugated or other tagged polyclonal or monoclonal antibodies which are reactive with the analyte. If monoclonal antibodies are used the detecting( antibody should recognize an epitope which is different from the capture antibody.

Other Embodiments

In another aspect, the invention provides a substantially pure nucleic acid having, or comprising, a nucleotide sequence which encodes a swine or miniature swine, e.g., a Tsukuba-1 retroviral gag polypeptide.

In preferred embodiments: the nucleic acid is or includes the nucleotide sequence from nucleotides 2452–4839 of SEQ ID NO:1; the nucleic acid is at least 60%, 70%, 80%, 90%, 95%, 98%, or 99% homologous with a nucleic acid sequence corresponding to nucleotides 2452–4839 of SEQ ID NO:1; or by a sequence which, hybridizes under high stringency conditions to nucleotides 2452–4839 of SEQ ID NO:1; the nucleic acid includes a fragment of SEQ ID NO:1 which is at least 25, 50, 100, 200, 300, 400, 500, or 1,000 bases in length; the nucleic acid differs from the nucleotide sequence corresponding to nucleotides 2452–4839 of SEQ ID NO:1 due to degeneracy in the genetic code; the nucleic acid differs from the nucleic acid sequence corresponding to nucleotides 2452–4839 of SEQ ID NO:1 by at least one nucleotide but by less than 5, 10, 15 or 20 nucleotides and preferably which encodes an active peptide.

In yet another preferred embodiment, the nucleic acid of the invention hybridizes under stringent conditions to a nucleic acid probe corresponding to at least 12 consecutive nucleotides from nucleotides 2452–4839 of SEQ ID NO:1, or more preferably to at least 20 consecutive nucleotides from nucleotides 2452–4839 of SEQ ID NO:1, or more preferably to at least 40 consecutive nucleotides from nucleotides 2452–4839 of SEQ ID NO:1.

In another aspect, the invention features, a purified recombinant nucleic acid having at least 50%, 60%, 70%, 80%, 90%, 95%, 98%, or 99% homology with a nucleotide sequence corresponding to nucleotides 2452–4839 of SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from nucleotides 2452–4839 of SEQ ID NO:1, or naturally occurring mutants thereof. In preferred embodiments, the probe or primer further includes a label attached thereto. The label can be, e.g., a radioisotope, a fluorescent compound, an enzyme, and/or an enzyme co-factor. Preferably the oligonucleotide is at least 10 and less than 20, 30, 50, 100, or 150 nucleotides in length. Preferred primers of the invention include oligonucleotides having a nucleotide sequence shown in any of SEQ ID NOs:32–37.

The invention involves nucleic acids, e.g., RNA or DNA, encoding a polypeptide of the invention. This includes double stranded nucleic acids as well as coding and antisense single strands.

In another aspect, the invention provides a substantially pure nucleic acid having, or comprising, a nucleotide sequence which encodes a swine or miniature swine, e.g., a Tsukuba-1 retroviral pol polypeptide.

In preferred embodiments: the nucleic acid is or includes the nucleotide sequence corresponding to nucleotides 4871–8060 of SEQ ID NO:1; the nucleic acid is at least 60%, 70%, 80%, 90%, 95%, 98%, or 99% homologous with a nucleic acid sequence corresponding to nucleotides 4871–8060 of SEQ ID NO:1; or by a sequence which, hybridizes under high stringency conditions to nucleotides 4871–8060 of SEQ ID NO 1; the nucleic acid includes a fragment of SEQ ID NO:1 which is at least 25, 50, 100, 200, 300, 400, 500, or 1,000 bases in length; the nucleic acid differs from the nucleotide sequence corresponding to nucleotides 4871–8060 of SEQ ID NO:1 due to degeneracy in the genetic code; the nucleic acid differs from the nucleic acid sequence corresponding to nucleotides 4871–8060 of SEQ ID NO:1 by at least one nucleotide but by less than 5, 10, 15 or 20 nucleotides and preferably which encodes an active peptide.

In yet another preferred embodiment, the nucleic acid of the invention hybridizes under stringent conditions to a nucleic acid probe corresponding to at least 12 consecutive nucleotides from nucleotides 4871–8060 of SEQ ID NO:1, or more preferably to at least 20 consecutive nucleotides from nucleotides 4871–8060 of SEQ ID NO:1, or more preferably to at least 40 consecutive nucleotides from nucleotides 4871–8060 of SEQ ID NO:1.

In another aspect, the invention features, a purified recombinant nucleic acid having at least 50%, 60%, 70%, 80%, 90%, 95%, 98%, or 99% homology with a nucleotide sequence corresponding to nucleotides 4871–8060 of SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from nucleotides 4871–8060 of SEQ ID NO:1, or naturally occurring mutants thereof. In preferred embodiments, the probe or primer further includes a label attached thereto. The label can be, e.g., a radioisotope, a fluorescent compound, an enzyme, and/or an enzyme co-factor. Preferably the oligonucleotide is at least 10 and less than 20, 30, 50, 100, or 150 nucleotides in length. Preferred primers of the invention include oligonucleotides having a nucleotide sequence shown in any of SEQ ID NOs:38–47.

The invention involves nucleic acids, e.g., RNA or DNA, encoding a polypeptide of the invention. This includes double stranded nucleic acids as well as coding and antisense single strands.

In another aspect, the invention provides a substantially pure nucleic acid having, or comprising, a nucleotide sequence which encodes a swine or miniature swine, e.g., a Tsukuba-1 retroviral env polypeptide.

In preferred embodiments: the nucleic acid is or includes the nucleotide sequence corresponding to nucleotides 2–1999 of SEQ ID NO:1; the nucleic acid is at least 60%, 70%, 80%, 90%, 95%, 98%, or 99% homologous with a nucleic acid sequence corresponding to nucleotides 2–1999 of SEQ ID NO:1; or by a sequence which, hybridizes under high stringency conditions to nucleotides 2–1999 of SEQ ID NO:1; the nucleic acid includes a fragment of SEQ ID NO:1 which is at least 25, 50, 100, 200, 300, 400, 500, or 1,000 bases in length; the nucleic acid differs from the nucleotide sequence corresponding to nucleotides 2–1999 of SEQ ID NO:1 due to degeneracy in the genetic code; the nucleic acid differs from the nucleic acid sequence corresponding to nucleotides 2–1999 of SEQ ID NO:1 by at least one nucleotide but by less than 5, 10, 15 or 20 nucleotides and preferably which encodes an active peptide.

In yet another preferred embodiment, the nucleic acid of the invention hybridizes under stringent conditions to a nucleic acid probe corresponding to at least 12 consecutive nucleotides from nucleotides 2–1999 of SEQ ID NO:1, or more preferably to at least 20 consecutive nucleotides from nucleotides 2–1999 of SEQ ID NO:1, or more preferably to at least 40 consecutive nucleotides from nucleotides 2–1999 of SEQ ID NO:1. In another aspect, the invention features, a purified recombinant nucleic acid having at least 50%, 60%, 70%, 80%, 90%, 95%, 98%, or 99% homology with a nucleotide sequence corresponding to nucleotides 2–1999 of SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from nucleotides 2–1999 of SEQ ID NO:1, or naturally occurring mutants thereof. In preferred embodiments, the probe or primer further includes a label attached thereto. The label can be, e.g., a radioisotope, a fluorescent compound, an enzyme, and/or an enzyme co-factor. Preferably the oligonucleotide is at least 10 and less than 20, 30, 50, 100, or 150 nucleotides in length. Preferred primers of the invention include oligonucleotides having a nucleotide sequence shown in any of SEQ ID NOs:6–31.

The invention includes nucleic acids, e.g., RNA or DNA, encoding a polypeptide of the invention. This includes double stranded nucleic acids as well as coding and antisense single strands.

Included in the invention are: allelic variations, natural mutants, induced mutants, that hybridize under high or low stringency conditions to the nucleic acid of SEQ ID NO:1, 2, or 3 (for definitions of high and low stringency see Current Protocols in Molecular Biology, John Wiley & Sons, New York, 1989, 6.3.1–6.3.6, hereby incorporated by reference).

The invention also includes purified preparations of swine or miniature swine retroviral polypeptides, e.g., gag pol, or env polypeptides, or fragments thereof, preferably biologically active fragments, or analogs, of such polypeptides. In preferred embodiments:

the polypeptides are miniature swine retroviruses polypeptides; the polypeptides are Tsukuba polypeptides; the polypeptides are gag, pol, or env polypeptides encoded by SEQ ID NO:1 or its complement, SEQ ID NO:2 or its complement, or SEQ ID NO:3 or its complement, or naturally occuring variants thereof.

A biologically active fragment or analog is one having any in vivo or in vitro activity which is characteristic of the Tsukuba-1 polypeptides described herein, or of other naturally occurring Tsukuba-1 polypeptides. Fragments include those expressed in native or endogenous cells, e.g., as a result of post-translational processing, e.g., as the result of the removal of an amino-terminal signal sequence, as well as those made in expression systems, e.g., in CHO cells. A useful polypeptide fragment or polypeptide analog is one which exhibits a biological activity in any biological assay for Tusukuba-1 polypeptide activity. Most preferably the fragment or analog possesses 10%, preferably 40%, or at least 90% of the activity of Tsukuba-1 polypeptides, in any in vivo or in vitro Tsukuba-1 polypeptide assay.

In order to obtain a such polypeptides, polypeptide-encoding DNA can be introduced into an expression vector, the vector introduced into a cell suitable for expression of the desired protein, and the peptide recovered and purified, by prior art methods. Antibodies to the polypeptides can be made by immunizing an animal, e.g., a rabbit or mouse, and recovering antibodies by prior art methods.

The invention also features a purified nucleic acid, which has least 60%, 70%, 72%, more preferably at least 85%, more preferably at least 90%, more preferably at least 95%, most preferably at least 98%, 99% or 100% sequence identity or homology with SEQ ID NO:1 or its complement, SEQ ID NO:2 or its complement, or SEQ ID NO:3 or its complement.

In preferred embodiments the nucleic acid is other than the entire retroviral genome of SEQ ID NO:1 or its complement, SEQ ID NO:2 or its complement, or SEQ ID NO:3 or its complement, e.g., it is at least 1 nucleotide longer, or at least 1 nucleotide shorter, or differs in sequence at at least one position. E.g., the nucleic acid is a fragment of the sequence of SEQ ID NO:1 or its complement, SEQ ID NO:2 or its complement, or SEQ ID NO:3 or its complement, or it includes sequence additional to that of SEQ ID NO:1, or its complement, SEQ ID NO:2 or its complement, or SEQ ID NO:3 or its complement.

In preferred embodiments: the sequence of the nucleic acid differs from the corresponding sequence of SEQ ID NO:1 or its complement, SEQ ID NO:2 or its complement, or SEQ ID NO:3 or its complement, by 1, 2, 3, 4, or 5 base pairs; the sequence of the nucleic acid differs from the corresponding sequence of SEQ ID NO:1 or its complement, SEQ ID NO:2 or its complement, or SEQ ID NO:3 or its complement, by at least 1, 2, 3, 4, or 5 base pairs but less than 6, 7, 8, 9, or 10 base pairs. In other preferred embodiments: the nucleic acid is at least 10, more preferably at least 15, more preferably at least 20, most preferably at least 25, 30, 50, 100, 1000, 2000, 4000, 6000, or 8060 nucleotides in length; the nucleic acid is less than 15, more preferably less than 20, most preferably less than 25, 30, 50, 100, 1000, 2000, 4000, 6000, or 8060 nucleotides in length.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method for screening a cell or a tissue for the presence or expression of a swine or miniature swine retrovirus comprising:

contacting a target nucleic acid from the cell or tissue with a second nucleic acid selected from the group of: a sequence which can specifically hybridize to the sequence of SEQ ID NO:1, or its complement of the same length; a sequence which can specifically hybridize to the sequence of SEQ ID NO:2, or its complement of the same length; a sequence which can specifically hybridize to tie sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4839 or nucleotides 3112–4693 of SEQ ID NO:1, nucleotides 598–2169 of SEQ ID NO:2, or nucleotides 585–2156, of SEQ ID NO:3; a nucleic acid which can specifically hybridize to a sense or antisense sequence which encodes a pol protein, said sense pol antisense sequence being selected from the group consisting of pol-encoding nucleotides of SEQ ID NO:1, pol-encoding nucleotides of SEQ ID NO:2, and pol-encoding nucleotides of SEQ ID NO:3; a nucleic acid which can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO-2, and env-encoding nucleotides of SEQ ID NO:3; a nucleic acid which can specifically hybridize to a sense or antisense sequence from nucleotides 2–1999 or nucleotides 86–1999 of SEQ ID NO:1, nucleotides 4738–6722 of SEQ ID NO:2, or nucleotides 5620–7533 of SEQ ID NO:3, under conditions in which hybridization can occur, hybridization being indicative of the presence or expression of an endogenous swine or miniature swine retrovirus or retroviral sequence in the cell or tissue.

2. A method for screening a swine or miniature swine genome for the presence of a porcine retrovirus, comprising:

contacting the swine or miniature swine genomic DNA with a second nucleic acid selected from the group of: a sequence which can specifically hybridize to the sequence of SEQ ID NO:1, or its complement of the same length; a sequence which can specifically hybridize to the sequence of SEQ ID NO:2, or its complement of the same length; a sequence which can specifically hybridize to the sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4839 or nucleotides 3112–4683 of SEQ ID NO:1, nucleotides 598–2169 of SEQ ID NO:2, or nucleotides 585–2156, of SEQ ID NO:3; a nucleic acid which can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3; a nucleic acid which can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO:1, nucleotides 4738–6722 of SEQ ID NO:2, or nucleotides 5620–7533 of SEQ ID NO:3, under conditions in which the sequences can hybridize, hybridization being indicative of the presence of the endogenous porcine retroviral sequence in the swine or miniature swine genome.

3. A method of assessing the potential risk associated with the transplantation of a graft from a donor swine or miniature swine into a recipient animal, comprising:

contacting a target nucleic acid from the donor, recipient, or the graft, with a second nucleic acid selected from the group of: a sequence which can specifically hybridize to the sequence of SEQ ID NO:1, or its complement of the same length; a sequence which can specifically hybridize to the sequence of SEQ ID NO:2, or its complement of the same length; a sequence which can specifically hybridize to the sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4839 or nucleotides 3112–4683 of SEQ ID NO:1, nucleotides 598–2169 of SEQ ID NO:2, or nucleotides 585–2156, of SEQ ID NO:3; a nucleic acid which can specifically hybridize to a sense or antisense sequence which encodes a pol protein, said sense or antisense sequence being selected from the group consisting of pol-encoding nucleotides of SEQ ID NO:1, pot-encoding nucleotides of SEQ ID NO:2, and pol-encoding nucleotides of SEQ ID NO:3; a nucleic acid which can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO:1, nucleotides 4738–6722 of SEQ ID NO:2, or nucleotides 5620–7533 of SEQ ID NO:3, under conditions in which the sequences can hybridize, hybridization being indicative of a risk associated with the transplantation.

4. A method of providing a swine or miniature swine free of an activatable retrovirus insertion at a preselected site, comprising:
performing a cross between a first swine or miniature swine having a retroviral insertion at the preselected site and a second swine or miniature swine not having a retroviral insertion at a preselected site, and recovering a progeny swine or miniature swine, not having the insertion, wherein the presence or absence of the retroviral insertion is determined by contacting the genome of a swine or miniature swine with a nucleic acid chosen from the group of: a sequence which can specifically hybridize to the sequence of SEQ ID NO:1, or its complement of the same length; a sequence which can specifically hybridize to the sequence of SEQ ID NO:2, or its complement of the same length; a sequence which can specifically hybridize to the sequence of SEQ ID NO,3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4939 or nucleotides 31 12–4693 of SEQ ID NO:1, nucleotides 598–2169 of SEQ ID NO:2, or nucleotides 585–2156, of SEQ ID NO:3; a nucleic acid which can specifically hybridize to a sense or antisense sequence which encodes a pol protein, said sense or antisense sequnce being selected from the group consisting of pol-encoding nucleotides of SEQ ID NO 1, pol-encoding nucleotides of SEQ ID NO-.2 and pol-encoding nucleotides of SEQ ID NO:3; a nucleic acid which can specifically hybridize to a sense or antisense sequence from nucleotides 4971–9860 of SEQ ID NO:1, nucleotides 2320–4737 of SEQ ID NO:2, or nucleotides 2307–5741 of SEQ ID NO:3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO;1, nucleotides 4738–6722 of SEQ ID NO:2, or nucleotides 5620–7533 of SEQ ID NO,3.

5. A method of localizing the origin of a porcine retroviral infection comprising:
contacting a target nucleic acid from a graft or organ with a second nucleic acid selected from the group of: a sequence which can specifically hybridize to the sequence of SEQ ID NO:1, or its complement of the same length; a sequence which can specifically hybridize to the sequence of SEQ ID NO:2, or its complement of the same length; a sequence which can specifically hybridize to the sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4839 or nucleotides 3112–4683 of SEQ ID NO:1, nucleotides 598–2169 of SEQ ID NO:2, or nucleotides 585–2156, of SEQ ID NO:3; a nucleic acid which can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3; a nucleic acid which can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO,3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO;1, nucleotides 4738–6722 of SEQ ID NO:2, or nucleotides 5620–7533 of SEQ ID NO:3,
contacting a target nucleic acid from the recipient with the second nucleic acid selected from the group of: a sequence which can specifically hybridize to the sequence of SEQ ID NO:1, or its complement of the same length; a sequence which can specifically hybridize to the sequence of SEQ ID NO:2, or its complement of the same length; a sequence which ran specifically hybridize to the sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4939 or nucleotides 3112–4683 of SEQ ID NO:1, nucleotides 598–2169 of SEQ ID NO:2, or nucleotides 585–2156, of SEQ ID NO:3; a nucleic acid which can specifically hybridize to a sense or antisense sequence which encodes a pol protein, said sense or antisense sequence being selected from the group consisting of pol-encoding nucleotides of SEQ ID NO:1, pot-encoding nucleotides of SEQ ID NO:2. and pol-encoding nucleotides of SEQ ID NO:3; a nucleic acid which can specifically hybridize to a sense or antisense sequence from nucleotides 4971–8060 of SEQ ID NO:1. nucleotides 2320–4737 of SEQ ID NO:2, or nucleotides 2307–5741 of SEQ ID NO:3; a nucleic acid sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO:1, nucleotides 4738–6722 of SEQ ID NO:2, or nucleotides 5620–7533 of SEQ ID NO:3; wherein hybridization to the nucleic acid from the graft or organ correlates with the porcine retroviral infection in the graft or organ and hybridization to the nucleic acid from the recipient correlates with the porcine retroviral infection in the recipient, thereby localizing the origin of a porcine retroviral infection.

6. A method of screening a human subject for the presence or expression of an endogenous porcine retrovirus comprising:

contacting a target nucleic acid derived from the human subject with a second nucleic acid selected from the group of: a sequence which can specifically hybridize to the sequence of SEQ ID NO:1, or its complement of the same length; a sequence which can specifically hybridize to the sequence of SEQ ID NO:2, or its complement of the same length; a sequence which can specifically hybridize to the sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4839 or nucleotides 3112–4683 of SEQ ID NO:1, nucleotides 598–2169 of SEQ ID NO:2, or nucleotides 585–2156, of SEQ ID NO:3; a nucleic acid which can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO,2, and pol-encoding nucleotides of SEQ ID NO:3; a nucleic acid which can specifically hybridize to a sense or antisense sequence from nucleotides 4971–8060 of SEQ ID NO:1, nucleotides 2320–4737 of SEQ ID NO:2, or nucleotides 2307–5741 of SEQ ID NO:3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO:1, nucleotides 4738–6722 of SEQ ID NO:2, or nucleotides 5620–7533 of SEQ ID NO:3, under conditions in which the sequences can hybridize, hybridization being indicative of the presence of the endogenous porcine retrovirus or retroviral sequences in the human subject.

7. A method of determining the copy number or size of a porcine retrovirus, comprising:

contacting a target nucleic acid from the donor, recipient, or a graft, with a second nucleic acid selected from the group of: a sequence which can specifically hybridize to the sequence of SEQ ID NO:1, or its complement of the same length; a sequence which can specifically hybridize to the sequence of SEQ ID NO:2, or its complement of the sane length; a sequence which can specifically hybridize to the sequence of SEQ ID NO:3, or its complement of the same length; a nucleic acid which can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3; a nucleic acid which can specifically hybridize to a sense or antisense sequence from nucleotides 2452–4939 or nucleotides 3112–4683 of SEQ ID NO:1, nucleotides 599–2169 of SEQ ID NO:2, or nucleotides 585–2156, of SEQ ID NO:3; a nucleic acid which can specifically hybridize to sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3; a nucleic acid which can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3; a nucleic acid which can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3; a nucleic acid which can specifically hybridize to a sense or antisense sequence from nucleotides 2–1999 or nucleotides 86–1999 of SEQ ID NO:1, nucleotides 4738–6722 of SEQ ID NO:2, or nucleotides 5620–7533 of SEQ ID NO:3.

8. The method of claim 1, wherein the second nucleic acid sequence can specifically hybridize to SEQ ID NO:1, or its complement of the same length.

9. The method of claim 1, wherein the second nucleic acid sequence can specifically hybridize to SEQ ID NO:2, or its complement of the same length.

10. The method of claim 1, wherein the second nucleic acid sequence can specifically hybridize to SEQ ID NO:3, or its complement of the same length.

11. The method of claim 1, wherein the second nucleic acid sequence can specifically hybridize to a sense or antisense sequence which encodes an env proteins said sense or antisense sequence being selected from the group consisting of env-encoding nucleotides of SEQ ID NO:1, env-encoding nucleotides of SEQ ID NO:2, and env-encoding nucleotides of SEQ ID NO:3.

12. The method of claim 1, wherein the second nucleic acid sequence can specifically hybridize to a sense or antisense sequence from nucleotides 2–1999 or nucleotides 86–1999 of SEQ ID NO:1.

13. The method of claim 1, wherein the second nucleic acid sequence can specifically hybridize to a sense or antisense sequence from nucleotides 4738–6722 of SEQ ID NO:2.

14. The method of claim 1, wherein the second nucleic acid sequence can specifically hybridize to a sense or antisense sequence from nucleotides 5620–7533 of SEQ ID NO:3.

15. The method of claim 1, wherein the cell or tissue is from a human.

16. The method of claim 3, wherein the second nucleic acid sequence can specifically hybridize to SEQ ID NO:1, or its complement of the same length.

17. The method of claim 3, wherein the second nucleic acid sequence can specifically hybridize to SEQ ID NO:2, or its complement of the same length.

18. The method of claim 3, wherein the second nucleic acid sequence can specifically hybridize to SEQ ID NO:3, or its complement of the same length.

19. The method of claim 3, wherein the second nucleic acid sequence can specifically hybridize to a sense or antisense sequence which encodes an env protein, wherein said sense or antisense sequence being selected from the group consisting of env-encoding nucleotides of SEQ ID NO:1, env-encoding nucleotides of SEQ ID NO:2, and env-encoding nucleotides of SEQ ID NO:3.

20. The method of claim 3, wherein the second nucleic acid sequence can specifically hybridize to a sense or antisense sequence from nucleotides 2–1999 or nucleotides 86–1999 of SEQ ID NO:1.

21. The method of claim 3, wherein the second nucleic acid sequence can specifically hybridize to a sense or antisense sequence from nucleotides 4738–6722 of SEQ ID NO:2.

22. The method of claim 3, wherein the second nucleic acid sequence can specifically hybridize to a sense or antisense sequence from nucleotides 5620–7533 of SEQ ID NO:3.

23. The method of claim 3, wherein the recipient animal is a human.

24. The method of claim 6, wherein the second nucleic acid sequence call specifically hybridize to SEQ ID NO:1, or its complement of the same length.

25. The method of claim 6, wherein the second nucleic acid sequence can specifically hybridize to SEQ ID NO:2, or its complement of the same length.

26. The method of claim 6, wherein the second nucleic acid sequence can specifically hybridize to SEQ ID NO:3, or its complement of the same length.

27. The method of claim 6, wherein the second nucleic acid sequence can specifically hybridize to a sense or antisense sequence which encodes all env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3.

28. The method of claim 6, wherein the second nucleic acid sequence can specifically hybridize to a sense or antisense sequence from nucleotides 2–1999 or nucleotides 96–1999 of SEQ ID NO:1.

29. The method of claim 6, wherein the second nucleic acid sequence can specifically hybridize to a sense or anti sense sequence from nucleotides 4738–6722 of SEQ ID NO:2.

30. The method of claim 6, wherein the second nucleic acid sequence can specifically hybridize to a sense or antisense sequence from nucleotides 5620–7533 of SEQ ID NO:3.

31. The method of claim 1, wherein the cell or tissue is a miniature swine cell or tissue.

32. The method of claim 1, wherein the cell or tissue is a human cell or tissue.

33. The method of claim 3, wherein the target nucleic acid is from a human recipient.

34. The method of claim 3 wherein the target nucleic acid is from a miniature swine.

35. The method of claim 5 wherein the graft or organ is from a miniature swine and the recipient is a human.

36. The method of claim 7, wherein the target nucleic acid is from a miniature swine donor or graft.

37. The method of claim 7, wherein the target nucleic acid is from a miniature swine donor or graft.

38. The method of claim 1, wherein the second nucleic acid can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3.

39. The method of claim 3, wherein the second nucleic acid can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3.

40. The method of claim 6, wherein the second nucleic acid can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3.

41. The method of claim 1, wherein the second nucleic acid can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3.

42. The method of claim 1, wherein the second nucleic acid can specifically hybridize to a sense or antisense sequence from nucleotides 2452–4839 or 3112–4683 of SEQ ID NO:1, nucleotides 598–2169 of SEQ ID NO:2, or nucleotides 585–2156, of SEQ ID NO:3.

43. The method of claim 1, wherein the second nucleic acid can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3.

44. The method of claim 2, wherein the second nucleic acid sequence can specifically hybridize to SEQ ID NO:1, or its complement of the same length.

45. The method of claim 2, wherein the second nucleic acid sequence can specifically hybridize to SEQ ID NO:2, or its complement of the same length.

46. The method of claim 2, wherein the second nucleic acid sequence can specifically hybridize to SEQ ID NO:3, or its complement of the same length.

47. The method of claim 2, wherein the second nucleic acid sequence can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3.

48. The method of claim 2, wherein the second nucleic acid sequence can specifically hybridize to a sense or antisense sequence from nucleotides 2–1999 or nucleotides 86–1999 of SEQ ID NO:1.

49. The method of claim 2, wherein the second nucleic acid sequence can specifically hybridize to a sense of antisense sequence from nucleotides 4738–6722 of SEQ ID NO:2.

50. The method of claim 2, wherein the second nucleic acid sequence can specifically hybridize to a sense or antisense sequence from nucleotides 5620–7533 of SEQ ID NO:3.

51. The method of claim 2, wherein the second nucleic acid can specifically hybridize to a sense or antisense sequence which encodes a gag protein, said sense or antisense sequence being selected from the group consisting of gag-encoding nucleotides of SEQ ID NO:1 gag-encoding nucleotides of SEQ ID NO:2, and gag-encoding nucleotides of SEQ ID NO:3.

52. The method of claim 2, wherein the second nucleic acid can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3.

53. The method of claim 2, wherein wherein the second nucleic acid can specifically hybridize to a sense or antisense sequence from nucleotides 2452–4839 or 3112–4683 of SEQ ID NO:1, nucleotides 598–2169 of SEQ ID NO:2, or nucleotides 585–2156, of SEQ ID NO:3.

54. The method of claim 2, wherein wherein the second nucleic acid can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3.

55. The method of claim 3, wherein the second nucleic acid can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3.

56. The method of claim 3, wherein the second nucleic acid can specifically hybridize to a sense or antisense sequence from nucleotides 2452–4839 or 3112–4683 of SEQ ID NO:1, nucleotides 598–2169 of SEQ ID NO:2, or nucleotides 595–2156, of SEQ ID NO:3.

57. The method of claim 3, wherein the second nucleic acid can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3.

58. The method of claim 4, wherein the nucleic acid sequence can specifically hybridize to SEQ ID NO:1, or its complement of the same length.

59. The method of claim 4, wherein the nucleic acid sequence can specifically hybridize to SEQ ID NO:2, or its complement of the same length.

60. The method of claim 4, wherein the nucleic acid sequence can specifically hybridize to SEQ ID NO:3, or its complement of the same length.

61. The method of claim 4, wherein the nucleic acid sequence can specifically hybridize to a sense or an antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3.

62. The method of claim 4, wherein the nucleic acid sequence can specifically hybridize to a sense or an antisense sequence from nucleotides 2–1999 or nucleotides 96–1999 of SEQ ID NO:1.

63. The method of claim 4, wherein the nucleic acid sequence can specifically hybridize to a sense or antisense sequence from nucleotides 4738–6722 of SEQ ID NO:2.

64. The method of claim 4, wherein the nucleic acid sequence can specifically hybridize to a sense or antisense sequence from nucleotides 5620–7533 of SEQ ID NO:3.

65. The method of claim 4, wherein the nucleic acid can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3.

66. The method of claim 4, wherein the nucleic acid can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3.

67. The method of claim 4 wherein the nucleic acid can specifically hybridize to a sense or antisense sequence from nucleotides 2452–4939 or 3112–4683 of SEQ ID NO:1, nucleotides 598–2169 of SEQ ID NO:2, or nucleotides 585–2156, of SEQ ID NO:3.

68. The method of claim 4, wherein the nucleic acid can specifically hybridize to a sense or antisense sequence from nucleotides 4871–8060 of SEQ ID NO:1 nucleotides 2320–4737 of SEQ ID NO:2, or nucleotides 2307–5741 of SEQ ID NO:3.

69. The method of claim 5, wherein the second nucleic acid sequence can specifically hybridize to SEQ ID NO:1, or its complement of the same length.

70. The method of claim 5, wherein the second nucleic acid sequence can specifically hybridize to SEQ ID NO:2, or its complement of the same length.

71. The method of claim 5, wherein the second nucleic acid sequence can specifically hybridize to SEQ ID NO:3, or its complement of the same length.

72. The method of claim 5, wherein the second nucleic acid sequence can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3.

73. The method of claim 5, wherein the second nucleic acid sequence can specifically hybridize to a sense or antisense sequence from nucleotide 2–1999 or nucleotides 86–1999 of SEQ ID NO:1.

74. The method of claim 5, wherein the second nucleic acid sequence can specifically hybridize to a sense or antisense sequence from nucleotides 4738–6722 of SEQ ID NO:2.

75. The method of claim 5, wherein the second nucleic acid sequence can specifically hybridize to a sense or antisense sequence from nucleotides 5620–7533 of SEQ ID NO:3.

76. The method of claim 5, wherein the second nucleic acid can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3.

77. The method of claim 5, wherein the second nucleic acid can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3.

78. The method of claim 5, wherein the second nucleic acid can specifically hybridize to a sense or antisense sequence from nucleotides 2452–4839 or 31 12–4683 of SEQ ID NO:1, nucleotides 598–2169 of SEQ ID NO:2, or nucleotides 585–2156, of SEQ ID NO:3.

79. The method of claim 5, wherein the second nucleic acid can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3.

80. The method of claim 6, wherein the second nucleic acid can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3.

81. The method of claim 6, wherein the second nucleic acid can specifically hybridize to a sense or antisense sequence from nucleotides 2452–4839 or 3112–4683 of SEQ ID NO:1, nucleotides 598–2169 of SEQ ID NO:02, or nucleotides 585–2156, of SEQ ID NO:3.

82. The method of claim 6, wherein the second nucleic acid can specifically hybridize to a sense or antisense sequence from nucleotides 4871–8060 of SEQ ID NO:1, nucleotides 2320–4737 of SEQ ID NO:2, or nucleotides 2307–5741 of SEQ ID NO:3.

83. The method of claim 7, wherein the second nucleic acid sequence can specifically hybridize to SEQ ID NO:1 or its complement of the same length.

84. The method of claim 7, wherein the second nucleic acid sequence can specifically hybridize to SEQ ID NO:2, or its complement of the same length.

85. The method of claim 7, wherein the second nucleic acid sequence can specifically hybridize to SEQ ID NO:3, or its complement of the same length.

86. The method of claim 7, wherein the second nucleic acid sequence can specifically hybridize to a sense or antisense sequence which encodes an env protein, said sense or antisense sequence being selected from the group consisting of env-encoding nucleotides of SEQ ID NO:1, env-encoding nucleotides of SEQ ID NO:2, and env-encoding nucleotides of SEQ ID NO:3.

87. The method of claim 7, wherein the second nucleic acid sequence can specifically hybridize to a sense or antisense sequence from nucleotides 2–1999 or nucleotides 86–1999 of SEQ ID NO:1.

88. The method of claim 7, wherein the second nucleic acid sequence can specifically hybridize to a sense or antisense sequence from nucleotides 4738–6722 of SEQ ID NO:2.

89. The method of claim 7, wherein the second nucleic acid sequence can specifically hybridize to a sense or antisense sequence from nucleotides 5620–7533 of SEQ ID NO:3.

90. The method of claim 7, wherein the second nucleic acid can specifically hybridize to a sense or antisense sequence which encodes a gag protein, said sense or antisense sequence being selected from the group consisting of gag-encoding nucleotides of SEQ ID NO:1, gag-encoding nucleotides of SEQ ID NO:2, and gag-encoding nucleotides of SEQ ID NO:3.

91. The method of claim 7, wherein the second nucleic acid can specifically hybridize to a sense or antisense sequence which encodes a pol protein, said sense or antisense sequence being selected from the group consisting of pol-encoding nucleotides of SEQ ID NO:1, pol-encoding nucleotides of SEQ ID NO:2, and pol-encoding nucleotides of SEQ ID NO:3.

92. The method of claim 7, wherein the second nucleic acid can specifically hybridize to a sense or antisense sequence from nucleotides 2452–4839 or 3112–4683 of SEQ ID NO:1, nucleotides 598–2169 of SEQ ID NO:2, or nucleotides 585–2156, of SEQ ID NO:3.

93. The method of claim 7, wherein the second nucleic acid can specifically hybridize to a sense or antisense sequence from nucleotides 4871–9060 of SEQ ID NO:1, nucleotides 2320–4737 of SEQ ID NO:2, or nucleotides 2307–5741 of SEQ ID NO:3.

* * * * *

UNITED STATES PATENT AND TRADEMARK OFFICE
CERTIFICATE OF CORRECTION

PATENT NO. : 6,190,861 B1
DATED : February 20, 2001
INVENTOR(S) : Jay A. Fishman It is certified that error appears in the above-identified patent and that said Letters Patent is hereby corrected as shown below:

In the title page, the title, "MOLECULAR SEQUENCES OF SWINE RETROVIRUSES METHOD OF USING" should be -- MOLECULAR SEQUENCE OF SWINE RETROVIRUS AND METHODS OF USE--.

Column 87,
Line 21, "tie" should be --the--.
Line 31, "4693" should be --4683--.
Line 35, "pol" should be --or--.
Line 48, "NO-2" should be --NO:2--

Column 89,
Line 5, "pot-encoding" should be --pol-encoding--.
Line 41, "NO,3" should be --NO:3--.
Line 50, "4939" should be --4839--.
Line 50, "31 12-4693" should be --3112-4683--.
Line 56, "NO 1" should be --NO:1--.
Line 57, "NO-.2" should be --NO:2--.
Line 60, "4971-9860" should be --4871-8060--.

Column 90,
Line 6, "NO,3" should be --NO:3--.
Line 38, "NO,3" should be --NO:3--.
Line 46, "NO;1" should be --NO:1--.
Line 65, "4939" should be --4839--.

Column 91,
Line 5, "pot-encoding" should be --pol-encoding--.
Line 6, "NO:2" should be --NO:2,--.
Line 9, "4971" should be --4871--.
Line 54, "NO,2" should be --NO:2--.
Line 57, "4971" should be --4871--.

Column 92,
Line 14, "sane" should be --same--.
Line 24, "4939" should be --4839--.
Line 25, "599" should be --598--.
Line 59, "proteins" should be --protein,--.

UNITED STATES PATENT AND TRADEMARK OFFICE
CERTIFICATE OF CORRECTION

PATENT NO. : 6,190,861 B1
DATED : February 20, 2001
INVENTOR(S) : Jay A. Fishman It is certified that error appears in the above-identified patent and that said Letters Patent is hereby corrected as shown below:

Column 93,
Line 41, "call" should be --can--.
Line 59, "96" should be --86--.

Column 95,
Line 48, "595" should be --585--.

Column 96,
Line 6, "96" should be --86--.
Line 28, "4939" should be --4839--.
Line 54, "nucleotide" should be --nucleotides--.

Column 97,
Line 13, "31 12" should be --3112--.

Column 98,
Line 42, "9060" should be --8060--.

Signed and Sealed this

Seventh Day of August, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,190,861 B1
DATED : February 20, 2001
INVENTOR(S) : Jay A. Fishman Page 1 of 1

It is certified that error appears in the above-identified patent and that said Letters Patent is hereby corrected as shown below:

Column 94, claim 36,
Line 12, "miniature swine donor or graft" should be -- human recipient --.

Column 95, claim 53,
Line 27, "wherein wherein" should be -- wherein --.

Column 95, claim 54,
Line 32, "wherein wherein" should be -- wherein --.

Signed and Sealed this

Twenty-fifth Day of December, 2001

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,190,861 B1
DATED : February 20, 2001
INVENTOR(S) : Jay A. Fishman It is certified that error appears in the above-identified patent and that said Letters Patent is hereby corrected as shown below:

Column 94, claim 36,
Line 12, "human recipient" should be -- miniature swine donor or graft --.

Column 95, claim 53,
Line 27, "wherein wherein" should be -- wherein --.

Column 95, claim 54,
Line 32, "wherein wherein" should be -- wherein --.

This certificate supersedes Certificate of Correction issued December 25, 2001.

Signed and Sealed this

Twenty-third Day of July, 2002

*Attest:*

JAMES E. ROGAN
*Director of the United States Patent and Trademark Office*

*Attesting Officer*